(12) United States Patent
Page et al.

(10) Patent No.: US 8,796,280 B2
(45) Date of Patent: Aug. 5, 2014

(54) 2,3-DISUBSTITUTED PYRAZINESULFONAMIDES AS CRTH2 INHIBITORS

(75) Inventors: Patrick Page, Saint-Julien-en-Genevois (FR); Matthias Schwarz, Gland (CH); Eric Sebille, Le Poizat (FR); Christophe Cleva, La Tour (FR); Cedric Merlot, Collonges-sous-Saleve (FR); Maurizio Maio, Renens (CH)

(73) Assignee: Merck Serono, S.A., Coinsins, Vaud (CH)

( * ) Notice: Subject to any disclaimer, the term of this patent is extended or adjusted under 35 U.S.C. 154(b) by 0 days.

(21) Appl. No.: 11/918,294

(22) PCT Filed: Apr. 20, 2006

(86) PCT No.: PCT/EP2006/061706
§ 371 (c)(1),
(2), (4) Date: Jan. 22, 2008

(87) PCT Pub. No.: WO2006/111560
PCT Pub. Date: Oct. 26, 2006

(65) Prior Publication Data
US 2009/0054447 A1    Feb. 26, 2009

Related U.S. Application Data

(60) Provisional application No. 60/675,381, filed on Apr. 27, 2005.

(30) Foreign Application Priority Data

Apr. 21, 2005 (EP) ..................... 05103254

(51) Int. Cl.
*A61K 31/4965* (2006.01)
*C07D 409/12* (2006.01)
*C07D 401/10* (2006.01)
*C07D 241/22* (2006.01)
*C07D 413/10* (2006.01)
*C07D 405/12* (2006.01)
*C07D 403/10* (2006.01)
*C07D 401/12* (2006.01)

(52) U.S. Cl.
CPC ............ *C07D 241/22* (2013.01); *C07D 409/12* (2013.01); *C07D 401/10* (2013.01); *C07D 413/10* (2013.01); *C07D 405/12* (2013.01); *C07D 403/10* (2013.01); *C07D 401/12* (2013.01)
USPC ..................... 514/255.06; 544/336

(58) Field of Classification Search
CPC .................................................. A61K 31/4965
USPC ..................... 514/255.06; 544/336
See application file for complete search history.

(56) References Cited

U.S. PATENT DOCUMENTS

2004/0220237 A1    11/2004 Fu et al.

FOREIGN PATENT DOCUMENTS

| WO | WO 03/066629 A2 | 8/2003 |
|---|---|---|
| WO | WO 2004/032848 A2 | 4/2004 |
| WO | WO 2004/035543 A1 | 4/2004 |
| WO | WO 2004/058265 A1 | 7/2004 |
| WO | WO 2004/096777 A1 | 11/2004 |
| WO | WO 2004/106302 A1 | 12/2004 |
| WO | WO 2004/108692 A1 | 12/2004 |
| WO | WO 2004/108717 A1 | 12/2004 |
| WO | WO 2005/007094 A2 | 1/2005 |
| WO | WO 2005/102338 A1 | 11/2005 |
| WO | WO 2006/025783 A1 | 3/2006 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Lewis et al. "Prostaglandin D2 generation after activation of rat and human mast cells with anti-IgE" J. Immunol. (1982) 129, 1627.
Matsuoka et al. "Prostaglandin D2 as a mediator of allergic asthma" Science (2000) 287, 2013-2017.
Woodward et al. "Studies on the ocular pharmacology of prostaglandin D2" Invest Ophthalmol. Vis. Sci. (1990) 31, 138-146.
Woodward et al."Further studies on ocular responses to DP receptor stimulation" Eur. J. Pharmacol. (1993) 230, 327-333.
Nagata et al. "Selective expression of a novel surface molecule by human Th2 cells in vivo" J. Immunol. (1999) 162, 1278-1286.
Hirai et al. "Prostaglandin D2 selectively induces chemotaxis in T helper type 2 cells, eosinophils . . . " J. exp. Med. (2001) 193, 255-261.
Cosmi et al. "CRTH2 is the most reliable marker for the detection of circulating human type 2 Th . . . " Eur. J. Immunol. (2000) 30, 2972-2979.

(Continued)

*Primary Examiner* — Douglas M Willis
(74) *Attorney, Agent, or Firm* — EMD Serono Research and Development Institute; Thomas W. Brown

(57) ABSTRACT

The present invention is related to the use of 2,3 substituted pyrazine sulfonamides of formula (I)

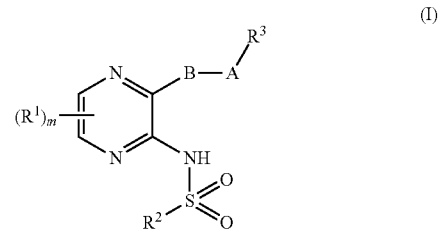

for the treatment and/or prevention of allergic diseases, inflammatory dermatoses and other diseases with an inflammatory component. Specifically, the present invention is related to the use of 2,3 substituted pyrazine sulfonamides for the modulation, notably the inhibition, of CRTH2 activity.

3 Claims, No Drawings

(56) References Cited

OTHER PUBLICATIONS

Bush et al. Handbook of asthma and rhinitis. 1st Ed., Abington: Blackwell Science (1997) 270.
Sawyer et al. "Molecular pharmacology of the human prostaglandin D2 receptor, CRTH2" Br. J. Pharmacol. (2002) 137, 1163-1172.
Xu et al. "T cell populations primed by hapten sensitization in contact sensitivity are distinguished by polarized patterns of cytokine . . . " J. Exp. Med. (1996) 183, 1001-1012.
Harrison et al. "The [35S]GTPγS binding assay: approaches and applications in pharmacology" Life Science (2003) 74, 489-508.
Xu et al. "T cell populations primed by hapten sensitization . . . " J. Exp. Med. (1996) 183, 1001-1012.

* cited by examiner

2,3-DISUBSTITUTED PYRAZINESULFONAMIDES AS CRTH2 INHIBITORS

The present application is filed under 35 U.S.C. §371 as a U.S. national phase application of PCT application no. PCT/EP2006/061706, which was filed Apr. 20, 2006. The aforementioned PCT application claimed benefit of priority of EP 05103254.8, which was filed Apr. 21, 2005 and U.S. 60/675,381, which was filed Apr. 27, 2005. The entire text of each of the aforementioned applications is incorporated herein by reference.

FIELD OF THE INVENTION

The present invention relates to 2,3 substituted pyrazine sulfonamides for use as pharmaceutical active compounds, as well as pharmaceutical formulations containing such 2,3 substituted pyrazine sulfonamides. Said derivatives are useful for the treatment and/or prevention of allergic diseases and inflammatory dermatoses. Specifically, the present invention is related to the use of 2,3 substituted pyrazine sulfonamides for the modulation, notably the inhibition of CRTH2 activity. The present invention furthermore relates to novel 2,3 substituted pyrazine sulfonamides as well as methods of their preparation.

BACKGROUND OF THE INVENTION

Prostaglandin D2 (PGD2) has long been associated with inflammatory and atopic conditions, specifically allergic diseases such as asthma, rhinitis and atopic dermatitis (Lewis et al. (1982) J. Immunol. 129, 1627). PGD2 belongs to a class of compounds derived from the 20-carbon fatty acid skeleton of arachidonic acid. In response to an antigen challenge, PGD2 is released in large amounts into the airway as well as to the skin during an acute allergic response. The DP receptor, which is a member of the G-protein coupled receptor (GPCR) subfamily, has long been thought to be the only receptor of PGD2. DP's role in allergic asthma has been demonstrated with DP deficient mice (Matsuoka et al. (2000) Science 287, 2013-2017). However, despite intense interest in the role of PGD2 in the inflammatory response, a direct link between DP receptor activation and PGD2-stimulated eosinophil migration has not been established (Woodward et al. (1990) Invest. Ophthalomol Vis. Sci. 31, 138-146; Woodward et al. (1993) Eur. J. Pharmacol. 230, 327-333).

More recently, another G-protein coupled receptor, referred to as "Chemoattractant Receptor-Homologous molecule expressed on T-Helper 2 cells" (CRTH2) (Nagata et al. (1999) J. Immunol. 162, 1278-1286, Hirai et al. (2001) J Exp. Med. 193, 255-261) has recently been identified as a receptor for PGD2 and this discovery has begun to shed light on the mechanism of action of PGD2. CRTH2, which is also referred to as DP2, GPR44 or DLIR, shows little structural similarity with the DP receptor and other prostanoid receptors. However, CRTH2 possesses similar affinity for PGD2. Among peripheral blood T lymphocytes, human CRTH2 is selectively expressed on Th2 cells and is highly expressed on cell types associated with allergic inflammation such as eosinophils, basophiles and Th2 cells. In addition, CRTH2 mediates PGD2 dependent cell migration of blood eosinophils and basophiles. Furthermore, increased numbers of circulating T cells expressing CRTH2 have been correlated with the severity of atopic dermatitis (Cosmi et al. (2000) Eur. J. Immunol. 30, 2972-2979). The interaction of CRTH2 with PGD2 plays a critical role in the allergen-induced recruitment of Th2 cells in the target tissues of allergic inflammation. Compounds that inhibit the binding of CRTH2 and PGD2 should therefore be useful for the treatment of allergic diseases.

Allergic disease, like asthma, and inflammatory dermatoses represent a major class of complex, and typically chronic, inflammatory diseases that currently affect about 10% of the population and that number appears to be increasing (Bush, R. K., Georgitis J. W., Handbook of asthma and rhinitis. 1st ed. (1997), Abingdon: Blackwell Science. 270). Atopic dermatitis is a chronic skin disease, wherein the skin becomes extremely itchy. It accounts for 10 to 20 percent of all visits to dermatologists. The increasing incidence of allergic diseases and inflammatory dermatoses worldwide underscores the need for new therapies to effectively treat or prevent these diseases. Currently, numerous classes of pharmaceutical agents are widely used to treat these diseases, for example, antihistamines, decongestants, anticholinergics, methylxanthines, cromolyns, corticosteroids, and leukotriene modulators. However, the usefulness of these agents is often limited by side effects and low efficacy.

It has been reported recently that 3-sulphur-substituted indole derivatives (A) exhibit CRTH2 activity (WO 04/106302, AstraZeneca AB) and are potentially useful for the treatment of various respiratory diseases.

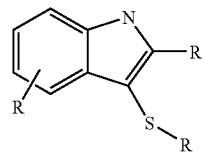

(A)

WO 04/096777 (Bayer Healthcare AG) relates to pyrimidine derivatives, which are useful for the treatment of diseases mediated by CRTH2.

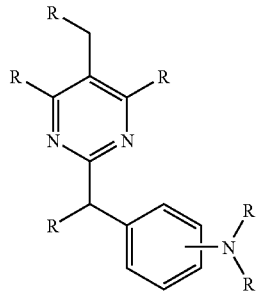

(B)

WO 04/035543 and WO 05/102338 (Warner-Lambert Company LLC) disclose tetrahydrochinoline derivatives as CRTH2 antagonists (C), which are also described to be effective in the treatment of neuropatic pain.

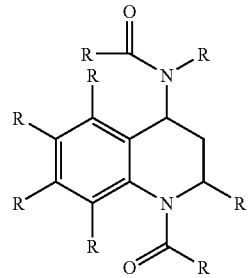

(C)

Specific tetrahydrochinoline derivatives as CRTH2 modulators are also provided by WO 04/032848 (Millennium Pharmaceutical Inc.) and WO 05/007094 (Tularik Inc.). These tetrahydrochinoline derivatives are said to be useful for treating disorders associated with allergic inflammation processes.

Other subfamilies of G protein-coupled receptor, namely CCR's and CXCR's, have been discussed as potential drug targets for the treatment of allergic diseases and autoimmune pathologies. WO 04/108692 and WO 04/108717 (AstraZeneca AB) disclose pyrazine sulfonamide compounds that modulate specifically CCR4.

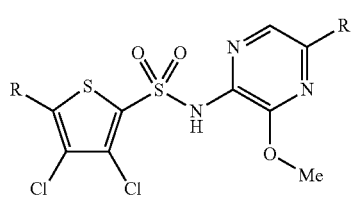

(D)

Pyrazine sulfonamide compounds have also been disclosed in WO 04/058265 as compounds that interact with G protein-coupled receptors.

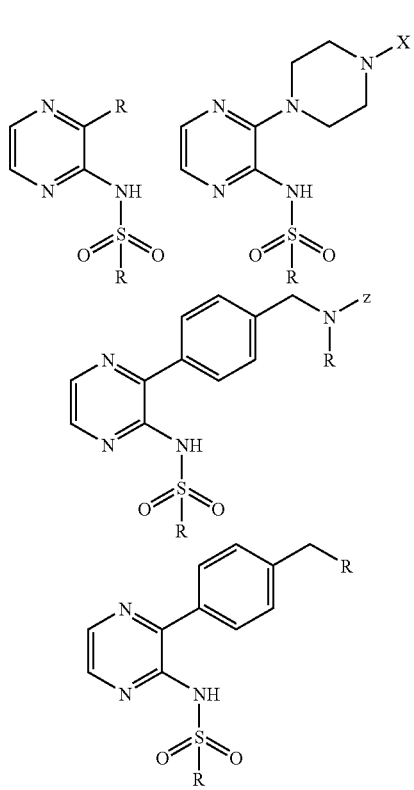

(E)

SUMMARY OF THE INVENTION

One aspect of the present invention consists in the use of 2,3 substituted pyrazine sulfonamides represented by the general formula (I) as pharmaceutical active compounds. Such compounds are suitable for the treatment and/or prevention of allergic disease and inflammatory dermatoses. Said compounds modulate a specific member of the G protein-coupled family, namely CRTH2. Specifically, the invention relates to 2,3 substituted pyrazine sulfonamides of Formula (I):

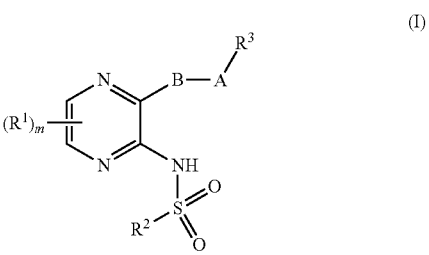

(I)

wherein A, B, $R^1$, $R^2$, $R^3$ and m are defined as described in the detailed description below, for use as a medicament.

The invention further provides a pharmaceutical composition comprising a compound of Formula (I), together with a pharmaceutically acceptable excipient or carrier.

The invention further relates to the use of compounds of Formula I for the preparation of a medicament for the treatment and/or prevention of diseases selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropatic pain, and other inflammatory diseases such as rheumatoid arthritis, multiple sclerosis, osteoarthritis, and inflammatory bowel disease (IBD) and other diseases or disorders associated with CTRH2 activity. Specifically the present invention is related to the use of compounds of Formula I for the modulation, notably the inhibition of CRTH2 activity.

The invention further relates to a method for treating and/or preventing a patient suffering from a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropatic pain, and other inflammatory diseases such as rheumatoid arthritis, multiple sclerosis, osteoarthritis, and inflammatory bowel disease (IBD) and other diseases and disorders associated with CTRH2 activity, by administering a compound according to Formula (I).

The invention further relates to the use of compounds of Formula I for the preparation of a pharmaceutical composition.

The invention finally relates to novel compounds of Formula I as well as to methods to synthesize these molecules.

DESCRIPTION OF THE INVENTION

The following paragraphs provide definitions of various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenanthrenyl and the like. The aryl ring may be also fused to a heterocycloalkyl group. Such fused aryls include dihydrobenzimidazole-2-one, benzo[1,3]dioxole and the like.

"$C_1$-$C_6$-alkyl aryl" refers to $C_1$-$C_6$-alkyl groups having an aryl substituent, such as, for example, benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, 1,3,4-thiadiazolyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, phthalazinyl, quinoxalinyl, cinnolinyl, napthyridinyl, pyridazinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl and the like.

"$C_1$-$C_6$-alkyl heteroaryl" refers to $C_1$-$C_6$-alkyl groups having a heteroaryl substituent, such as, for example, 2-furylmethyl, 2-thienylmethyl, 2-(1H-indol-3-yl)ethyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_3$-$C_8$-heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"$C_2$-$C_6$-alkenyl" refers to alkenyl groups preferably having from 2 to 6 carbon atoms and having one or more sites of alkenyl unsaturation. Preferred alkenyl groups include ethenyl (—CH=$CH_2$), n-2-propenyl (allyl, —$CH_2$CH=$CH_2$) and the like.

"$C_2$-$C_6$-alkynyl" refers to alkynyl groups preferably having from 2 to 6 carbon atoms and having one or more sites of alkynyl unsaturation. Preferred alkynyl groups include ethynyl (—C≡CH), propynyl (—$CH_2$C≡CH), and the like.

"Carboxy refers to the group —C(O)OR, where R includes hydrogen or "$C_1$-$C_6$-alkyl".

"Acyl" refers to the group —C(O)R where R includes "$C_1$-$C_6$-alkyl", "aryl", "heteroaryl", "$C_3$-$C_8$-cycloalkyl", "$C_3$-$C_8$-heterocycloalkyl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "hetero-aryl", "$C_1$-$C_6$-alkyl aryl" or "$C_1$-$C_6$-alkyl heteroaryl".

"Aryl acyl" refers to aryl groups having an acyl substituent, including 2-acetylphenyl and the like.

"Heteroaryl acyl" refers to heteroaryl groups having an acyl substituent, including 2-acetylpyridyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred alkoxy groups include by way of example, methoxy, ethoxy, phenoxy and the like.

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl hetero-aryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyloxy" refers to a group —$OSO_2$—R wherein R is selected from H, "$C_1$-$C_6$-alkyl", "$C_1$-$C_6$-alkyl" substituted with halogens, e.g., an —$OSO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfinyl" refers to a group "—S(O)—R" wherein R is selected from H, "$C_1$-$C_6$-alkyl", "$C_1$-$C_6$-alkyl" substituted with halogens, e.g., an —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfanyl" refers to groups —S—R where R includes H, "$C_1$-$C_6$-alkyl", "$C_1$-$C_6$-alkyl" optionally substituted with halogens, e.g a —S—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl"

or "C₁-C₆-alkyl heteroaryl", "C₂-C₆-alkenyl aryl", "C₂-C₆-alkenyl heteroaryl", "C₂-C₆-alkynyl aryl", "C₂-C₆-alkynylheteroaryl", "C₁-C₆-alkyl cycloalkyl", "C₁-C₆-alkyl heterocycloalkyl".

"Amino" refers to the group —NRR' where each R, R' is independently hydrogen, "C₁-C₆-alkyl", "C₂-C₆-alkenyl", "C₂-C₆-alkynyl", "C₃-C₈-cycloalkyl", "heterocycloalkyl", "aryl", "heteroaryl", "C₁-C₆-alkyl aryl" or "C₁-C₆-alkyl heteroaryl", "C₂-C₆-alkenyl aryl", "C₂-C₆-alkenyl heteroaryl", "C₂-C₆-alkynyl aryl", "C₂-C₆-alkynylheteroaryl", "C₁-C₆-alkyl cycloalkyl", "C₁-C₆-alkyl heterocycloalkyl", and where R and R', together with the nitrogen atom to which they are attached, can optionally form a 3-8-membered hetero-cycloalkyl ring.

"Substituted or unsubstituted": Unless otherwise constrained by the definition of the individual substituent, the above set out groups, like "alkyl", "alkenyl", "alkynyl", "alkoxy", "aryl" and "heteroaryl" etc. groups can optionally be substituted with from 1 to 5 substituents selected from the group consisting of "C₁-C₆-alkyl", "C₁-C₆-alkyl aryl", "C₁-C₆-alkyl heteroaryl", "C₂-C₆-alkenyl", "C₂-C₆-alkynyl", primary, secondary or tertiary amino groups or quaternary ammonium moieties, "acyl", "acyloxy", "acylamino", "aminocarbonyl", "alkoxycarbonyl", "aryl", "aryloxy", "heteroaryl", "heteroaryloxy", carboxyl, cyano, halogen, hydroxy, nitro, sulfanyl, sulphooxy, sulphonyl, sulfonamide, alkoxy, thioalkoxy, trihalomethyl and the like. Within the framework of this invention, said "substitution" is meant to also comprise situations where neighboring substituents undergo ring closure, in particular when vicinal functional substituents are involved, thus forming e.g. lactams, lactons, cyclic anhydrides, but also acetals, thioacetals, animals formed by ring closure for instance in an effort to obtain a protective group.

"Pharmaceutically acceptable cationic salts or complexes" is intended to define such salts as the alkali metal salts, (e.g. sodium and potassium), alkaline earth metal salts (e.g. calcium or magnesium), aluminium salts, ammonium salts and salts with organic amines such as with methylamine, dimethylamine, trimethylamine, ethylamine, triethylamine, morpholine, N-Me-D-glucamine, N,N'-bis(phenylmethyl)-1,2-ethanediamine, ethanolamine, diethanolamine, ethylenediamine, N-methylmorpholine, piperidine, benzathine (N,N'-dibenzylethylenediamine), choline, ethylene-diamine, meglumine (N-methylglucamine), benethamine (N-benzylphenethylamine), diethylamine, piperazine, thromethamine (2-amino-2-hydroxymethyl-1,3-propanediol), procaine as well as amines of formula —NR,R',R" wherein R, R', R" is independently hydrogen, alkyl or benzyl. Especially preferred salts are sodium and potassium salts.

"Pharmaceutically acceptable salts or complexes" refers to salts or complexes of the below-identified compounds of Formula I that retain the desired biological activity. Examples of such salts include, but are not restricted to, acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quaternary ammonium salt of the Formula —NR, R',R"⁺Z⁻, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that, upon administration to the recipient, is capable of providing directly or indirectly, the activity disclosed herein.

The compounds of the present invention according to Formula I are useful in the treatment and/or prevention of diseases selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropatic pain, and other inflammatory diseases such as rheumatoid arthritis, multiple sclerosis, osteoarthritis, and inflammatory bowel disease (IBD).

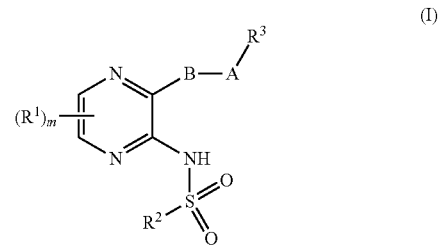

(I)

In one embodiment the compounds according to Formula (I) are suitable as modulators, notably as antagonists, of CRTH2. Therefore, the compounds of the present invention are also particularly useful for the treatment and/or prevention of disorders, which are mediated by CRTH2 activity. Said treatment involves the modulation of CRTH2, notably an inhibition of CRTH2 or an antagonizing effect of CRTH2 in mammals, and in particular in humans. The modulators of CRTH2 are selected from the group consisting of an antagonist, an inverse agonist, a partial agonist and an agonist of CRTH2.

In another embodiment, the modulators of CRTH2 are antagonists of CRTH2.

In one embodiment, the modulators of CRTH2 are inverse agonists of CRTH2.

In another embodiment, the modulators of CRTH2 are partial agonists of CRTH2.

In another embodiment, the modulators of CRTH2 are agonists of CRTH2.

The compounds according to Formula (I) are suitable for use as a medicament.

Compounds of Formula (I) include also their geometrical isomers, their optically active forms as enantiomers, diastereomers, its racemate forms and tautomers, as well as pharmaceutically acceptable salts thereof, wherein:

A is either an amine selected from the group consisting of:

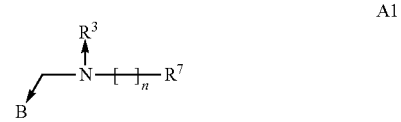

A1

-continued $$\text{B} \diagdown \text{N} - [\phantom{x}]_n - \text{R}^7 \diagup \text{R}^3 \quad \text{A2}$$

$$\text{B} \leftarrow \text{N} - [\phantom{x}]_n - \text{R}^7 \quad \uparrow \text{R}^3 \quad \text{A3}$$

$$\leftarrow \text{N} - [\phantom{x}]_n - \text{R}^7 \diagup \text{R}^3 \quad \text{A4}$$

or an alkyl, acyl, amino carbonyl or ether selected from the group consisting of:

$$\text{B} \leftarrow (\text{CH}_2)n \rightarrow \text{R}^3 \quad \text{A5}$$

$$\text{B} \leftarrow \overset{O}{\underset{\|}{C}} - \text{R}^3 \quad \text{A6}$$

$$\text{B} \leftarrow \overset{O}{\underset{\|}{C}} - \text{N} - [\phantom{x}]_n \overset{\text{R}^8}{\phantom{X}} \quad \text{A7}$$

$$\text{B} \leftarrow [\phantom{x}]_n - \text{O} - [\phantom{x}]_n \rightarrow \text{R}^3 \quad \text{A8}$$

with each n being an integer independently selected from 0, 1, 2, 3 or 4;
m is either 1 or 2;
wherein, $R^7$ is selected from the group consisting of hydrogen, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted aryl, substituted or unsubstituted heteroaryl, substituted or unsubstituted $C_3$-$C_8$-cycloalkyl, substituted or unsubstituted $C_3$-$C_8$-heterocycloalkyl, carboxyl, cyano, amino and hydroxyl.
$R^8$ is selected from the group consisting of hydrogen, substituted or unsubstituted $C_1$-$C_6$-alkyl, substituted or unsubstituted aryl, and substituted or unsubstituted heteroaryl.
B is selected from the group consisting of a substituted or unsubstituted $C_2$-$C_6$-alkynyl, substituted or unsubstituted $C_3$-$C_8$-cycloalkyl, substituted or unsubstituted $C_3$-$C_8$-heterocycloalkyl, substituted or unsubstituted aryl, and substituted or unsubstituted monocyclic heteroaryl.

Examples of B include ethynyl, propynyl, cyclopropyl, cyclobutyl, cyclopentyl, cyclohexyl, cycloheptyl, cyclooctyl, pyrrolidinyl, pyrazolidinyl, piperidinyl, piperazinyl, pyridyl, imidazolidinyl, 1,2,4-oxadiazolidinyl, 1,2,5-oxadiazolidinyl, 1,3,4-oxadiazolidinyl, isoxazolidinyl, morpholinyl, phenyl, naphthyl, pyrrolyl, pyrimidyl, furyl, thienyl, imidazolyl, oxazolyl, isoxazolyl, thiazolyl, isothiazolyl, carbazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, tetrazolyl, 1,3,4-triazinyl, 1,2,3-triazinyl, oxolanyl, pyrrolidinyl, pyrazolidinyl, piperidinyl, piperazinyl.

According to one embodiment, B is selected from the group of a substituted or unsubstituted aryl, a substituted or unsubstituted $C_3$-$C_8$-heterocycloalkyl and a substituted or unsubstituted alkynyl.

According to one embodiment, B is a substituted or unsubstituted aryl group (e.g. phenyl). According to another embodiment said phenyl group is mono-substituted in ortho, meta or para position.

In another embodiment, B is a $C_3$-$C_8$-heterocycloalkyl group (e.g. piperazinyl, furyl or thienyl).

According to another embodiment, B is an alkynyl group (e.g. ethynyl or propynyl).

$R^1$ is either hydrogen or a substituted or unsubstituted $C_1$-$C_6$-alkyl. In a preferred embodiment $R^1$ is hydrogen.

$R^2$ is selected from the group consisting of substituted or unsubstituted $C_1$-$C_6$-alkyl, substituted or unsubstituted aryl, and substituted or unsubstituted heteroaryl, substituted or unsubstituted $C_3$-$C_8$-cycloalkyl and substituted or unsubstituted $C_3$-$C_8$ heterocycloalkyl.

Examples of $R^2$ include methyl, ethyl, propyl, t-butyl, cyclopropyl, cyclobutyl, cyclopentyl, cyclohexyl, cycloheptyl, cyclooctyl, pyrrolidinyl, pyrazolidinyl, piperidinyl, piperazinyl, pyridyl, imidazolidinyl, 1,2,4-oxadiazolidinyl, 1,2,5-oxadiazolidinyl, 1,3,4-oxadiazolidinyl, isoxazolidinyl or morpholinyl, phenyl, naphthyl, pyrrolyl, pyrimidyl, quinolizinyl, furyl, thienyl, imidazolyl, oxazolyl, isoxazolyl, thiazolyl, isothiazolyl, carbazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, tetrazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, oxolanyl, pyrrolidinyl, pyrazolidinyl, piperidinyl, piperazinyl, pyridyl, imidazolidinyl, 1,2,4-oxadiazolidinyl, 1,2,5-oxadiazolidinyl, 1,3,4-oxadiazolidinyl, isoxazolidinyl, quinazolinyl, phthalazinyl, quinoxalinyl, cinnolinyl, napthyridinyl, quinolyl, isoquinolyl, tetrazolyl, 5,6,7,8-tetrahydroquinolyl, 5,6,7,8-tetrahydroisoquinolyl, purinyl, pteridinyl, xanthenyl or benzoquinolyl.

According to one embodiment, $R^2$ is a substituted or unsubstituted aryl group (e.g. phenyl).

The substituents in a substituted $R^2$ are selected from the group consisting of halogen, cyano, $C_1$-$C_6$-alkyl, $C_1$-$C_6$-alkoxy, thioalkoxy and thioalkyl.

In one embodiment $R^2$ is optionally substituted with one or more substituents selected from the group consisting of halogen, cyano, $C_1$-$C_6$-alkyl, $C_1$-$C_6$-alkoxy, thioalkoxy and thioalkyl.

According to another embodiment, $R^2$ is substituted in ortho, meta or para position. In one embodiment, $R^2$ is chlorophenyl.

According to another embodiment, $R^2$ is substituted or unsubstituted heteroaryl group (e.g. pyridinyl or thienyl).

According to another embodiment, $R^2$ is a substituted or unsubstituted $C_1$-$C_6$-alkyl group (e.g. methyl).

$R^3$ is selected from the group consisting of a substituted or unsubstituted $C_1$-$C_6$-alkyl, substituted or unsubstituted aryl, substituted or unsubstituted heteroaryl, substituted or unsubstituted $C_3$-$C_8$-cycloalkyl and substituted or unsubstituted $C_3$-$C_8$-heterocycloalkyl; wherein said substituted or unsubstituted aryl, heteroaryl, $C_3$-$C_8$-cycloalkyl or $C_3$-$C_8$-heterocycloalkyl may be fused to one or more substituted or unsubstituted aryl, heteroaryl, $C_3$-$C_8$-cycloalkyl or $C_3$-$C_8$-heterocycloalkyl group and may be substituted with one or more substituents selected of the group consisting of $C_1$-$C_6$-alkyl, alkoxy, aryl, heteroaryl, carboxyl, cyano, halogen, hydroxy, amino, amino carbonyl, nitro, sulfoxy, sulfonyl, sulfonamide and trihalo-$C_1$-$C_6$-alkyl.

Examples of $R^3$ include methyl, ethyl, propyl, butyl, t-butyl, phenyl, naphthyl, phenanthrenyl, pyrrolyl, furyl, thienyl, imidazolyl, oxazolyl, isoxazolyl, thiazolyl, isothiazolyl, pyrazolyl, carbazolyl, 1,2,3-triazolyl, 1,2,4-triazolyl, 1,2,3-oxadiazolyl, benzo(2,1,3)oxadiazolyl, benzo(1,2,5)oxadiazolyl, benzo[1,3]dioxole, 1,2,4-oxadiazolyl, 1,2,5-oxadiazolyl, 1,3,4-oxadiazolyl, tetrazolyl, 1,3,4-triazinyl, 1,2,3-triazinyl, benzofuryl, [2,3-dihydro]benzofuryl, 3,4-dihydro-1H-benzo[1,4]diazepine-2,5-dione, isobenzofuryl, benzothienyl, benzotriazolyl, isobenzothienyl, indolyl, isoindolyl, 3H-indolyl, benzimidazolyl, benzothiazolyl, benzoxazolyl, pyridazinyl, pyrimidyl, quinolizinyl, quinazolinyl, phthalazinyl, quinoxalinyl, cinnolinyl, napthyridinyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, cyclopropyl, cyclobutyl, cyclopentyl, cyclohexyl, cycloheptyl, cyclooctyl, oxolanyl, pyrrolidinyl, pyrazolidinyl, piperidinyl, piperazinyl, pyridyl, imidazolidinyl, 1,2,4-oxadiazolidinyl, 1,2,5-oxadiazolidinyl, 1,3,4-oxadiazolidinyl, isoxazolidinyl or morpholinyl.

According to one embodiment, $R^3$ is a substituted or unsubstituted aryl group (e.g. phenyl or naphthyl). The substituents in a substituted $R^3$ are selected from the group consisting of halogen, cyano, $C_1$-$C_6$-alkyl, $C_1$-$C_6$-alkoxy, heteroaryl, aryl, thioalkoxy and thioalkyl.

In one embodiment $R^3$ is optionally substituted with one or more substituents selected from the group consisting of halogen, cyano, $C_1$-$C_6$-alkyl, $C_1$-$C_6$-alkoxy, heteroaryl, aryl, thioalkoxy and thioalkyl.

Examples for a substituted phenyl moiety are 4-trifluoromethoxyphenyl, 3-methoxyphenyl, 4-chlorophenyl, 3,5-dimethylphenyl, 2-benzamide or 2-benzoic acid.

In another embodiment, $R^3$ is a substituted or unsubstituted heteroaryl group (e.g. pyridyl, quinolyl, benzimidazolyl, indolyl, pyridazinyl, pyrazinyl or 1,3,4-thiadiazolyl). An example for a substituted benzimidazole is 2-ethyl-2H-benzimidazolyl.

In another embodiment, $R^3$ is an aryl group fused to a $C_3$-$C_8$-heterocycloalkyl group (e.g. 1,3-dihydrobenzimidazole-2-one, 3,4-dihydro1H-benzo[1,4]diazepine-2,5-dione).

In another embodiment, $R^3$ is a substituted or unsubstituted $C_3$-$C_8$-heterocycylalkyl group fused to a substituted or unsubstituted aryl group (e.g. 1,2,3,4-tetrahydrochinoline, 1,2,3,4-tetrahydrochinoxaline, 2,3-dehydrobenzol, 4-oxazine, 2,3-dehydro-indole or dihydrobenzo-pyrrolodiazepine).

In another embodiment, $R^3$ is a substituted or unsubstituted $C_3$-$C_8$-heterocycylalkyl group fused to a substituted or unsubstituted aryl group and to a substituted or unsubstituted heteroaryl group (e.g. dihydrobenzopyrrolodiazepine).

In another embodiment, $R^3$ is a substituted or unsubstituted alkyl group (e.g. isopropyl).

According to another embodiment, the substituents at $R^2$ or $R^3$ are selected from the group consisting of $C_1$-$C_6$-alkyl, alkoxy, cyano, amino and halogen (e.g. methyl, ethyl, butyl, tert.-butyl, methoxy, ethoxy, tert.-butoxy, phenoxy, chloro, fluoro); wherein alkyl, alkoxy or aryloxy are optionally substituted with halogen (e.g. trifluoromethyl, trifluoromethoxy);

as well as isomers and mixtures of these for use as a medicament.

Another specific sub-group of formula (I) are compounds having formula (I'), whereby A, B, $R^2$ and $R^3$ are defined as above and each $R^1$ can be independently hydrogen or substituted or unsubstituted $C_1$-$C_6$-alkyl.

In a preferred embodiment, $R^1$ is hydrogen.

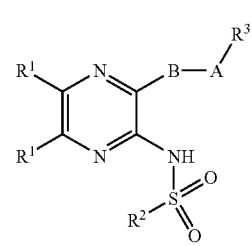

(I')

A specific sub-group of formulae (I) and (I') are compounds having the formulae (Ia-Id), whereby A, $R^2$ and $R^3$ are defined as above and Z is O or S.

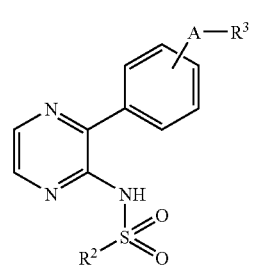

(Ia)

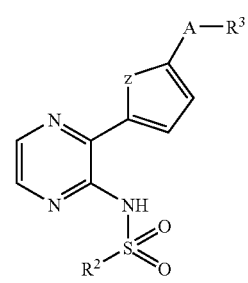

(Ib)

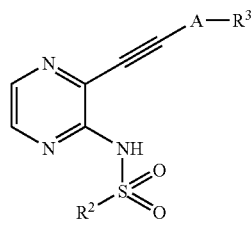

(Ic)

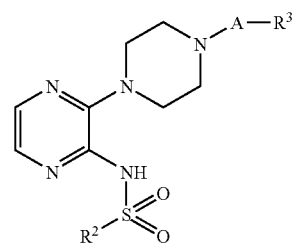

(Id)

Preferred pharmaceutically acceptable salts of compounds of Formula I, and compounds of sub-groups of Formulae (Ia)-(Id) containing a basic residue such as, for example, a primary, secondary, or tertiary amine or a pyridyl moiety, are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methane-sulfonate, benzenesulfonate, and para-toluene-sulfonate salts.

Compounds of the present invention that are particularly suitable for use as a medicament, include in particular those of the group consisting of:

| Example No. | Name |
|---|---|
| 1 | N-{3-[4-(1H-indol-1-ylmethyl)phenyl]pyrazin-2-yl}-2-(trifluoromethyl)benzenesulfonamide |
| 2 | 2-chloro-N-{3-[4-({methyl[4-(trifluoromethoxy)phenyl]amino}-methyl)phenyl]pyrazin-2-yl}benzenesulfonamide |
| 3 | N-(3-{4-[(2-ethyl-1H-benzimidazol-1-yl)methyl]phenyl}pyrazin-2-yl)-2-(trifluoromethyl)benzenesulfonamide |
| 4 | 2-chloro-N-[3-(4-{[methyl(phenyl)amino]methyl}phenyl)pyrazin-2-yl]benzenesulfonamide |
| 5 | 2-chloro-N-(3-{4-[(2-naphthyloxy)methyl]phenyl}pyrazin-2-yl)-benzenesulfonamide |
| 6 | 2-chloro-N-{3-[4-(1H-indol-1-ylmethyl)phenyl]pyrazin-2-yl}-+benzenesulfonamide |
| 7 | 2-chloro-N-(3-{4-[(5,6,7,8-tetrahydronaphthalen-2-yloxy)methyl]-phenyl}pyrazin-2-yl)benzenesulfonamide |
| 8 | 2-chloro-N-(3-{4-[(2-ethyl-1H-benzimidazol-1-yl)methyl]phenyl}pyrazin-2-yl)benzenesulfonamide |
| 9 | N-(3-{4-[(1,3-benzodioxol-5-ylamino)methyl]phenyl}pyrazin-2-yl)-2-(trifluoromethyl)benzenesulfonamide |
| 10 | N-[3-(4-{[(3-methoxybenzyl)oxy]methyl}phenyl)pyrazin-2-yl]-2-(trifluoromethyl)benzenesulfonamide |
| 11 | 3-chloro-N-{3-[4-({methyl[4-(trifluoromethoxy)phenyl]amino}-methyl)phenyl]pyrazin-2-yl}benzenesulfonamide |
| 12 | N-[3-(4-{[(4-chlorophenyl)(methyl)amino]methyl}phenyl)pyrazin-2-yl]-thiophene-2-sulfonamide |
| 13 | 4-phenoxy-N-{3-[4-(quinolin-2-ylmethyl)piperazin-1-yl]pyrazin-2-yl}-benzenesulfonamide |
| 14 | 4-methyl-N-{3-[4-({methyl[4-(trifluoromethoxy)phenyl]amino}-methyl)phenyl]pyrazin-2-yl}benzenesulfonamide |
| 15 | 4-chloro-N-[3-(4-{[methyl(phenyl)amino]methyl}phenyl)pyrazin-2-yl]-benzenesulfonamide |
| 16 | 4-cyano-N-{3-[4-({methyl[4-(trifluoromethoxy)phenyl]-amino}-methyl)phenyl]pyrazin-2-yl}benzenesulfonamide |
| 17 | N-[3-(4-{[(4-Fluoro-phenyl)-methyl-amino]-methyl}-phenyl)-pyrazin-2-yl]-2-trifluoromethyl-benzenesulfonamide |
| 18 | N-(3-{4-[(Methyl-phenyl-amino)-methyl]-phenyl}-pyrazin-2-yl)-2-trifluoromethyl-benzenesulfonamide |
| 19 | N-[3-(4-{[(4-Cyano-phenyl)-methyl-amino]-methyl}-phenyl)-pyrazin-2-yl]-2-trifluoromethyl-benzenesulfonamide |
| 20 | N-{3-[4-(4-Fluoro-phenoxymethyl)-phenyl]-pyrazin-2-yl}-2-trifluoromethyl-benzenesulfonamide |
| 21 | N-(3-{4-[(Ethyl-phenyl-amino)-methyl]-phenyl}-pyrazin-2-yl)-2-trifluoromethyl-benzenesulfonamide |
| 22 | N-{3-[4-(2,3-Dihydro-benzo[1,4]oxazin-4-ylmethyl)-phenyl]-pyrazin-2-yl}-2-trifluoromethyl-benzenesulfonamide |
| 23 | N-[3-(4-{[(3-Fluoro-phenyl)-methyl-amino]-methyl}-phenyl)-pyrazin-2-yl]-2-trifluoromethyl-benzenesulfonamide |
| 24 | N-{3-[4-(6-Chloro-pyridin-3-yloxymethyl)-phenyl]-pyrazin-2-yl}-2-trifluoromethyl-benzenesulfonamide |
| 25 | N-{3-[4-(2-Pyridin-2-yl-indol-1-ylmethyl)-phenyl]-pyrazin-2-yl}-2-trifluoromethyl-benzenesulfonamide |
| 26 | N-{3-[4-(5-Fluoro-indol-1-ylmethyl)-phenyl]-pyrazin-2-yl}-2-trifluoromethyl-benzenesulfonamide |
| 27 | N-[3-(4-Phenoxymethyl-phenyl)-pyrazin-2-yl]-2-trifluoromethyl-benzenesulfonamide |
| 28 | N-[3-(4-{[(4-Chloro-phenyl)-methyl-amino]-methyl}-phenyl)-pyrazin-2-yl]-2-trifluoromethyl-benzenesulfonamide |
| 29 | 2-Chloro-N-[3-(4-{[(4-cyano-phenyl)-methyl-amino]-methyl}-phenyl)-pyrazin-2-yl]-benzenesulfonamide |
| 30 | N-[3-(4-{[(3,4-Dichloro-phenyl)-methyl-amino]-methyl}-phenyl)-pyrazin-2-yl]-2-trifluoromethyl-benzenesulfonamide |
| 31 | N-{3-[4-(4-Cyano-phenoxymethyl)-phenyl]-pyrazin-2-yl}-2-trifluoromethyl-benzenesulfonamide |
| 32 | N-{3-[4-(6-Fluoro-indol-1-ylmethyl)-phenyl]-pyrazin-2-yl}-2-trifluoromethyl-benzenesulfonamide |
| 33 | 2-Chloro-N-{3-[4-(5-methoxy-2-methyl-indol-1-ylmethyl)-phenyl]-pyrazin-2-yl}-benzenesulfonamide |
| 34 | N-{3-[4-(4-Methoxy-phenoxymethyl)-phenyl]-pyrazin-2-yl}-2-trifluoromethyl-benzenesulfonamide |
| 35 | N-(3-{4-[(Benzyl-pyridin-2-yl-amino)-methyl]-phenyl}-pyrazin-2-yl)-2-chloro-benzenesulfonamide |
| 36 | N-{3-[4-(2,3-Dihydro-indol-1-ylmethyl)-phenyl]-pyrazin-2-yl}-2-trifluoromethyl-benzenesulfonamide |

-continued

| Example No. | Name |
|---|---|
| 37 | N-[3-(4-{[(2,4-Dichloro-phenyl)-methyl-amino]-methyl}-phenyl)-pyrazin-2-yl]-2-trifluoromethyl-benzenesulfonamide |
| 38 | N-{3-[4-(3-Chloro-phenoxymethyl)-phenyl]-pyrazin-2-yl}-2-trifluoromethyl-benzenesulfonamide |
| 39 | 2-Chloro-N-[3-(4-{[(2,4-difluoro-phenyl)-methyl-amino]-methyl}-phenyl)-pyrazin-2-yl]-benzenesulfonamide |
| 40 | N-{3-[4-(2-Methyl-indol-1-ylmethyl)-phenyl]-pyrazin-2-yl}-2-trifluoromethyl-benzenesulfonamide |
| 41 | 2-Chloro-N-{3-[4-(5-fluoro-indol-1-ylmethyl)-phenyl]-pyrazin-2-yl}-benzenesulfonamide |
| 42 | 2-Chloro-N-[3-(4-{[(2-fluoro-phenyl)-methyl-amino]-methyl}-phenyl)-pyrazin-2-yl]-benzenesulfonamide |
| 43 | 2-Chloro-N-{3-[4-(2-methyl-indol-1-ylmethyl)-phenyl]-pyrazin-2-yl}-benzenesulfonamide |
| 44 | N-(3-{4-[(Benzyl-pyridin-2-yl-amino)-methyl]-phenyl}-pyrazin-2-yl)-2-trifluoromethyl-benzenesulfonamide |
| 45 | 2-Chloro-N-(3-{4-[(ethyl-pyridin-2-yl-amino)-methyl]-phenyl}-pyrazin-2-yl)-benzenesulfonamide |
| 46 | N-{3-[4-(5-Chloro-2-methyl-indol-1-ylmethyl)-phenyl]-pyrazin-2-yl}-2-trifluoromethyl-benzenesulfonamide |

In a second aspect, the invention provides a pharmaceutical composition comprising a 2,3 substituted pyrazine sulfonamide according to Formula (I), together with a pharmaceutically acceptable excipient or carrier.

In a third aspect, the invention provides the use of a 2,3 substituted pyrazine sulfonamide according to formulae (I) for the preparation of a medicament for the treatment and/or prevention of a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis and other diseases with an inflammatory component such as rheumatoid arthritis, osteoarthritis, and inflammatory bowel disease (IBD) and other diseases and disorders associated with CTRH2 activity.

In a forth aspect, the invention provides a method for treating and/or preventing a patient suffering from a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropatic pain, and other inflammatory diseases such as rheumatoid arthritis, multiple sclerosis, osteoarthritis, and inflammatory bowel disease (IBD) and other diseases and disorders associated with CTRH2 activity, by administering a 2,3 substituted pyrazine sulfonamide according to Formula (I).

The term "preventing", as used herein, should be understood as partially or totally preventing, inhibiting, alleviating, or reversing one or more symptoms or cause(s) of allergic disease or inflammatory dermatitis.

In a fifth aspect, the invention provides the use of a 2,3 substituted pyrazine sulfonamide of Formula (I) for the preparation of a pharmaceutical composition useful for a variety of therapies, including preventing and/or treating a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropatic pain, and other inflammatory diseases such as rheumatoid arthritis, multiple sclerosis, osteoarthritis, and inflammatory bowel disease (IBD) and other diseases and disorders associated with CTRH2 activity.

The invention provides further the use of a 2,3 substituted pyrazine sulfonamide of Formula (I) for preventing and/or treating a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropatic pain, and other inflammatory diseases such as rheumatoid arthritis, multiple sclerosis, osteoarthritis, and inflammatory bowel disease (IBD) and other diseases and disorders associated with CTRH2 activity.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

The compounds according to Formula (I) of the present invention are typically administered in form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the substituted methylene amide derivative according to the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate buffered saline or other injectable carriers known in the art. As above mentioned, substituted methylene amide derivatives of Formula (I) in such compositions is typically a minor component, frequently ranging between 0.05 to 10% by weight with the remainder being the injectable carrier and the like.

The above-described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In a sixth aspect, the invention provides novel 2,3-substituted pyrazine sulfonamides of Formulae (Ia)-(Id) wherein A, $R^2$, and $R^3$ are defined as described above. Novel compounds of Formulae (Ia)-(Id) are in particular those of the group consisting of:

N-{3-[4-(1H-indol-1-ylmethyl)phenyl]pyrazin-2-yl}-2-(trifluoromethyl)benzenesulfonamide,
2-chloro-N-{3-[4-({methyl[4-(trifluoromethoxy)phenyl]amino}-methyl)phenyl]pyrazin-2-yl}benzene sulfonamide,
N-(3-{4-[(2-ethyl-1H-benzimidazol-1-yl)methyl]phenyl}pyrazin-2-yl)-2-(trifluoromethyl)benzenesulfonamide,
2-chloro-N-[3-(4-{[methyl(phenyl)amino]methyl}phenyl)pyrazin-2-yl]benzenesulfonamide,
2-chloro-N-(3-{4-[(2-naphthyloxy)methyl]phenyl}pyrazin-2-yl)-benzenesulfonamide,
2-chloro-N-{3-[4-(1H-indol-1-ylmethyl)phenyl]pyrazin-2-yl}-+benzenesulfonamide,
2-chloro-N-(3-{4-[(5,6,7,8-tetrahydronaphthalen-2-yloxy)methyl]-phenyl}pyrazin-2-yl)benzenesulfonamide,
2-chloro-N-(3-{4-[(2-ethyl-1H-benzimidazol-1-yl)methyl]phenyl}pyrazin-2-yl)benzenesulfonamide,
N-(3-{4-[(1,3-benzodioxol-5-ylamino)methyl]phenyl}pyrazin-2-yl)-2-(trifluoromethyl)benzenesulfonamide,
N-[3-(4-{[(3-methoxybenzyl)oxy]methyl}phenyl)pyrazin-2-yl]-2-(trifluoromethyl)benzenesulfonamide,
3-chloro-N-{3-[4-({methyl[4-(trifluoromethoxy)phenyl]amino}-methyl)phenyl]pyrazin-2-yl}benzenesulfonamide,
N-[3-(4-{[(4-chlorophenyl)(methyl)amino]methyl}phenyl)pyrazin-2-yl]-thiophene-2-sulfonamide,
4-phenoxy-N-{3-[4-(quinolin-2-ylmethyl)piperazin-1-yl]pyrazin-2-yl}-benzenesulfonamide,
4-methyl-N-{3-[4-({methyl[4-(trifluoromethoxy)phenyl]amino}-methyl)phenyl]pyrazin-2-yl}benzenesulfonamide,
4-chloro-N-[3-(4-{[methyl(phenyl)amino]methyl}phenyl)pyrazin-2-yl]-benzenesulfonamide,
4-cyano-N-{3-[4-({methyl[4-(trifluoromethoxy)phenyl]-amino}-methyl)phenyl]pyrazin-2-yl}benzenesulfonamide,
N-[3-(4-{[(4-Fluoro-phenyl)-methyl-amino]-methyl}-phenyl)-pyrazin-2-yl]-2-trifluoromethyl-benzenesulfonamide,
N-(3-{4-[(Methyl-phenyl-amino)-methyl]-phenyl}-pyrazin-2-yl)-2-trifluoromethyl-benzenesulfonamide,
N-[3-(4-{[(4-Cyano-phenyl)-methyl-amino]-methyl}-phenyl)-pyrazin-2-yl]-2-trifluoromethyl-benzenesulfonamide,
N-{3-[4-(4-Fluoro-phenoxymethyl)-phenyl]-pyrazin-2-yl}-2-trifluoromethyl-benzenesulfonamide,
N-(3-{4-[(Ethyl-phenyl-amino)-methyl]-phenyl}-pyrazin-2-yl)-2-trifluoromethyl-benzenesulfonamide,
N-{3-[4-(2,3-Dihydro-benzo[1,4]oxazin-4-ylmethyl)-phenyl]-pyrazin-2-yl}-2-trifluoromethyl-benzenesulfonamide,
N-[3-(4-{[(3-Fluoro-phenyl)-methyl-amino]-methyl}-phenyl)-pyrazin-2-yl]-2-trifluoromethyl-benzenesulfonamide,
N-{3-[4-(6-Chloro-pyridin-3-yloxymethyl)-phenyl]-pyrazin-2-yl}-2-trifluoromethyl-benzenesulfonamide,
N-{3-[4-(2-Pyridin-2-yl-indol-1-ylmethyl)-phenyl]-pyrazin-2-yl}-2-trifluoromethyl-benzenesulfonamide,
N-{3-[4-(5-Fluoro-indol-1-ylmethyl)-phenyl]-pyrazin-2-yl}-2-trifluoromethyl-benzenesulfonamide,
N-[3-(4-Phenoxymethyl-phenyl)-pyrazin-2-yl]-2-trifluoromethyl-benzenesulfonamide,
N-[3-(4-{[(4-Chloro-phenyl)-methyl-amino]-methyl}-phenyl)-pyrazin-2-yl]-2-trifluoromethyl-benzenesulfonamide,
2-Chloro-N-[3-(4-{[(4-cyano-phenyl)-methyl-amino]-methyl}-phenyl)-pyrazin-2-yl]-benzenesulfonamide,
N-[3-(4-{[(3,4-Dichloro-phenyl)-methyl-amino]-methyl}-phenyl)-pyrazin-2-yl]-2-trifluoromethyl-benzenesulfonamide,
N-{3-[4-(4-Cyano-phenoxymethyl)-phenyl]-pyrazin-2-yl}-2-trifluoromethyl-benzenesulfonamide,
N-{3-[4-(6-Fluoro-indol-1-ylmethyl)-phenyl]-pyrazin-2-yl}-2-trifluoromethyl-benzenesulfonamide,
2-Chloro-N-{3-[4-(5-methoxy-2-methyl-indol-1-ylmethyl)-phenyl]-pyrazin-2-yl}-benzenesulfonamide,
N-{3-[4-(4-Methoxy-phenoxymethyl)-phenyl]-pyrazin-2-yl}-2-trifluoromethyl-benzenesulfonamide,
N-(3-{4-[(Benzyl-pyridin-2-yl-amino)-methyl]-phenyl}-pyrazin-2-yl)-2-chloro-benzenesulfonamide, N-{3-[4-(2,3-Dihydro-indol-1-ylmethyl)-phenyl]-pyrazin-2-yl}-2-trifluoromethyl-benzenesulfonamide,
N-[3-(4-{[(2,4-Dichloro-phenyl)-methyl-amino]-methyl}-phenyl)-pyrazin-2-yl]-2-trifluoromethyl-benzenesulfonamide,
N-{3-[4-(3-Chloro-phenoxymethyl)-phenyl]-pyrazin-2-yl}-2-trifluoromethyl-benzenesulfonamide,
2-Chloro-N-[3-(4-{[(2,4-difluoro-phenyl)-methyl-amino]-methyl}-phenyl)-pyrazin-2-yl]-benzenesulfonamide,
N-{3-[4-(2-Methyl-indol-1-ylmethyl)-phenyl]-pyrazin-2-yl}-2-trifluoromethyl-benzenesulfonamide,
2-Chloro-N-{3-[4-(5-fluoro-indol-1-ylmethyl)-phenyl]-pyrazin-2-yl}-benzenesulfonamide,
2-Chloro-N-[3-(4-{[(2-fluoro-phenyl)-methyl-amino]-methyl}-phenyl)-pyrazin-2-yl]-benzenesulfonamide,
2-Chloro-N-{3-[4-(2-methyl-indol-1-ylmethyl)-phenyl]-pyrazin-2-yl}-benzenesulfonamide,
N-(3-{4-[(Benzyl-pyridin-2-yl-amino)-methyl]-phenyl}-pyrazin-2-yl)-2-trifluoromethyl-benzenesulfonamide,
2-Chloro-N-(3-{4-[(ethyl-pyridin-2-yl-amino)-methyl]-phenyl}-pyrazin-2-yl)-benzenesulfonamide, and
N-{3-[4-(5-Chloro-2-methyl-indol-1-ylmethyl)-phenyl]-pyrazin-2-yl}-2-trifluoromethyl-benzenesulfonamide.

In a seventh aspect, the invention provides a method of synthesis of a compound according to formula (Ia)-(Id).

The 2,3 substituted sulfonamides exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

A general description of methods for preparing compounds of Formula (I) is given in WO 04/058265 (PCT/GB03/005668).

The general synthetic approach for obtaining compounds of Formulae (Ia)-(Id) is depicted in Scheme 1. Therein, 2,3-substituted pyrazine sulfonamide derivatives according to the general formula I, may be prepared in 4 to 5 chemical steps, from commercially available 2,3-dichloropyrazine. Synthetic protocols are outlined in Schemes 1 to 10.

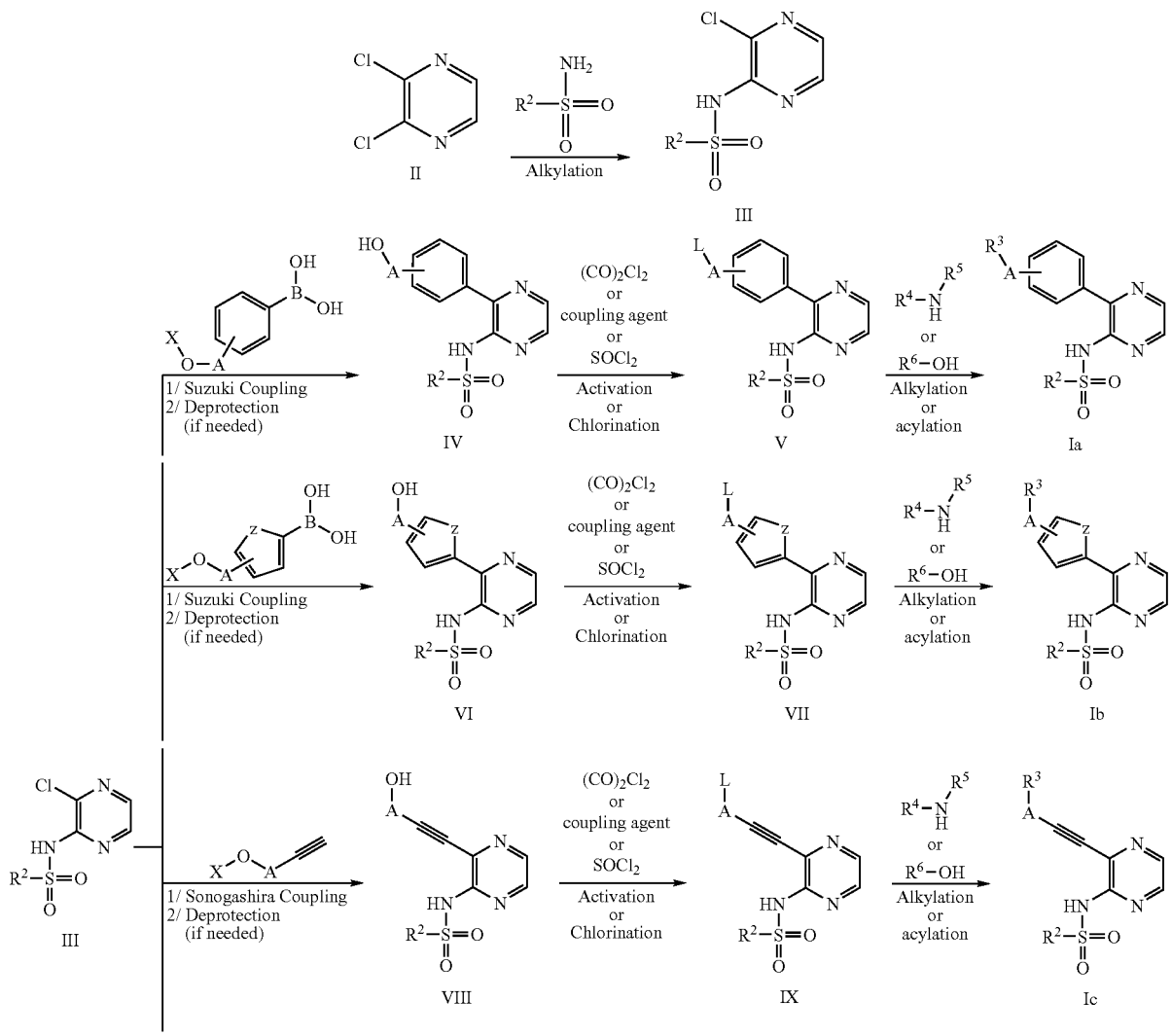

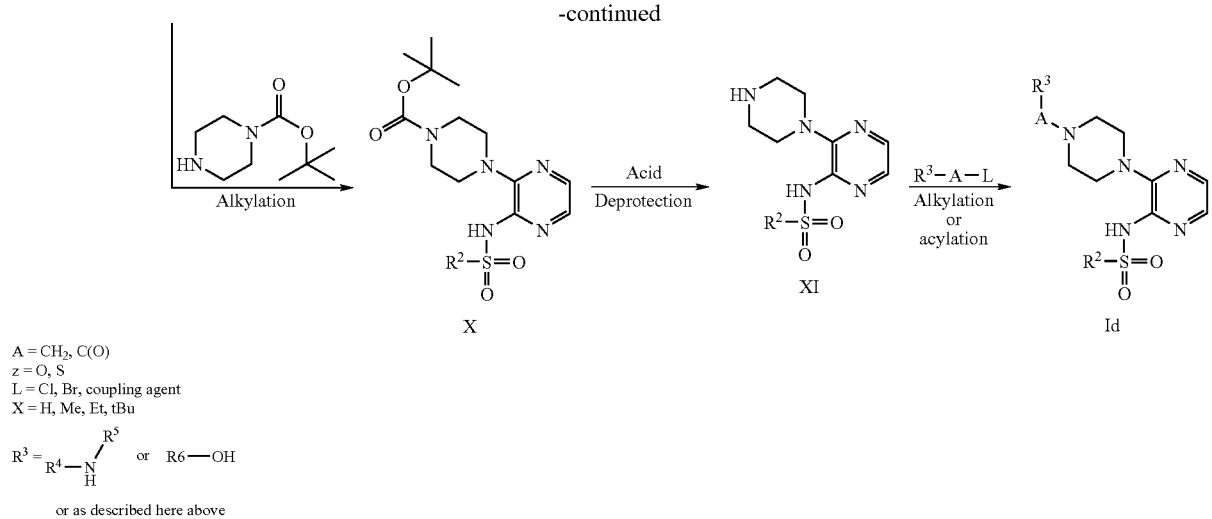

A = CH₂, C(O)
z = O, S
L = Cl, Br, coupling agent
X = H, Me, Et, tBu $R^3 = R^4 - N{\overset{R^5}{\underset{H}{\diagdown}}}$  or  R6—OH or as described here above In a more specific method, the sulfonamide derivatives XXI, wherein $R^2$ is defined as above is reacted with the 2,3-dichloropyrazine II to give the corresponding 3-chloropyrazine sulfonamide compounds III. Several reaction conditions may be utilized for performing this first reaction step, e.g. by the use of sulfonamide derivative XXI in presence of a base such as cesium carbonate, potassium carbonate or the like. This reaction may be performed in solvents like NMP, DMF or DMA at various temperature depending on the intrinsic reactivity of compounds XXI and II, by traditional thermic or microwave method, using standard conditions well known to the person skilled in the art or shown in Scheme 2, below:

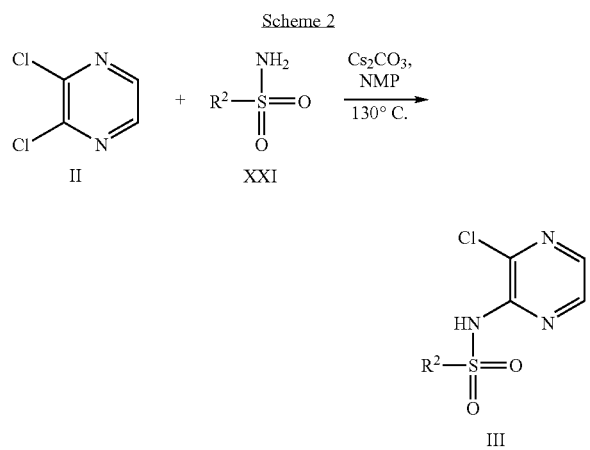

The sulfonamide derivatives XXI are obtained from commercial sources or can be prepared by treatment of the corresponding sulfonyl chlorides XX, using standard conditions well known to the person skilled in the art, with a solution of 2M ammonia in EtOH or dioxane at room temperature for 1 hour or using can be performed at various temperature depending on the intrinsic reactivity of compounds XXI, by traditional thermal method or using microwave technology, using standard conditions well known to the person skilled in the art or shown in the Scheme 3, below.

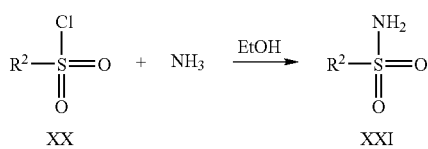

The 2,3-substituted pyrazine sulfonamide derivatives according to the general formula Ia, may be obtained in 3 subsequent steps depending the availability of starting materials and building blocks. A synthetic route is shown in Scheme 4. In a first step, the 2,3-substituted pyrazine sulfonamide derivatives IVa are isolated after condensation of the 3-chloropyrazine sulfonamide compounds III with the boronic acids XXII. This reaction may be performed in presence of appropriated palladium catalysts such as palladium diacetate and in solvents like Dioxane, methanol or solution containing both solvents in various ratios. This reaction can be performed at various temperatures depending on the intrinsic reactivity of compounds III, by traditional thermal method or using microwave technology, using standard conditions well known to the person skilled in the art.

In a subsequent step, the 2,3-substituted pyrazine sulfonamide derivatives Va, whereby the substituent $R^2$ is as above defined, are isolated after chlorination of intermediate compounds IVa in presence of thionyl chloride. This reaction is usually performed at room temperature in solvents like dichloromethane, dichloroethane or DMF, using standard conditions well known to the person skilled in the art.

In a following step, as shown in Scheme 4, the 2,3-substituted pyrazine sulfonamide derivatives Va, may be treated with various nucleophiles, e.g. an amine XXIV or alcohol XXV, wherein $R^4$, $R^5$, $R^6$ are independently selected from the group of hydrogen, alkyl, aryl, heteroaryl, cycloalkyl, heterocycloalkyl or fused ring systems of the mentioned to give the expected 2,3-substituted pyrazine sulfonamide derivative Ia. The nucleophilic displacement of the chlorine atom of the benzylic moiety by the amine XXIV or the alcohol XXV, is accomplished by treatment with an appropriated based such as sodium hydride or potassium tert-butoxide in anhydrous conditions, in presence or absence of e.g. sodium iodine or tetrabutylammonium iodine as catalyst in solvents such as DMF, THF or similar solvents. This reaction can be performed at various temperatures depending on the intrinsic reactivity of compounds Va, XXIV and XXV, by traditional thermal method or using microwave technology, using standard conditions well known to the person skilled in the art.

Scheme 4

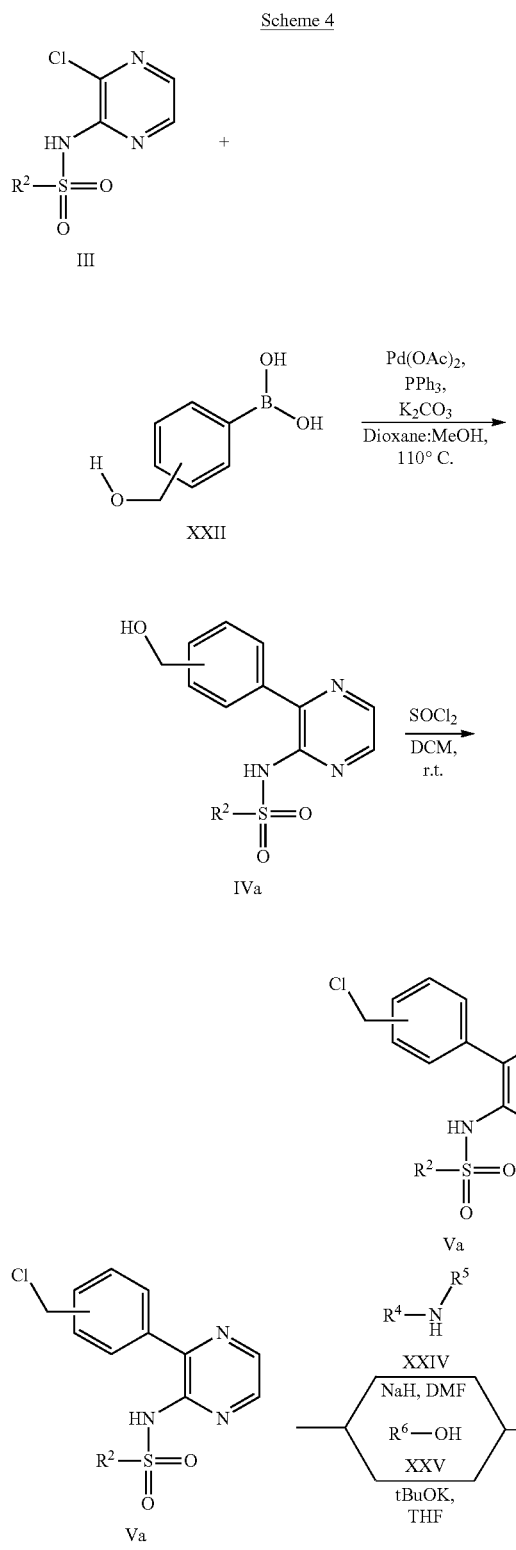

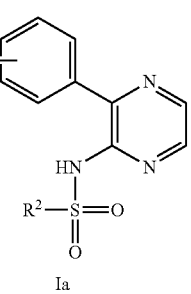

Ia

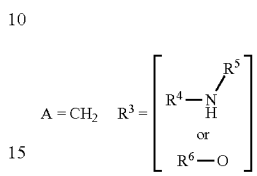

The 2,3-substituted pyrazine sulfonamide derivatives according to the general formula Ia, may also be obtained in 3 subsequent steps depending the availability of starting materials and building blocks. Another synthetic route is shown in Scheme 5. In a first step, the 2,3-substituted pyrazine sulfonamide derivatives IVb are isolated after condensation of the 3-chloropyrazine sulfonamide compounds III with the boronic acids XXIII. This reaction may be performed in presence of appropriate palladium catalysts such as palladium diacetate and in solvents like Dioxane, methanol or a solution containing both solvents in various ratios. This reaction can be performed at various temperatures depending on the intrinsic reactivity of compounds III, by traditional thermal method or using microwave technology, using standard conditions well known to the person skilled in the art.

In a subsequent step, the 2,3-substituted pyrazine sulfonamide derivatives Vb, whereby the substituent $R^2$ is as above defined, are isolated either after chlorination of intermediate compounds IVb in presence of oxalyl chloride or after treatment of compounds IVb with an appropriate coupling reagent such as DCC, HATU or Mukayama reagent in presence of a base like DIPEA or triethylamine. These reactions are usually performed at room temperature in solvents like dichloromethane, dichloroethane or DMF, using standard conditions well known to the person skilled in the art.

In a final step, as shown in Scheme 5, the 2,3-substituted pyrazine sulfonamide derivative Vb, may be treated with various nucleophiles, e.g. an amine XXIV, to give the expected 2,3-substituted pyrazine sulfonamide derivative Ia. The formation of the amide bond is accomplished by treatment with an appropriate base such as DIPEA or triethylamine, in solvents such as DMF, THF or similar solvents. This reaction can be performed at various temperatures depending on the intrinsic reactivity of compounds Vb and XXIV, by traditional thermal method or using microwave technology, using standard conditions well known to the person skilled in the art.

Scheme 5

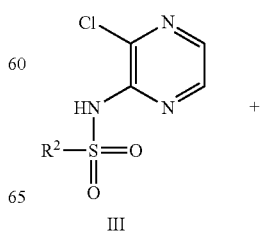

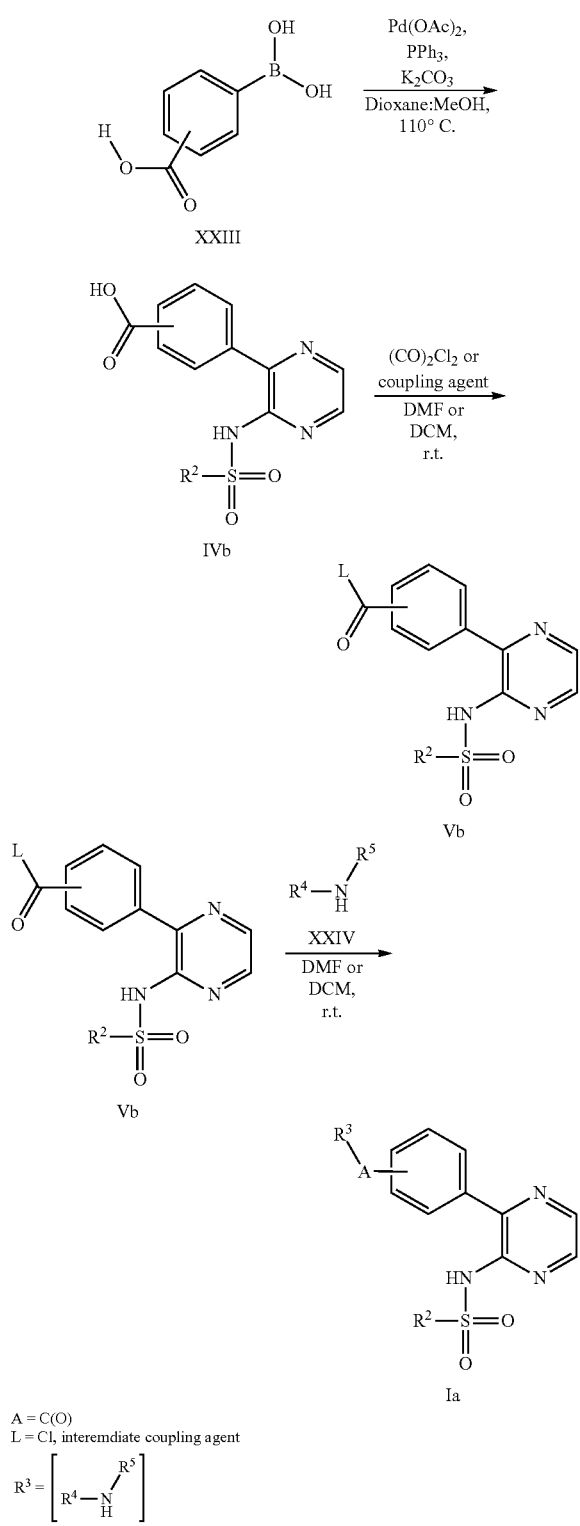

A = C(O)
L = Cl, interemdiate coupling agent $$R^3 = \left[ R^4 - N \diagdown ^{R^5}_H \right]$$

The 2,3-substituted pyrazine sulfonamide derivatives according to the general formula Ib, may be obtained in 3 subsequent steps depending the availability of starting materials and building blocks. A synthetic route is shown in Scheme 6. In a first step, the 2,3-substituted pyrazine sulfonamide derivatives VIa are isolated after condensation of the 3-chloropyrazine sulfonamide compounds III with the boronic acids XXVI. This reaction may be performed in presence of appropriate palladium catalysts such as palladium diacetate and in solvents like Dioxane, methanol or a solution containing both solvents in various ratios. This reaction can be performed at various temperatures depending on the intrinsic reactivity of compounds III, by traditional thermal method or using microwave technology, using standard conditions well known to the person skilled in the art.

In a subsequent step, the 2,3-substituted pyrazine sulfonamide derivatives VIIa, whereby the substituent $R^2$ is as above defined, are isolated after chlorination of intermediate compounds VIa in presence of thionyl chloride. This reaction is usually performed at room temperature in solvents like dichloromethane, dichloroethane or DMF, using standard conditions well known to the person skilled in the art.

In a following step, as shown in Scheme 6, the 2,3-substituted pyrazine sulfonamide derivatives VIIa, may treated with various nucleophiles, e.g. an amine XXIV or alcohol XXV, to give the expected 2,3-substituted pyrazine sulfonamide derivative Ib. The nucleophilic displacement of the chlorine atom of the benzylic moiety by the amine XXIV or the alcohol XXV, is accomplished by treatment with an appropriate base such as sodium hydride or potassium tert-butoxide under anhydrous conditions, in presence or absence of e.g. sodium iodine or tetrabutylammonium iodine as catalyst in solvents such as DMF, THF or similar solvents. This reaction can be performed at various temperatures depending on the intrinsic reactivity of compounds VIIa, XXIV and XXV, by traditional thermal method or using microwave technology, using standard conditions well known to the person skilled in the art.

Scheme 6

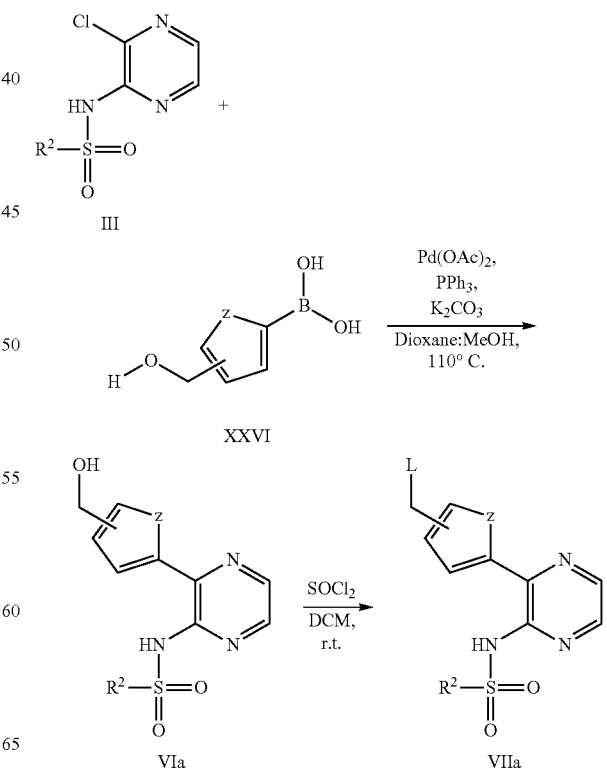

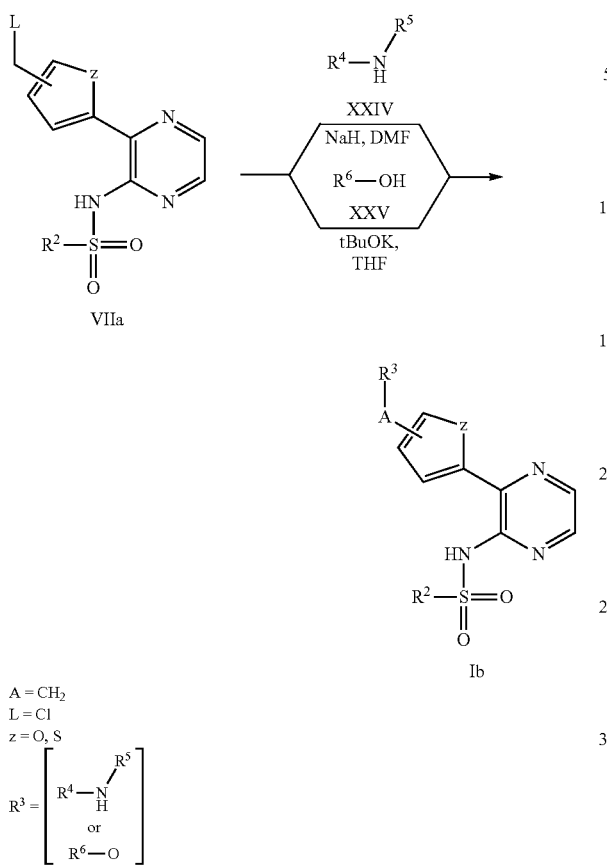

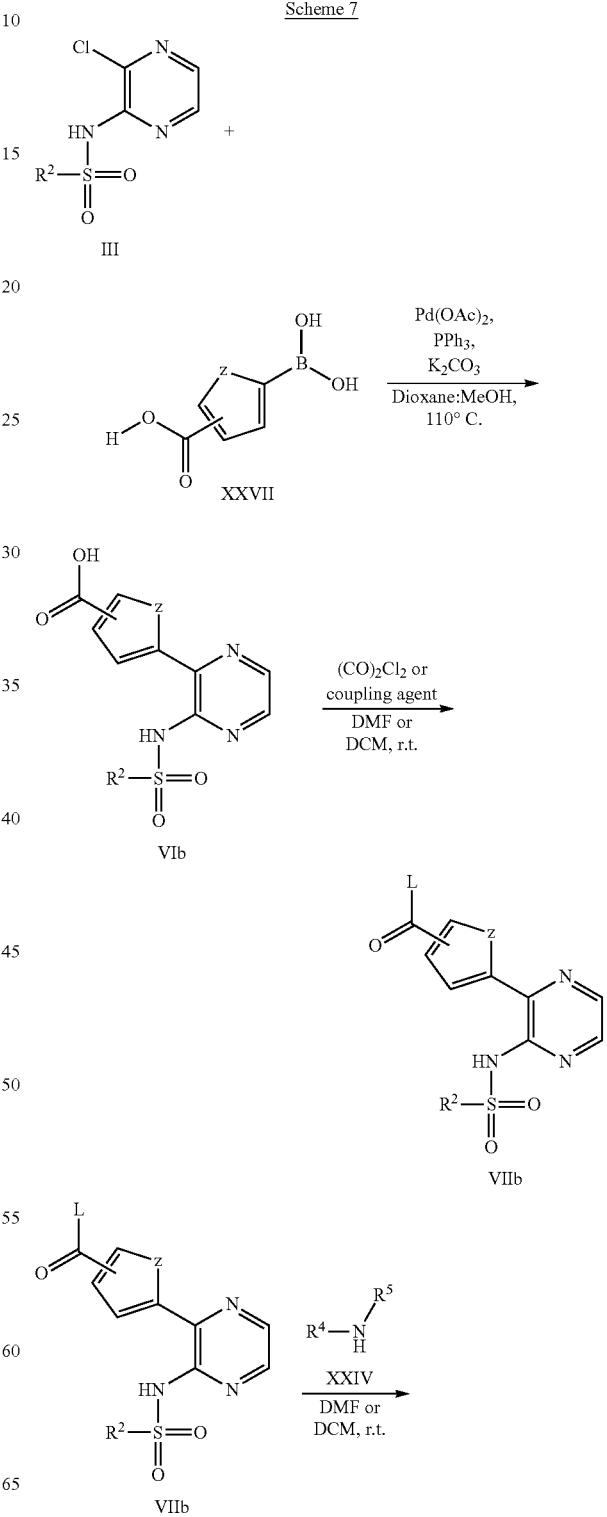

The 2,3-substituted pyrazine sulfonamide derivatives according to the general formula Ib, may also be obtained in 3 subsequent steps depending the availability of starting materials and building blocks. Another synthetic route is shown in Scheme 7. In a first step, the 2,3-substituted pyrazine sulfonamide derivatives VIb are isolated after condensation of the 3-chloropyrazine sulfonamide compounds III with the boronic acids XXVII. This reaction may be performed in presence of appropriate palladium catalysts such as palladium diacetate and in solvents like Dioxane, methanol or a solution containing both solvents in various ratios. This reaction can be performed at various temperatures depending on the intrinsic reactivity of compounds III, by traditional thermal method or using microwave technology, using standard conditions well known to the person skilled in the art.

In a subsequent step, the 2,3-substituted pyrazine sulfonamide derivatives VIIb, whereby the substituent $R^2$ is as above defined, are isolated either after chlorination of intermediate compounds VIb in presence of oxalyl chloride or after treatment of compounds VIb with an appropriate coupling reagent such as DCC, HATU or Mukayama reagent in presence of a base like DIPEA or triethylamine. These reactions are usually performed at room temperature in solvents like dichloromethane, dichloroethane or DMF, using standard conditions well known to the person skilled in the art.

In a final step, as shown in Scheme 7, the 2,3-substituted pyrazine sulfonamide derivatives VIIb, may be treated with various nucleophiles, e.g. an amine XXIV, to give the expected 2,3-substituted pyrazine sulfonamide derivatives Ib. The formation of the amide bond is accomplished by treatment with an appropriate base such as DIPEA or triethylamine, in solvents such as DMF, THF or similar solvents. This reaction can be performed at various temperatures depending on the intrinsic reactivity of compounds VIIb and XXIV, by traditional thermal method or using microwave technology, using standard conditions well known to the person skilled in the art.

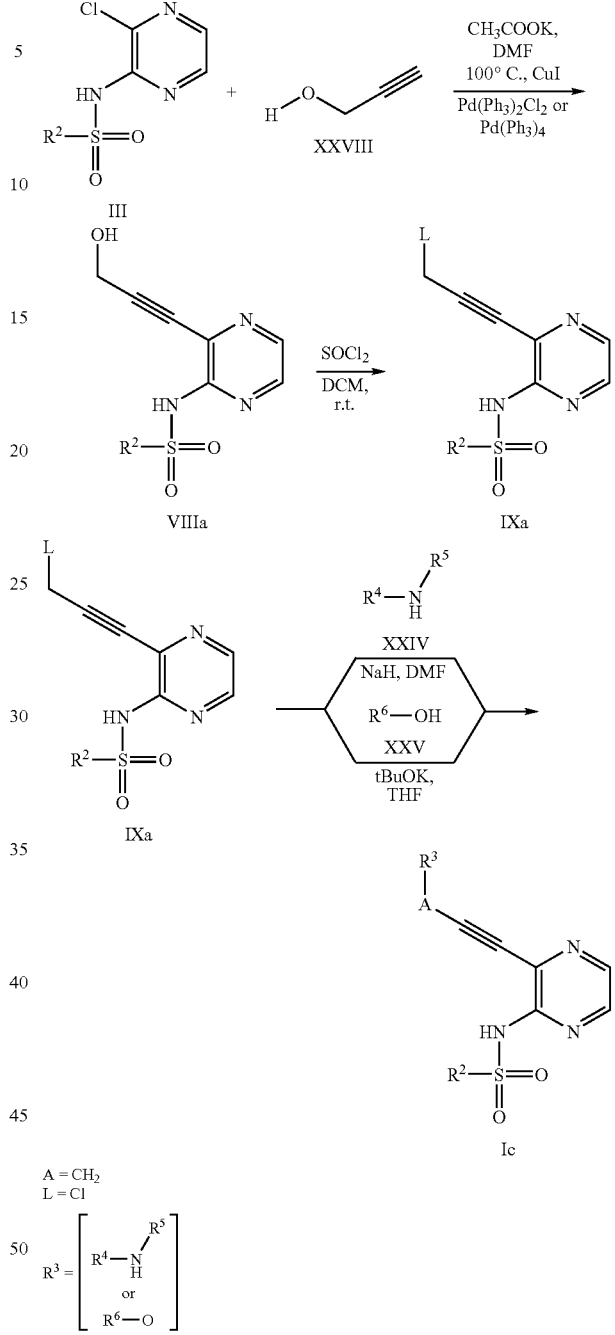

The 2,3-substituted pyrazine sulfonamide derivatives according to the general formula Ic, may be obtained in 3 subsequent steps depending the availability of starting materials and building blocks. A synthetic route is shown in Scheme 8. In a first step, the 2,3-substituted pyrazine sulfonamide derivatives VIIIa are isolated after condensation of the 3-chloropyrazine sulfonamide compounds III with the acetylene XXVIII. This reaction may be performed in the presence of appropriate palladium catalysts such as palladium triphenyl phosphine tetrakis or Pd(Ph$_3$)$_2$Cl$_2$ in presence of copper iodine and potassium acetate, in solvents like Dioxane, DMF or a solution containing both solvents in various ratios. This reaction can be performed at various temperatures depending on the intrinsic reactivity of compounds III, by traditional thermal method or using microwave technology, using standard conditions well known to the person skilled in the art.

In a subsequent step, the 2,3-substituted pyrazine sulfonamide derivatives IXa, whereby the substituent R$^2$ is as above defined, are isolated after chlorination of intermediate compounds VIIIa in presence of thionyl chloride. This reaction is usually performed at room temperature in solvents like dichloromethane, dichloroethane or DMF, using standard conditions well known to the person skilled in the art In a following step, as shown in Scheme 8, the 2,3-substituted pyrazine sulfonamide derivatives IXa, may be treated with various nucleophiles, e.g. an amine XXIV or alcohol XXV, to give the expected 2,3-substituted pyrazine sulfonamide derivatives Ic. The nucleophilic displacement of the chlorine atom of the benzylic moiety by the amine XXIV or the alcohol XXV, is accomplished by treatment with an appropriate base such as sodium hydride or potassium tert-butoxide under anhydrous conditions, in presence or absence of e.g. sodium iodine or tetrabutylammonium iodine as catalyst in solvents such as DMF, THF or similar solvents. This reaction can be performed at various temperatures depending on the intrinsic reactivity of compounds IXa, XXIV and XXV, by traditional thermal method or using microwave technology, using standard conditions well known to the person skilled in the art.

The 2,3-substituted pyrazine sulfonamide derivatives according to the general formula Ic, may also be obtained in 3 subsequent steps depending the availability of starting materials and building blocks. Another synthetic route is shown in Scheme 9. In a first step, the 2,3-substituted pyrazine sulfonamide derivatives VIIb are isolated after condensation of the 3-chloropyrazine sulfonamide compounds III with the acetylene XXIX. This reaction may be performed in the presence of appropriate palladium catalysts such as palladium triphenyl phosphine tetrakis or Pd(Ph$_3$)$_2$Cl$_2$ in presence of copper iodine and potassium acetate, in solvents like Dioxane, DMF or a solution containing both solvents in various ratios. This reaction can be performed at various temperatures depending on the intrinsic reactivity of compounds III, by traditional thermal method or using microwave technology, using standard conditions well known to the person skilled in the art.

In a subsequent step, the 2,3-substituted pyrazine sulfonamide derivatives IXb, whereby the substituent $R^2$ is as above defined, are isolated either after chlorination of intermediate compounds VIIb in the presence of oxalyl chloride or after treatment of compounds VIIb with an appropriate coupling reagent such as DCC, HATU or Mukayama reagent in presence of a base like DIPEA or triethylamine. These reactions are usually performed at room temperature in solvent like dichloromethane, dichloroethane or DMF, using standard conditions well known to the person skilled in the art In a final step, as shown in Scheme 9, the 2,3-substituted pyrazine sulfonamide derivatives IXb, may be treated with various nucleophiles, e.g. an amine XXIV, to give the expected 2,3-substituted pyrazine sulfonamide derivative Ic. The formation of the amide bond is accomplished by treatment with an appropriate base such as DIPEA or triethylamine, in solvents such as DMF, THF or similar solvents. This reaction can be performed at various temperatures depending on the intrinsic reactivity of compounds IXb and XXIV, by traditional thermal method or using microwave technology, using standard conditions well known to the person skilled in the art.

Scheme 9

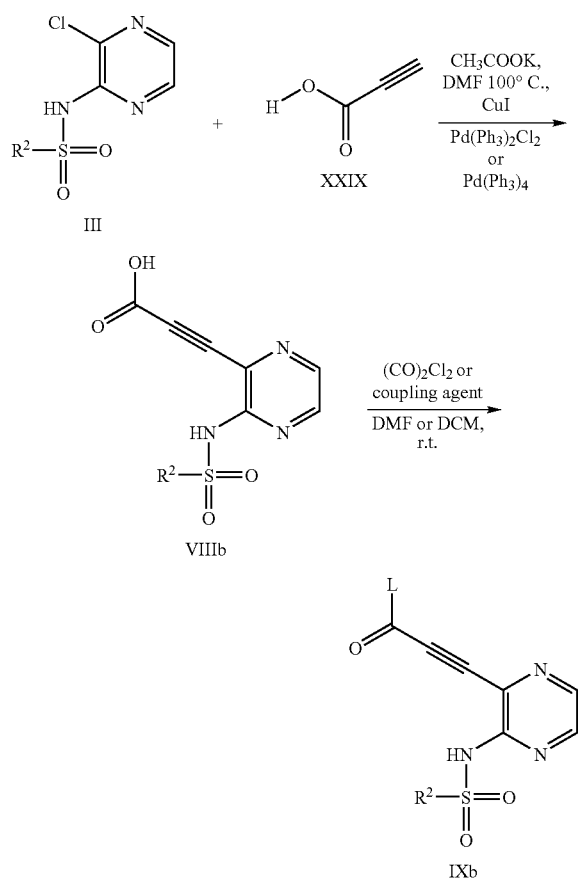

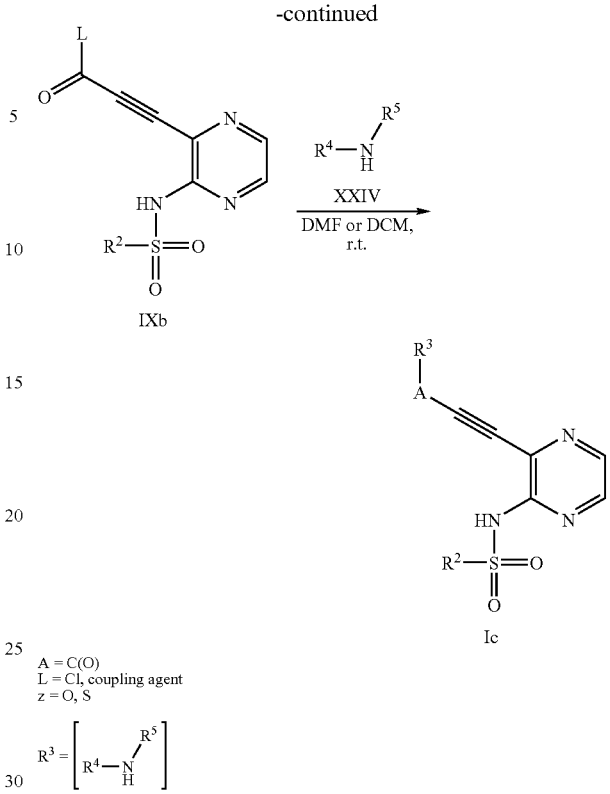

A = C(O)
L = Cl, coupling agent
z = O, S $$R^3 = \left[ R^4 - \underset{H}{N} \diagdown R^5 \right]$$

The 2,3-substituted pyrazine sulfonamide derivatives according to the general formula Id, may be obtained in 3 subsequent steps depending the availability of starting materials and building blocks. A synthetic route is shown in Scheme 10. In a first step, the 2,3-substituted pyrazine sulfonamide derivatives X are isolated after condensation of the 3-chloropyrazine sulfonamide compounds III with the piperazine-1-carboxylic acid tert-butyl ester XXX. This reaction may be performed in presence of an appropriate base such as DIPEA or triethylamine, in solvents like NMP, DMF or a solution containing both solvents in various ratios. This reaction can be performed at various temperatures depending on the intrinsic reactivity of compounds III, by traditional thermal method or using microwave technology, using standard conditions well known to the person skilled in the art.

In a subsequent step, the 2,3-substituted pyrazine sulfonamide derivatives XI, whereby the substituent $R^2$ is deprotected under acidic conditions using either TFA or HCl solution at different concentrations. This reaction is usually performed at room temperature in solvents like dichloromethane, dichloroethane or DMF, using standard conditions well known to the person skilled in the art. In a following step, as shown in Scheme 10, the 2,3-substituted pyrazine sulfonamide derivatives X, may be treated either with various electrophiles, e.g. an alkyl halide XXXIa in the presence of an appropriate base such as $Cs_2CO_3$, DIPEA or triethylamine, or also with an acyl chloride or a carboxylic acid XXXIb initially preactivated by treatment with an appropriate coupling reagent such as DCC, Mukayama reagent, PyBrop, in order to give the expected 2,3-substituted pyrazine sulfonamide derivative Id. The nucleophilic displacement of the halide atom or the formation of the amide bond respectively, with the alkyl halide XXXIa or acyl chloride or carboxylic acid XXXIb can be performed at various temperatures depending on the intrinsic reactivity of compounds XI, XXXIa or XXXIb, by traditional thermal method or using microwave technology, using standard conditions well known to the person skilled in the art.

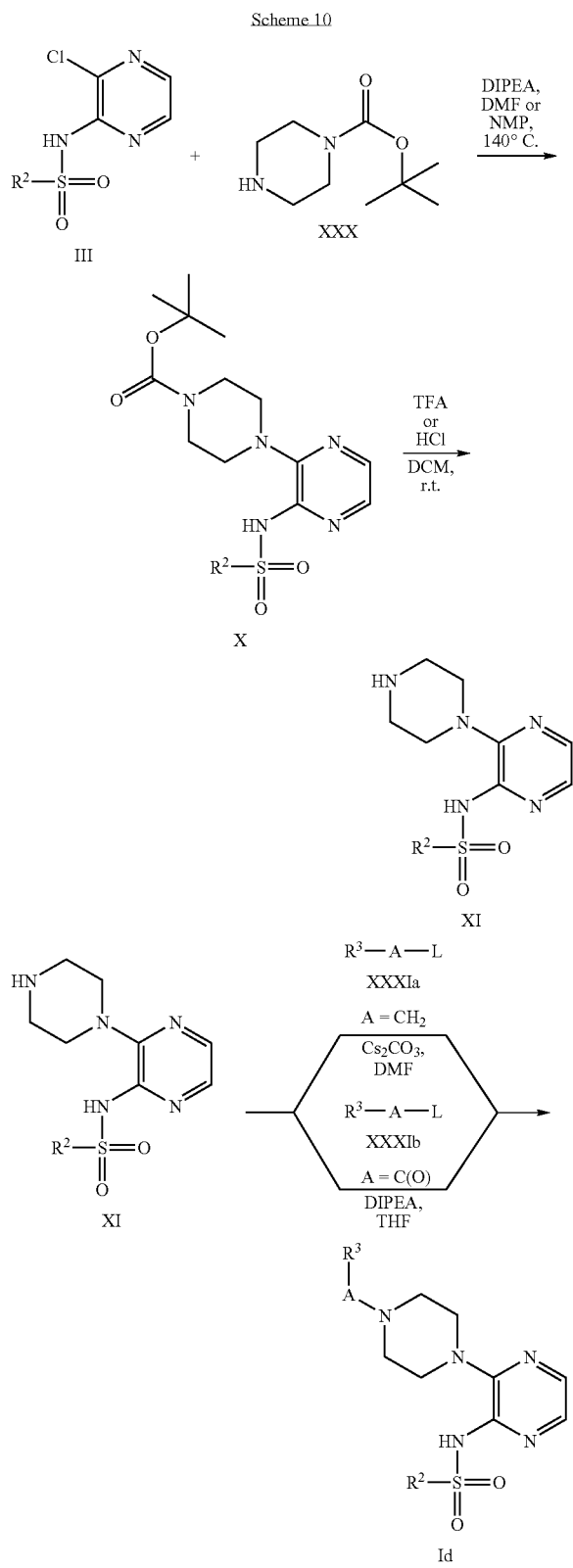

Scheme 10

The following abbreviations refer respectively to the definitions below:

min (minute), hr (hour), g (gram), MHz (Megahertz), ml (milliliter), mmol (millimole), mM (millimolar), RT (room temperature), ATP (Adenoside Triphosphate), BSA (Bovine Serum Albumin), DCM (dichloromethane), DCC (dicyclohexylcarbodiimide), DIPEA (di-isopropyl ethylamine), DMSO (Dimethyl Sulfoxide), Mukayama reagent (1-methyl-2-chloropyridinium iodide), DMF (Dimethylformamide), $CsCO_3$ (Cesium carbonate), cHex (Cyclohexanes), $Et_3N$ (Triethylamine), EtOAc (Ethyl acetate), EtOH (Ethanol), $K_2CO_3$ (potassium carbonate), NaI (Sodium Iodine), NaH (Sodium hydride), $NaHCO_3$ (Sodium bicarbonate), $NH_4Cl$ (Ammonium chloride), TEA (Triethyl amine), TFA (Trifluoroacetic acid), THF (Tetrahydrofuran), $Pd(PPh_3)_4$ (Palladium triphenylphosphine tetrakis), CuI (Copper iodide), $Pd(OAc)_2$ (Palladium II acetate), $Pd(PPh_3)_2Cl_2$ (Bis(triphenylphosphine) Palladium II Chloride), $CH_3COOK$ (Potassium acetate), $PPh_3$ (Triphenylphosphine), HATU (N,N,N',N'-Tetramethyl-O-(7-Azabenzotriazol-1-yl)uranium hexafluorophosphate, $(CO)_2Cl_2$ (Oxalyl chloride), $SOCl_2$ (Thionyl chloride), tBuOK (Potassium tert-butoxide), MeOH (Methanol), $MgSO_4$ (Magnesium sulfate), NMP N-Methyl pyrrolidinone, PetEther (Petroleum ether), rt (room temperature). HPLC (High Performance Liquid Chromatography), FC (Flash Chromatography on silica gel), MS (Mass Spectrometry), NMR (Nuclear Magnetic Resonance), PBS (Phosphate Buffered Saline), SPA (Scintillation Proximity Assay), TLC (Thin Layer Chromatography), UV (Ultraviolet).

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, N.Y., 1994 and, Theodora W. Greene and Peter G. M. Wuts in "*Protective Groups in Organic Synthesis*", Wiley Interscience, $3^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

EXPERIMENTAL PART

The HPLC, NMR and MS data provided in the examples described below are obtained as followed: HPLC: column Waters Symmetry C8 50×4.6 mm, Conditions: MeCN/$H_2O$, 5 to 100% (8 min), max plot 230-400 nm; Mass spectra: PE- SCIEX API 150 EX (APCI and ESI), LC/MS spectra: Waters ZMD (ES); $^1$H-NMR: Bruker DPX-300 MHz.

The preparative HPLC purifications are performed with HPLC Waters Prep LC 4000 System equipped with columns Prep Nova-Pak®HR C18 6 μm 60 Å, 40×30 mm (up to 100 mg) or with XTerra® Prep MS C8, 10 μm, 50×300 mm (up to 1 g). All the purifications are performed with a gradient of MeCN/H$_2$O 0.09% TFA. The semi-preparative reverse-phase HPLC are performed with the Biotage Parallex Flex System equipped with columns Supelcosil™ ABZ+Plus (25 cm×21.2 mm, 12 μm); UV detection at 254 nm and 220 nm; flow 20 mL/min (up to 50 mg). TLC Analysis is performed on Merck Precoated 60 F$_{254}$ plates. Purifications by flash chromatography are performed on SiO$_2$ support, using cyclohexane/EtOAc or DCM/MeOH mixtures as eluents.

Intermediate 1: 2-(trifluoromethyl)benzenesulfonamide (cf. Scheme 3, Compound XXI)

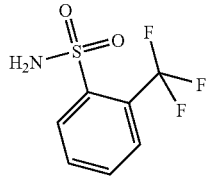

To a solution of 2-(trifluoromethyl)benzenesulfonyl chloride (5 g; 20.44 mmol; 1.00 eq.) in anhydrous THF (5.00 ml) was added a solution of 71 ml Ammonia in Ethanol 2M under nitrogen at room temperature. The reaction mixture was shaken for 20 h at room temperature. The solvent was evaporated and the residue redissolved in EtOAc (150 mL) and then washed with NH$_4$Cl saturated aqueous solution (50 mL) and brine (50 mL). The organic layer was dried over MgSO$_4$, filtered and the solvent evaporated to give the pure 2-(trifluoromethyl)benzenesulfonamide as a yellowish solid (4.6 g, 89% yield, 98.6% HPLC purity). This compound was utilized as such for the next reaction.

1H NMR (300 MHz, CDCl$_3$); 5.0 (m, 2H), 7.6 (m, 2H), 7.8 (m, 1H), 8.3 (m, 1H). MS (ESI$^-$): 224.1.

Intermediate 2: 2-chloro-N-(3-chloropyrazin-2-yl)benzenesulfonamide (cf. Scheme 2, Compound III)

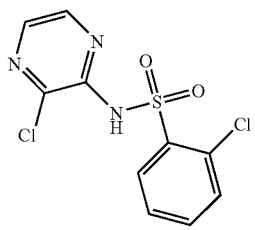 [SMILES: O=S(=O)(Nc1nccnc1Cl)c1ccccc1Cl]

2,3-dichloropyrazine (1 g; 6.71 mmol; 1.00 eq.) and 2-dichlorobenzenesulfonamide (1.29 g; 6.71 mmol; 1.00 eq.) were stirred in NMP (9 ml). To this reaction mixture was added cesium carbonate (2 g; 6 mmol; 0.90 eq.) and the reaction mixture was stirred and heated up to 130° C. for 20 h. The reaction was cooled down to room temperature, added to water 98 ml and washed with AcOEt (2×30 ml). The aqueous phase was acidified with citric acid and extracted with AcOEt (3×60 ml). The organic extracts were combined, washed with brine (10 ml), dried over MgSO4 and evaporated down. The residue was purified by Flash master using a gradient AcOEt/cHex 2:8 to AcOEt 100% in 45 min, the title compound was isolated, after filtration and evaporation. The solid was recrystallized in a mixture EtOAc:Chex (30:70) to give the pure 2-chloro-N-(3-chloropyrazin-2-yl)benzene sulfonamide as a yellowish solid (1 g, 49% yield, 100% HPLC purity).

1H NMR (300 MHz, CDCl$_3$); 7.3-7.5 (m, 3H), 7.8-8.0 (m, 3H), 8.3 (m, 1H). MS (ESI$^+$): 304.1; MS (ESI$^-$): 302.0.

Intermediate 3: N-(3-chloropyrazin-2-yl)-2-(trifluoromethyl)benzenesulfonamide (cf. Scheme 2, Compound III)

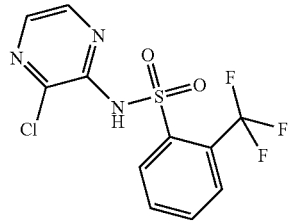 [SMILES: O=S(=O)(Nc1nccnc1Cl)c1ccccc1C(F)(F)F]

Following the general method as outlined for Intermediate 2, starting from 2,3-dichloropyrazine and 2-(trifluoromethyl)benzenesulfonamide, the title compound was isolated, after evaporation and recrystallization, as a yellowish solid in 63% yield (97% purity by HPLC).

1H NMR (300 MHz, CDCl$_3$); 7.6-7.8 (m, 4H), 7.9-8.1 (m, 2H), 8.5 (m, 1H). MS (ESI$^+$): 338.0; MS (ESI$^-$): 336.0.

Intermediate 4: 2-chloro-N-{3-[4-(hydroxymethyl)phenyl]pyrazin-2-yl}benzene sulfonamide (cf. Scheme 4, Compound IVa)

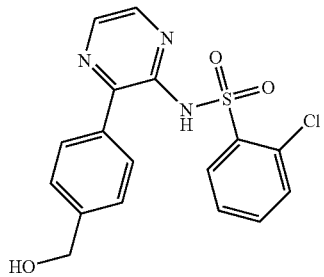 [SMILES: O=S(=O)(Nc1nccnc1-c1ccc(CO)cc1)c1ccccc1Cl]

2-chloro-N-(3-chloropyrazin-2-yl)benzenesulfonamide (2.2 g; 7.23 mmol; 1.00 eq.) and 4-hydroxymethyl benzene boronic acid (1.21 g; 7.96 mmol; 1.10 eq.) were dissolved in 48 mL of a 1:1 mixture of Dioxane:MeOH that was previously degassed. Potassium carbonate (2.75 g; 19.89 mmol; 2.75 eq.) and triphenylphosphine (284.58 mg; 1.08 mmol; 0.15 eq.) were added to the reaction mixture under nitrogen, followed by palladium II (81.19 mg; 0.36 mmol; 0.05 eq.). The reaction mixture was then heated at 110° C. under N2 for 30 minutes. The reaction mixture was cooled down to room temperature, diluted with diethyl ether (50 mL) and water (25 mL) and filtered through celite. The aqueous layer was separated and the organic layer washed with water (50 mL). The combined aqueous solutions were washed with diethyl ether (50 mL), then acidified aqueous layer with HCl 5N and extracted with AcOEt. The organic extracts were combined, washed with brine (10 ml), dried over MgSO₄ and evaporated down to give the pure 2-chloro-N-{3-[4-(hydroxymethyl) phenyl]pyrazin-2-yl}benzene sulfonamide as a yellowish solid (2.5 g, 91% yield, 98% HPLC purity). This compound was used as such for the next reaction.

1H NMR (300 MHz, CDCl₃); 4.68 (m, 2H), 7.5-7.7 (m, 7H), 8.1-8.2 (m, 3H), 8.3 (m, 1H). MS (ESI⁺): 376.1; MS (ESI⁻): 374.1.

Intermediate 5: 2-trifluoromethyl-N-{3-[4-(hydroxymethyl)phenyl]pyrazin-2-yl}benzene sulfonamide (cf. Scheme 4, Compound IVa)

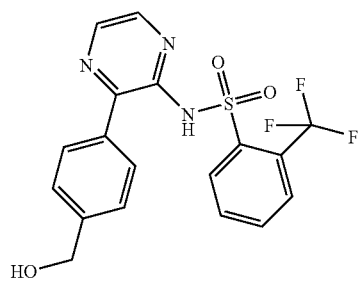 [SMILES: O=S(=O)(Nc1nccnc1-c1ccc(CO)cc1)c1ccccc1C(F)(F)F]

Following the general method as outlined for Intermediate 4, starting from N-(3-chloropyrazin-2-yl)-2-(trifluoromethyl)benzenesulfonamide and 4-hydroxymethyl benzene boronic acid, the title compound was isolated, after evaporation and recrystallization, as a yellowish solid in 85% yield (97% purity by HPLC).

1H NMR (300 MHz, CDCl₃); 4.83 (m, 2H), 7.5-7.9 (m, 8H), 8.1 (m, 1H), 8.3 (m, 1H), 8.64 (m, 1H). MS (ESI⁺): 410.3; MS (ESI⁻): 408.5.

Intermediate 6: 4-(3-{[(2-chlorophenyl)sulfonyl]amino}pyrazin-2-yl)benzoic acid (cf. Scheme 5, Compound IVb)

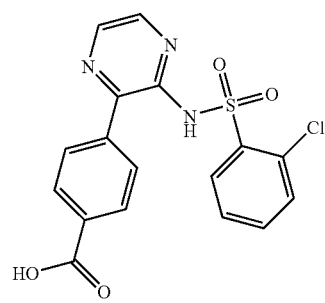 [SMILES: O=C(O)c1ccc(-c2nccnc2NS(=O)(=O)c2ccccc2Cl)cc1]

Following the general method as outlined for Intermediate 4, starting from 2-chloro-N-(3-chloropyrazin-2-yl)benzenesulfonamide and 4-carboxybenzene boronic acid, the title compound was isolated, after evaporation and recrystallization, as a yellowish solid in 83% yield (96% purity by HPLC).

1H NMR (300 MHz, CDCl₃); 7.5-7.7 (m, 4H), 7.9-8.0 (m, 2H), 8.1-8.4 (m, 5H). MS (ESI⁺): 390.8; MS (ESI⁻): 388.9.

Intermediate 7: 4-(3-{[(2-trifluoromethylphenyl)sulfonyl]amino}pyrazin-2-yl)benzoic acid (cf. Scheme 5, Compound IVb)

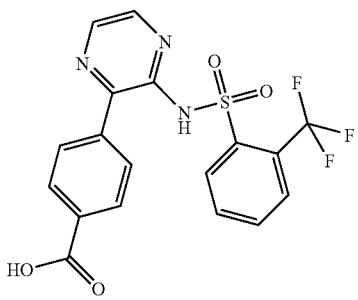 [SMILES: O=C(O)c1ccc(-c2nccnc2NS(=O)(=O)c2ccccc2C(F)(F)F)cc1]

Following the general method as outlined for Intermediate 4, starting from N-(3-chloropyrazin-2-yl)-2-(trifluoromethyl)benzenesulfonamide and 4-carboxybenzene boronic acid, the title compound was isolated, after evaporation and recrystallization, as a yellowish solid in 80% yield (98% purity by HPLC).

MS (ESI⁺): 424.4; MS (ESI⁻): 422.2.

Intermediate 8: 2-chloro-N-{3-[4-(chloromethyl)phenyl]pyrazin-2-yl}benzene-sulfonamide (cf. Scheme 4, Compound Vb)

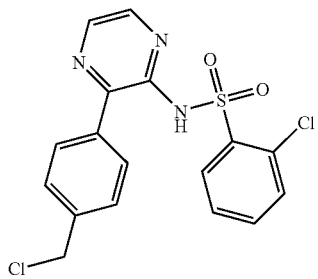 [SMILES: O=S(=O)(Nc1nccnc1-c1ccc(CCl)cc1)c1ccccc1Cl]

2-chloro-N-{3-[4-(hydroxymethyl)phenyl]pyrazin-2-yl}benzene sulfonamide (3.15 g; 8.4 mmol; 1.00 eq.) was dissolved in dichloromethane (80 mL) and thionyl chloride (8.5 mL, 117 mmol, 14 eq.) was added dropwise. The reaction mixture was stirred overnight. The reaction mixture was poured carefully into ice/water (200 mL) and stirred until clear layers were formed. The mixture was separated and the organic layer was dried over MgSO4 and evaporated down to give the crude solid which was recrystallised in AcOEt/cyclohexane to give the pure 2-chloro-N-{3-[4-(chloromethyl)phenyl]pyrazin-2-yl}benzenesulfonamide as a white solid (3.02 g, 95% yield, 99% HPLC purity).

1H NMR (300 MHz, CDCl₃); 4.69 (m, 2H), 7.45-7.6 (m, 3H), 7.65-7.7 (m, 5H), 8.0 (m, 1H), 8.3 (m, 1H), 8.38 (m, 1H). MS (ESI⁺): 396.1; MS (ESI⁻): 393.1.

Intermediate 9: N-{3-[4-(chloromethyl)phenyl]pyrazin-2-yl}-2-(trifluoromethyl)benzenesulfonamide (cf. Scheme 4, Compound Vb)

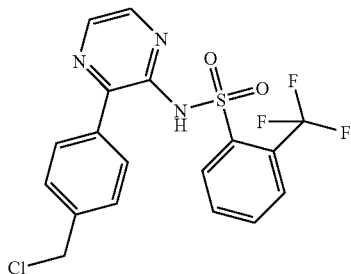 [SMILES: O=S(=O)(Nc1nccnc1-c1ccc(CCl)cc1)c1ccccc1C(F)(F)F]

Following the general method as outlined for Intermediate 8, starting from 2-trifluoromethyl-N-{3-[4-(hydroxymethyl)phenyl]pyrazin-2-yl}benzene sulfonamide and thionyl chloride, the title compound was isolated, after evaporation and recrystallization, as a white solid in 96% yield (97% purity by HPLC).

MS (ESI$^+$): 428.9; MS (ESI$^-$): 426.7.

Intermediate 10: N-[3-(3-hydroxyprop-1-yn-1-yl)pyrazin-2-yl]-2-(trifluoromethyl)benzene sulfonamide (cf. Scheme 8, Compound VIIIa)

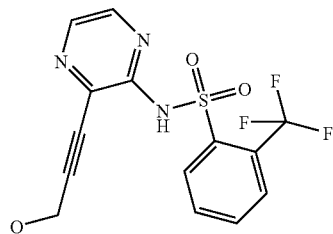 [SMILES: O=S(=O)(Nc1nccnc1C#CCO)c1ccccc1C(F)(F)F]

Method A:
N-(3-chloropyrazin-2-yl)-2-(trifluoromethyl)benzenesulfonamide (1.35 g; 4.0 mmol; 1.00 eq.) and 2-propyn-1-ol (336 mg; 6.0 mmol; 1.5 eq.) were dissolved in 10 mL of DMF under nitrogen atmosphere. To the reaction mixture was added CH$_3$COOK (588 mg; 6.0 mmol; 1.5 eq.) and Pd(PPh$_3$)$_4$ (232 mg; 0.2 mmol) under nitrogen. The reaction mixture was then heated at 100° C. under nitrogen for 2 hours. After removal of the solvent by distillation in vacuo, the residue was triturated with water (40 mL) and extracted with diethyl ether (3×30 mL). The organic layer was dried over MgSO4 and evaporated down. The crude product was purified by silica gel column chromatography using a mixture of hexane and AcOEt to give pure N-[3-(3-hydroxyprop-1-yn-1-yl)pyrazin-2-yl]-2-(trifluoromethyl)benzenesulfonamide as a yellowish solid (686 mg, 48% yield, 98% HPLC purity).

Method B:
N-(3-chloropyrazin-2-yl)-2-(trifluoromethyl)benzenesulfonamide (1.35 g; 4.0 mmol; 1.00 eq.) and 2-propyn-1-ol (336 mg 6.0 mmol; 1.5 eq.) were dissolved in 10 mL of DMF under nitrogen atmosphere. To the reaction mixture was added CH$_3$COOK (588 mg; 6.0 mmol; 1.5 eq.) CuI (40 mg; 0.2 mmol; 0.05 eq.) and Pd(PPh$_3$)$_2$Cl$_2$ (28 mg; 0.04 mmol) under nitrogen. The reaction mixture was then heated at 100° C. under nitrogen for 2 hours. After removal of the solvent by distillation in vacuo, the residue was triturated with water (40 mL) and extracted with diethyl ether (3×30 mL). The organic layer was dried over MgSO$_4$ and evaporated down. The crude product was purified by silica gel column chromatography using a mixture of hexane and AcOEt to give pure N-[3-(3-hydroxyprop-1-yn-1-yl)pyrazin-2-yl]-2-(trifluoromethyl)benzenesulfonamide as a yellowish solid (702 mg, 50% yield, 98% HPLC purity).

MS (ESI$^+$): 358.6; MS (ESI$^-$): 356.5.

Intermediate 11: N-(3-piperazin-1-ylpyrazin-2-yl)-2-(trifluoromethyl)benzenesulfonamide (cf. Scheme 10, Compound XI)

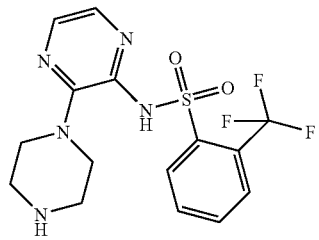 [SMILES: O=S(=O)(Nc1nccnc1N1CCNCC1)c1ccccc1C(F)(F)F]

tert-butyl 4-[3-({[2-(trifluoromethyl)phenyl]sulfonyl}amino)pyrazin-2-yl]piperazine-1-carboxylate (1.46 g, 3 mmol) was dissolved in dichloromethane (50 mL) and trifluoroacetic acid (4.5 g, 40 mmol) was added at 0° C. The reaction mixture was stirred for 2 h. The solvents were evaporated and the residue redissolved in dichloromethane (50 ml) and evaporated to dryness to give the expected product N-(3-piperazin-1-ylpyrazin-2-yl)-2-(trifluoromethyl)benzenesulfonamide as a yellow solid (1.1 g, 95% yield, 95% purity by HPLC).

MS (ESI$^+$): 388.4; MS (ESI$^-$): 386.3.

Example 1

General Procedure for the Synthesis of 2,3-Substituted Pyrazine Sulfonamide Derivatives of General Formula I, with A and Z as Above Defined (Schemes 1, 4, 5, 6, 7, 8, 9 and 10): N-{3-[4-(1H-indol-1-ylmethyl)phenyl]pyrazin-2-yl}-2-(trifluoromethyl)benzene-sulfonamide

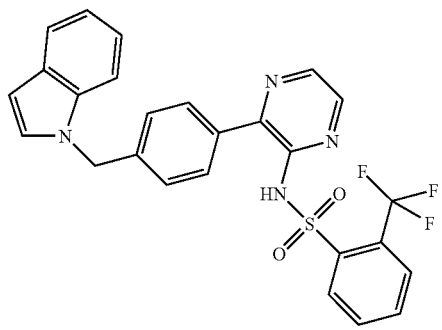

Method A:
To a solution of 1H-Indole (234 mg, 2.0 mmol, 1 eq) in dimethylformamide (10 mL) was added sodium hydride (80 mg, 2 mmol, 1 eq). After the evolution of hydrogen ceased, N-{3-[4-(chloromethyl)phenyl]pyrazin-2-yl}-2-(trifluoromethyl)benzene sulfonamide (intermediate 26) (854 mg, 2 mmol, 1 eq) in dimethylformamide (5 mL) was added and the reaction mixture heated to 80 degrees over 3 hours. The reaction was cooled, diluted with 30 mL of water and extracted with diethyl ether. The organic layer was dried over MgSO₄, evaporated and purified by flash chromatography on silica gel eluting with AcOEt and cyclohexane to give pure N-{3-[4-(1H-indol-1-ylmethyl)phenyl]pyrazin-2-yl}-2-(trifluoromethyl)benzenesulfonamide as a yellow solid (630 mg, 1.24 mmol, yield: 62%, 97% HPLC purity).

Method B:

N-{3-[4-(chloromethyl)phenyl]pyrazin-2-yl}-2-(trifluoromethyl)benzene sulfonamide (intermediate 26) (854 mg, 2 mmol, 1 eq) and 1H-Indole (234 mg, 2.0 mmol, 1 eq) were shaken in tetrahydrofuran (20 mL) and heated up to 50 degrees for 10 minutes. To the reaction mixture was added potassium tert-butoxide (4.5 mL of a 1M solution in THF). The reaction mixture was maintained to 50 degrees for 5 h, and then cooled down to room temperature. The reaction mixture was treated with 10 ml of an aqueous citric acid solution (20 g in 100 mL of water) and extracted with AcOEt. The organic layer was dried over MgSO₄ and evaporated. The crude was purified similarly to Method A to give pure N-{3-[4-(1H-indol-1-ylmethyl)phenyl]pyrazin-2-yl}-2-(trifluoromethyl)benzenesulfonamide as a yellow solid (691 mg, 1.36 mmol, yield: 68%, 98% HPLC purity).

N-{3-[4-(1H-indol-1-ylmethyl)phenyl]pyrazin-2-yl}-2-(trifluoromethyl)benzene sulfonamide yellow solid; $^1$H NMR (300 MHz, CDCl$_3$); 5.50 (m, 2H), 6.5 (m, 1H), 7.0-7.2 (m, 2H), 7.4-7.65 (m, 8H), 7.65-7.7 (m, 2H), 8.0 (m, 2H), 8.3 (m, 1H), 8.38 (m, 1H). MS (ESI+) 509.5, (ESI−) 507.6.

Example 2

2-chloro-N-{3-[4-({methyl[4-(trifluoromethoxy)phenyl]amino}-methyl)-phenyl]pyrazin-2-yl}benzene sulfonamide

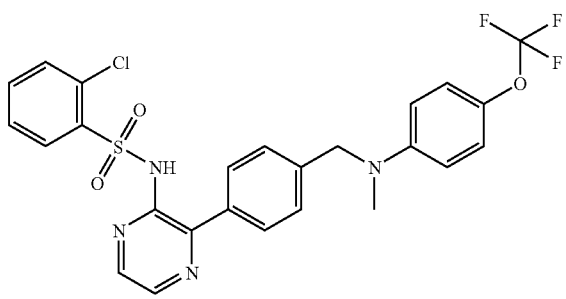 [SMILES: CN(Cc1ccc(-c2nccnc2NS(=O)(=O)c2ccccc2Cl)cc1)c1ccc(OC(F)(F)F)cc1]

Following the general methods as outlined in Example 1 (Method B), starting from 2-chloro-N-{3-[4-(chloromethyl)phenyl]pyrazin-2-yl}benzenesulfonamide (Intermediate 8), and N-methyl-4-(trifluoromethoxy)aniline, the title compound was isolated as a yellow solid in 72% yield (99% purity by HPLC).

MS (ESI⁺): 550.1; MS (ESI⁻): 547.8.

Example 3

N-(3-{4-[(2-ethyl-1H-benzimidazol-1-yl)methyl]phenyl}pyrazin-2-yl)-2-(trifluoromethyl)benzenesulfonamide

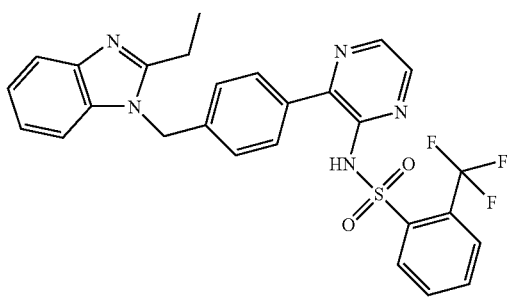 [SMILES: CCc1nc2ccccc2n1Cc1ccc(-c2nccnc2NS(=O)(=O)c2ccccc2C(F)(F)F)cc1]

Following the general method as outlined in Example 1 (Method B), starting from N-{3-[4-(chloromethyl)phenyl]pyrazin-2-yl}-2-(trifluoromethyl)benzenesulfonamide (Intermediate 9), and 2-ethylbenzimidazole, the title compound was isolated as a yellow solid in 63% yield (96% purity by HPLC).

MS (ESI⁺): 538.6; MS (ESI⁻): 536.5.

Example 4

2-chloro-N-[3-(4-{[methyl(phenyl)amino]methyl}phenyl)pyrazin-2-yl]-benzenesulfonamide

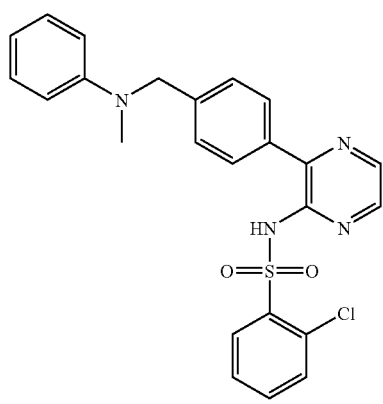 [SMILES: CN(Cc1ccc(-c2nccnc2NS(=O)(=O)c2ccccc2Cl)cc1)c1ccccc1]

Following the general method as outlined in Example 1 (Method B), starting from 2-chloro-N-{3-[4-(chloromethyl)phenyl]pyrazin-2-yl}benzenesulfonamide (Intermediate 8), and N-methyl-aniline, the title compound was isolated as a yellow solid in 83% yield (99% purity by HPLC).

MS (ESI⁺): 465.6; MS (ESI⁻): 463.8.

Example 5

2-chloro-N-(3-{4-[(2-naphthyloxy)methyl]phenyl}pyrazin-2-yl)benzene-sulfonamide

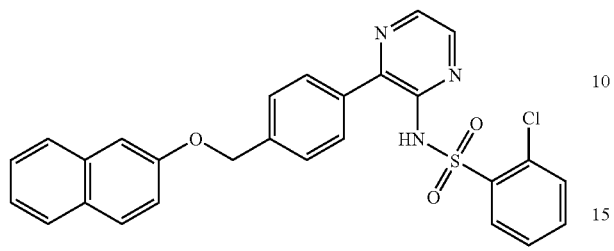

Following the general method as outlined in Example 1 (Method A), starting from 2-chloro-N-{3-[4-(chloromethyl)phenyl]pyrazin-2-yl}benzenesulfonamide (Intermediate 8), and 2-hydroxy naphthalene, the title compound was isolated as a yellow solid in 72% yield (99% purity by HPLC).
MS (ESI$^+$): 503.4; MS (ESI$^-$): 501.2.

Example 6

2-chloro-N-{3-[4-(1H-indol-1-ylmethyl)phenyl]pyrazin-2-yl}benzene-sulfonamide

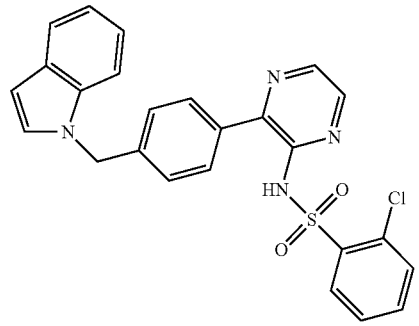 [SMILES: O=S(=O)(Nc1nccnc1-c1ccc(Cn2ccc3ccccc32)cc1)c1ccccc1Cl]

Following the general method as outlined in Example 1 (Method B), starting from 2-chloro-N-{3-[4-(chloromethyl)phenyl]pyrazin-2-yl}benzenesulfonamide (Intermediate 8), and 1-H-Indole, the title compound was isolated as a yellow solid in 71% yield (98% purity by HPLC).
MS (ESI$^+$): 475.9; MS (ESI$^-$): 473.5.

Example 7

2-chloro-N-(3-{4-[(5,6,7,8-tetrahydronaphthalen-2-yloxy)methyl]-phenyl}-pyrazin-2-yl)benzene-sulfonamide

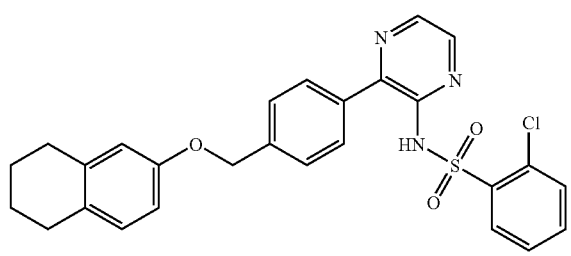 [SMILES: O=S(=O)(Nc1nccnc1-c1ccc(COc2ccc3c(c2)CCCC3)cc1)c1ccccc1Cl]

Following the general method as outlined in Example 1 (Method B), starting from 2-chloro-N-{3-[4-(chloromethyl)phenyl]pyrazin-2-yl}benzenesulfonamide (Intermediate 8), and 6-hydroxy-1,2,3,4-tetrahydronaphtalene, the title compound was isolated as a yellow solid in 69% yield (99% purity by HPLC).
MS (ESI$^+$): 507.6; MS (ESI$^-$): 505.2.

Example 8

2-chloro-N-(3-{4-[(2-ethyl-1H-benzimidazol-1-yl)methyl]phenyl}pyrazin-2-yl)benzenesulfonamide

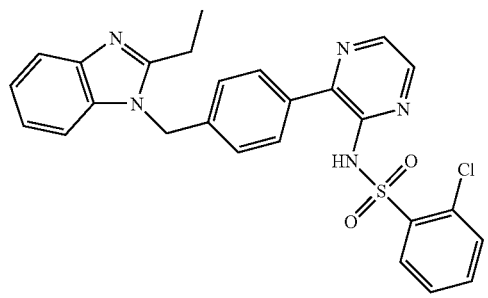 [SMILES: CCc1nc2ccccc2n1Cc1ccc(-c2nccnc2NS(=O)(=O)c2ccccc2Cl)cc1]

Following the general method as outlined in Example 1 (Method B), starting from 2-chloro-N-{3-[4-(chloromethyl)phenyl]pyrazin-2-yl}benzenesulfonamide (Intermediate 8), and 2-ethyl benzimidazole, the title compound was isolated as a yellow solid in 65% yield (96% purity by HPLC).
MS (ESI$^+$): 505.4; MS (ESI$^-$): 503.2.

Example 9

N-(3-{4-[(1,3-benzodioxol-5-ylamino)methyl]phenyl}pyrazin-2-yl)-2-(trifluoromethyl)benzene-sulfonamide

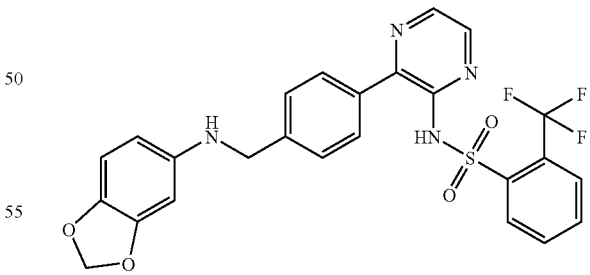

Following the general method as outlined in Example 1 (Method B), starting from N-{3-[4-(chloromethyl)phenyl]pyrazin-2-yl}-2-(trifluoromethyl)benzenesulfonamide (Intermediate 9), and 3,4-(methylenedioxy)aniline, the title compound was isolated as a yellow solid in 69% yield (96% purity by HPLC).
MS (ESI$^+$): 529.7; MS (ESI$^-$): 527.5.

Example 10

N-[3-(4-{[(3-methoxybenzyl)oxy]methyl}phenyl)pyrazin-2-yl]-2-(trifluoromethyl)benzenesulfonamide

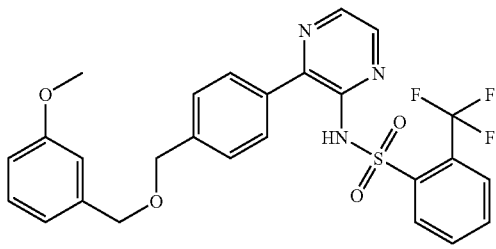 [SMILES: COc1cccc(COCc2ccc(-c3nccnc3NS(=O)(=O)c3ccccc3C(F)(F)F)cc2)c1]

Following the general method as outlined in Example 1 (Method B), starting from N-{3-[4-(chloromethyl)phenyl]pyrazin-2-yl}-2-(trifluoromethyl)benzenesulfonamide (Intermediate 9), and 3-anisyl alcohol, the title compound was isolated as a yellow solid in 64% yield (92% purity by HPLC).
MS (ESI$^+$): 530.4; MS (ESI$^-$): 528.8.

Example 11

3-chloro-N-{3-[4-({methyl[4-(trifluoromethoxy)phenyl]amino}methyl)phenyl]pyrazin-2-yl}benzenesulfonamide

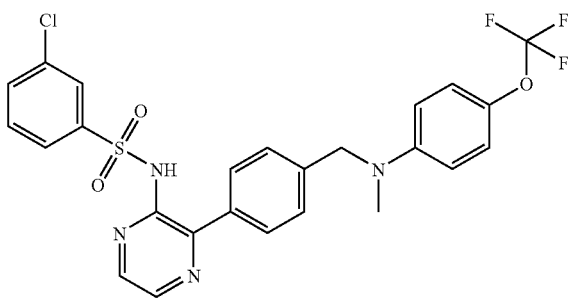 [SMILES: CN(Cc1ccc(-c2nccnc2NS(=O)(=O)c2cccc(Cl)c2)cc1)c1ccc(OC(F)(F)F)cc1]

Following the general method as outlined in Example 1 (Method B), starting from 3-chloro-N-{3-[4-(chloromethyl)phenyl]pyrazin-2-yl}benzenesulfonamide, and N-methyl-4-(trifluoromethoxy)aniline, the title compound was isolated as a yellow solid in 69% yield (94% purity by HPLC).
MS (ESI$^+$): 550.2; MS (ESI$^-$): 547.6.

Example 12

N-[3-(4-{[(4-chlorophenyl)(methyl)amino]methyl}phenyl)pyrazin-2-yl]-thiophene-2-sulfonamide

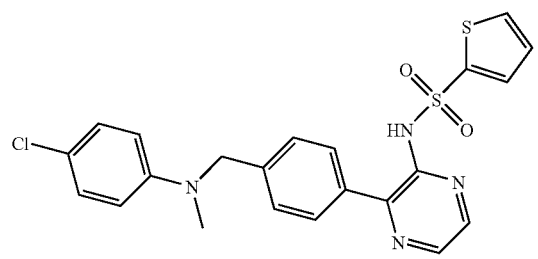 [SMILES: CN(Cc1ccc(-c2nccnc2NS(=O)(=O)c2cccs2)cc1)c1ccc(Cl)cc1]

Following the general method as outlined in Example 1 (Method B), starting from N-{3-[4-(chloromethyl)phenyl]pyrazin-2-yl}thiophene-2-sulfonamide, and N-methyl-4-chloro aniline, the title compound was isolated as a yellow solid in 69% yield (94% purity by HPLC).
MS (ESI$^+$): 472.8; MS (ESI$^-$): 470.7.

Example 13

4-phenoxy-N-{3-[4-(quinolin-2-ylmethyl)piperazin-1-yl]pyrazin-2-yl}-benzenesulfonamide

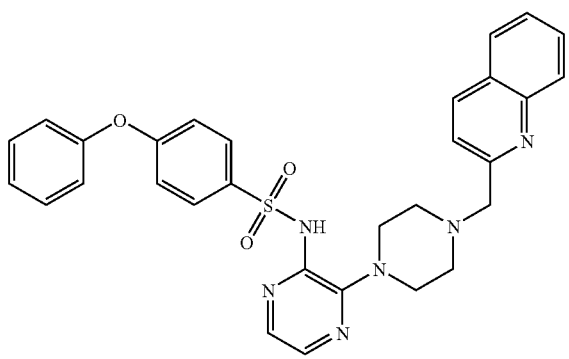 [SMILES: O=S(=O)(Nc1nccnc1N1CCN(Cc2ccc3ccccc3n2)CC1)c1ccc(Oc2ccccc2)cc1]

To a solution of 4-phenoxy-N-(3-piperazin-1-ylpyrazin-2-yl)benzenesulfonamide (411 mg, 1.0 mmol, 1 eq) in dimethylformamide (10 mL) was added 2-(chloromethyl)quinoline hydrochloride (214 mg, 1 mmol, 1 eq) and DIPEA (322 mg, 2.5 mmol, 2.5 eq). The reaction mixture was heated to 50 degrees over 1 hour. The reaction was cooled, diluted with 30 mL of water and extracted with diethyl ether. The organic layer was dried over MgSO$_4$, evaporated and purified by flash chromatography on silica gel eluting with AcOEt and cyclohexane to give pure 4-phenoxy-N-{3-[4-(quinolin-2-ylmethyl)piperazin-1-yl]pyrazin-2-yl}benzenesulfonamide as a yellow solid (419 mg, 0.76 mmol, yield: 76%, 97% HPLC purity).
MS (ESI+) 553.6, (ESI−) 551.2.

Example 14

4-methyl-N-{3-[4-({methyl[4-(trifluoromethoxy)phenyl]amino}-methyl)phenyl]pyrazin-2-yl}benzenesulfonamide

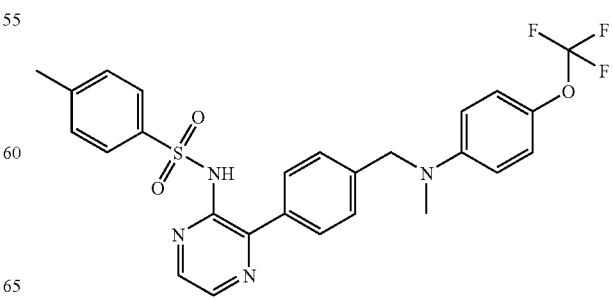

Following the general method as outlined in Example 1 (Method B), starting from N-{3-[4-(chloromethyl)phenyl]pyrazin-2-yl}-4-methylbenzenesulfonamide, and N-methyl-4-(trifluoromethoxy)aniline, the title compound was isolated as a yellow solid in 69% yield (94% purity by HPLC).

MS (ESI⁺): 529.5; MS (ESI⁻): 526.6.

Example 15

4-chloro-N-[3-(4-{[methyl(phenyl)amino]methyl}phenyl)pyrazin-2-yl]-benzenesulfonamide

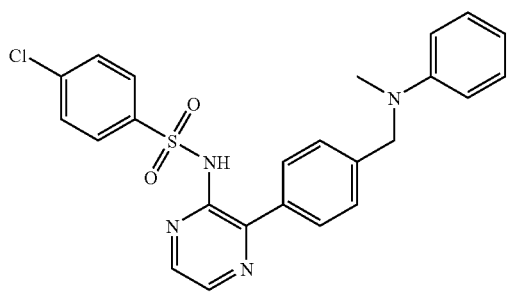 [SMILES: CN(Cc1ccc(-c2nccnc2NS(=O)(=O)c2ccc(Cl)cc2)cc1)c1ccccc1]

Following the general method as outlined in Example 1 (Method B), starting from 4-chloro-N-{3-[4-(chloromethyl)phenyl]pyrazin-2-yl}benzenesulfonamide, and N-methylaniline, the title compound was isolated as a yellow solid in 76% yield (96% purity by HPLC).

MS (ESI⁺): 465.6; MS (ESI⁻): 463.7.

Example 16

4-cyano-N-{3-[4-({methyl[4-(trifluoromethoxy)phenyl]amino}-methyl)phenyl]pyrazin-2-yl}benzenesulfonamide

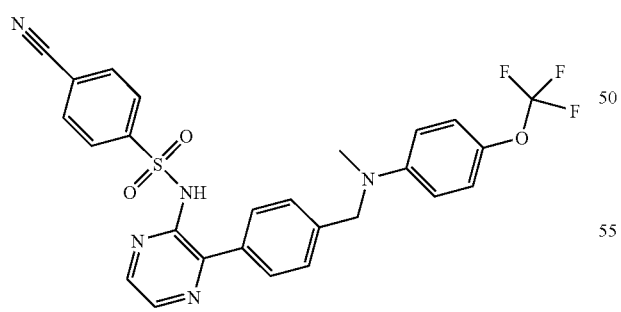

Following the general method as outlined in Example 1 (Method D), N-{3-[4-(chloromethyl)phenyl]pyrazin-2-yl}-4-cyanobenzenesulfonamide, and N-methyl-4-(trifluoromethoxy)aniline, the title compounds were isolated as a yellow solid in 70% yield (92% purity by HPLC).

MS (ESI⁺): 540.6; MS (ESI⁻): 538.5.

Example 17

N-[3-(4-{[(4-Fluoro-phenyl)-methyl-amino]-methyl}-phenyl)-pyrazin-2-yl]-2-trifluoromethyl-benzenesulfonamide

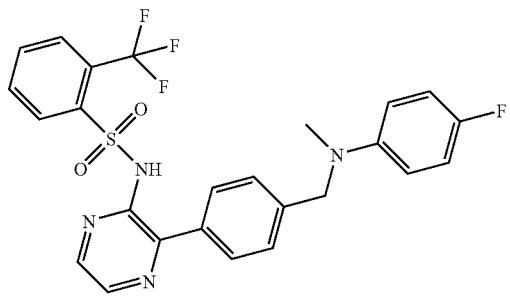 [SMILES: CN(Cc1ccc(-c2nccnc2NS(=O)(=O)c2ccccc2C(F)(F)F)cc1)c1ccc(F)cc1]

Following the general method as outlined in Example 1 (Method B), starting from N-{3-[4-(chloromethyl)phenyl]pyrazin-2-yl}-2-(trifluoromethyl)benzenesulfonamide (Intermediate 9), and 4-Fluoro-N-methylaniline, the title compound was isolated as a yellow solid in 78% yield (98% purity by HPLC).

MS (ESI⁺): 517.9; MS (ESI⁻): 515.8.

Example 18

N-(3-{4-[(Methyl-phenyl-amino)-methyl]-phenyl}-pyrazin-2-yl)-2-trifluoromethyl-benzenesulfonamide

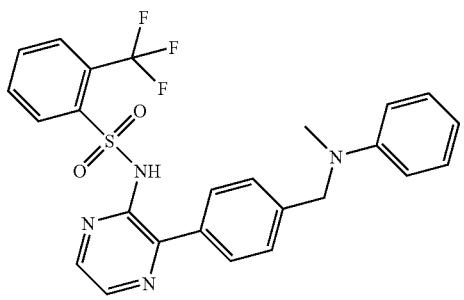 [SMILES: CN(Cc1ccc(-c2nccnc2NS(=O)(=O)c2ccccc2C(F)(F)F)cc1)c1ccccc1]

Following the general method as outlined in Example 1 (Method B), starting from N-{3-[4-(chloromethyl)phenyl]pyrazin-2-yl}-2-(trifluoromethyl)benzenesulfonamide (Intermediate 9), and N-methylaniline, the title compound was isolated as a yellow solid in 75% yield (99% purity by HPLC).

MS (ESI⁺): 499.9; MS (ESI⁻): 497.8.

Example 19

N-[3-(4-{[(4-Cyano-phenyl)-methyl-amino]-methyl}-phenyl)-pyrazin-2-yl]-2-trifluoromethyl-benzenesulfonamide

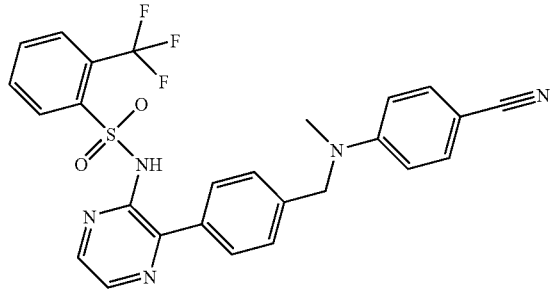

Following the general method as outlined in Example 1 (Method B), starting from N-{3-[4-(chloromethyl)phenyl]pyrazin-2-yl}-2-(trifluoromethyl)benzene sulfonamide (Intermediate 9), and 4-(N-methylamino)benzonitrile, the title compound was isolated as a yellow solid in 71% yield (94% purity by HPLC).

MS (ESI+): 524.6; MS (ESI−): 522.4.

Example 20

N-{3-[4-(4-Fluoro-phenoxymethyl)-phenyl]-pyrazin-2-yl}-2-trifluoromethyl-benzenesulfonamide

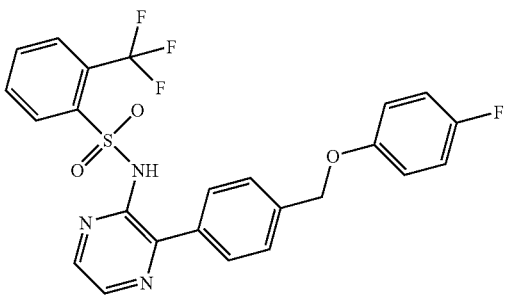

Following the general method as outlined in Example 1 (Method A), starting from N-{3-[4-(chloromethyl)phenyl]pyrazin-2-yl}-2-(trifluoromethyl)benzenesulfonamide (Intermediate 9), and 4-fluorophenol, the title compound was isolated as a yellow solid in 67% yield (95% purity by HPLC).

MS (ESI+): 504.6; MS (ESI−): 502.6.

Example 21

N-(3-{4-[(Ethyl-phenyl-amino)-methyl]-phenyl}-pyrazin-2-yl)-2-trifluoromethyl-benzenesulfonamide

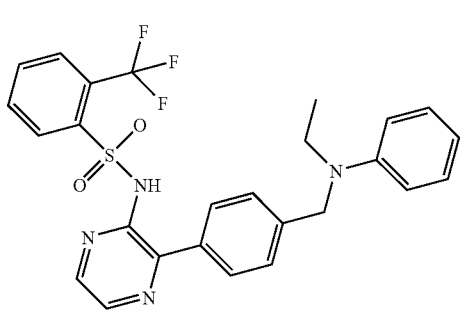

Following the general method as outlined in Example 1 (Method B), starting from N-{3-[4-(chloromethyl)phenyl]pyrazin-2-yl}-2-(trifluoromethyl)benzenesulfonamide (Intermediate 9), and N-ethylaniline, the title compound was isolated as a yellow solid in 70% yield (96% purity by HPLC).

MS (ESI+): 513.6; MS (ESI−): 511.7.

Example 22

N-{3-[4-(2,3-Dihydro-benzo[1,4]oxazin-4-ylmethyl)-phenyl]-pyrazin-2-yl}-2-trifluoromethyl-benzenesulfonamide

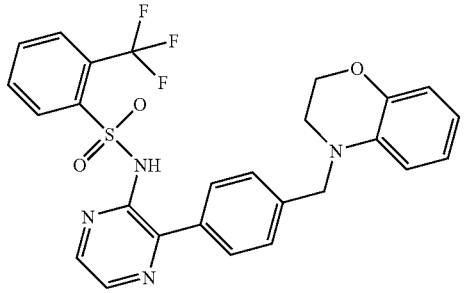

Following the general method as outlined in Example 1 (Method B), starting from N-{3-[4-(chloromethyl)phenyl]pyrazin-2-yl}-2-(trifluoromethyl)benzenesulfonamide (Intermediate 9), and 3,4-dihydro-2H-1,4-benzoxazine, the title compound was isolated as a yellow solid in 65% yield (97% purity by HPLC).

MS (ESI+): 527.7; MS (ESI−): 525.5.

Example 23

N-[3-(4-{[(3-Fluoro-phenyl)-methyl-amino]-methyl}-phenyl)-pyrazin-2-yl]-2-trifluoromethyl-benzenesulfonamide

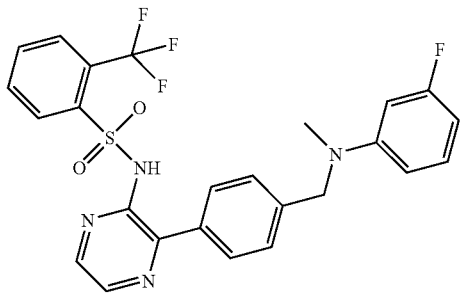

Following the general method as outlined in Example 1 (Method B), starting from N-{3-[4-(chloromethyl)phenyl]pyrazin-2-yl}-2-(trifluoromethyl)benzenesulfonamide (Intermediate 9), and 3-Fluoro-N-methylaniline, the title compound was isolated as a yellow solid in 69% yield (92% purity by HPLC).

MS (ESI$^+$): 517.7; MS (ESI$^-$): 515.6.

Example 24

N-{3-[4-(6-Chloro-pyridin-3-yloxymethyl)-phenyl]-pyrazin-2-yl}-2-trifluoromethyl-benzenesulfonamide

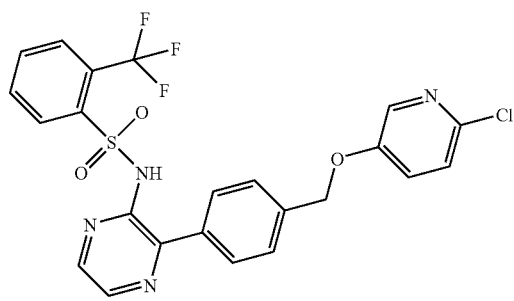

Following the general method as outlined in Example 1 (Method A), starting from N-{3-[4-(chloromethyl)phenyl]pyrazin-2-yl}-2-(trifluoromethyl)benzenesulfonamide (Intermediate 9), and 2-chloro-5-hydroxy-pyridine, the title compound was isolated as a yellow solid in 73% yield (98% purity by HPLC).

MS (ESI$^+$): 522.1; MS (ESI$^-$): 520.1.

Example 25

N-{3-[4-(2-Pyridin-2-yl-indol-1-ylmethyl)-phenyl]-pyrazin-2-yl}-2-trifluoromethyl-benzenesulfonamide

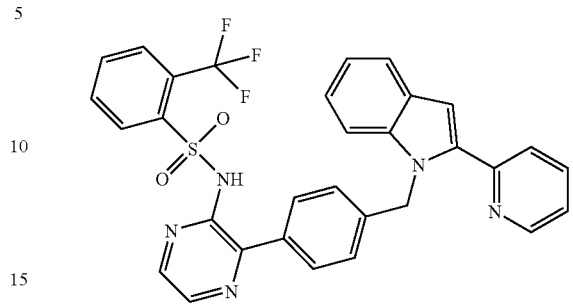

Following the general method as outlined in Example 1 (Method A), starting from N-{3-[4-(chloromethyl)phenyl]pyrazin-2-yl}-2-(trifluoromethyl)benzenesulfonamide (Intermediate 9), and 2-pyridine-2-yl-1H-indole, the title compound was isolated as a yellow solid in 56% yield (92% purity by HPLC).

MS (ESI$^+$): 586.8; MS (ESI$^-$): 584.6.

Example 26

N-{3-[4-(5-Fluoro-indol-1-ylmethyl)-phenyl]-pyrazin-2-yl}-2-trifluoromethyl-benzenesulfonamide

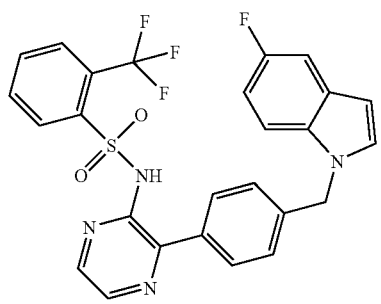

Following the general method as outlined in Example 1 (Method A), starting from N-{3-[4-(chloromethyl)phenyl]pyrazin-2-yl}-2-(trifluoromethyl)benzene sulfonamide (Intermediate 9), and 5-fluoro-indole, the title compound was isolated as a yellow solid in 69% yield (99% purity by HPLC).

MS (ESI$^+$): 527.6; MS (ESI$^-$): 525.7.

Example 27

N-[3-(4-Phenoxymethyl-phenyl)-pyrazin-2-yl]-2-trifluoromethyl-benzenesulfonamide

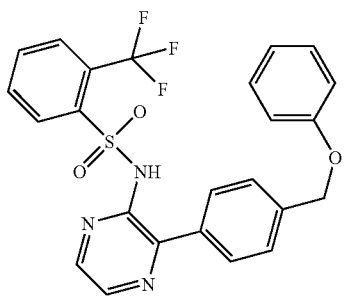

Following the general method as outlined in Example 1 (Method A), starting from N-{3-[4-(chloromethyl)phenyl]pyrazin-2-yl}-2-(trifluoromethyl)benzenesulfonamide (Intermediate 9), and phenol, the title compound was isolated as a yellow solid in 75% yield (98% purity by HPLC).

MS (ESI+): 486.8; MS (ESI−): 484.7.

Example 28

N-[3-(4-{[(4-Chloro-phenyl)-methyl-amino]-methyl}-phenyl)-pyrazin-2-yl]-2-trifluoromethyl-benzenesulfonamide

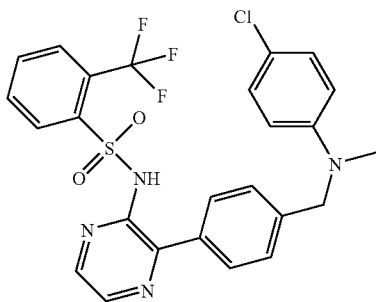

Following the general method as outlined in Example 1 (Method B), starting from N-{3-[4-(chloromethyl)phenyl]pyrazin-2-yl}-2-(trifluoromethyl)benzenesulfonamide (Intermediate 9), and 4-chloro-N-methylaniline, the title compound was isolated as a yellow solid in 72% yield (94% purity by HPLC).

MS (ESI+): 534.1; MS (ESI−): 532.1.

Example 29

2-Chloro-N-[3-(4-{[(4-cyano-phenyl)-methyl-amino]-methyl}-phenyl)-pyrazin-2-yl]-benzenesulfonamide

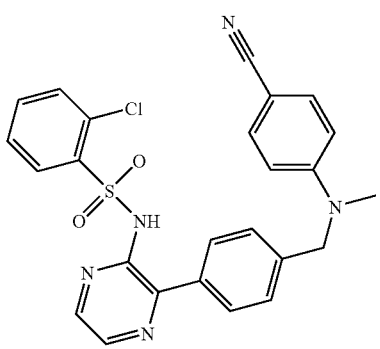

Following the general method as outlined in Example 1 (Method B), starting from N-{3-[4-(chloromethyl)phenyl]pyrazin-2-yl}-2-(chloro) benzenesulfonamide (Intermediate 8), and 4-(N-methylamino)-benzonitrile, the title compound was isolated as a yellow solid in 52% yield (99% purity by HPLC).

MS (ESI+): 491.0; MS (ESI−): 489.0.

Example 30

N-[3-(4-{[(3,4-Dichloro-phenyl)-methyl-amino]-methyl}-phenyl)-pyrazin-2-yl]-2-trifluoromethyl-benzenesulfonamide

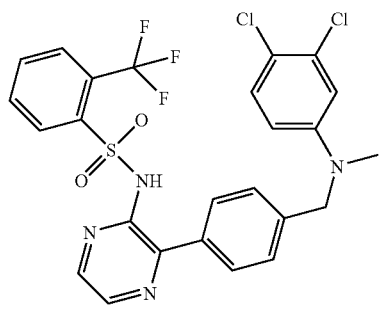

Following the general method as outlined in Example 1 (Method B), starting from N-{3-[4-(chloromethyl)phenyl]pyrazin-2-yl}-2-(trifluoromethyl)benzenesulfonamide (Intermediate 9), and 3,4-dichloro-N-methylaniline, the title compound was isolated as a yellow solid in 63% yield (91% purity by HPLC).

MS (ESI+): 569.6; MS (ESI−): 565.1.

Example 31

N-{3-[4-(4-Cyano-phenoxymethyl)-phenyl]-pyrazin-2-yl}-2-trifluoromethyl-benzenesulfonamide

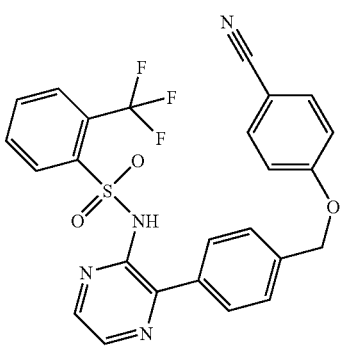

Following the general method as outlined in Example 1 (Method B), starting from N-{3-[4-(chloromethyl)phenyl]pyrazin-2-yl}-2-(trifluoromethyl)benzenesulfonamide (Intermediate 9), and 4-cyanophenol, the title compound was isolated as a yellow solid in 73% yield (93% purity by HPLC).

MS (ESI+): 511.6; MS (ESI−): 509.6.

Example 32

N-{3-[4-(6-Fluoro-indol-1-ylmethyl)-phenyl]-pyrazin-2-yl}-2-trifluoromethyl-benzenesulfonamide

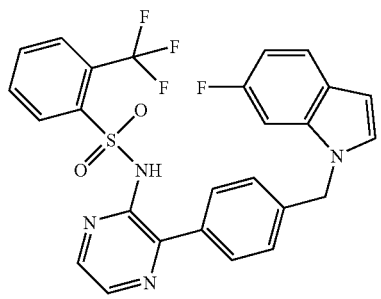

Following the general method as outlined in Example 1 (Method B), starting from N-{3-[4-(chloromethyl)phenyl]pyrazin-2-yl}-2-(trifluoromethyl)benzenesulfonamide (Intermediate 9), and 6-fluoro-1H-indole, the title compound was isolated as a yellow solid in 77% yield (97% purity by HPLC).

MS (ESI$^+$): 527.8; MS (ESI$^-$): 525.6.

Example 33

2-Chloro-N-{3-[4-(5-methoxy-2-methyl-indol-1-ylmethyl)-phenyl]-pyrazin-2-yl}-benzenesulfonamide

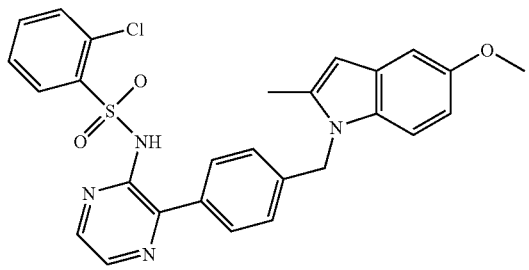

Following the general method as outlined in Example 1 (Method B), starting from N-{3-[4-(chloromethyl)phenyl]pyrazin-2-yl}-2-(chloro) benzenesulfonamide (Intermediate 8), and 2-methyl-5-methoxyindole, the title compound was isolated as a yellow solid in 72% yield (98% purity by HPLC).

MS (ESI$^+$): 520.2; MS (ESI$^-$): 518.3.

Example 34

N-{3-[4-(4-Methoxy-phenoxymethyl)-phenyl]-pyrazin-2-yl}-2-trifluoromethyl-benzenesulfonamide

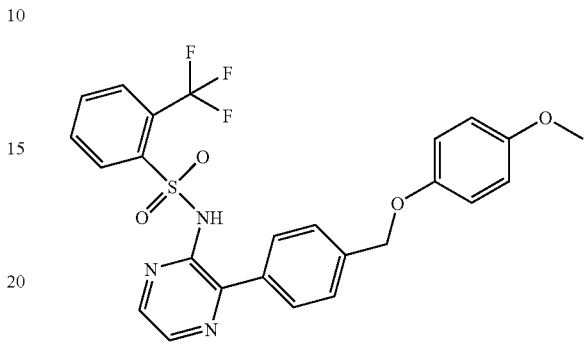

Following the general method as outlined in Example 1 (Method 8), starting from N-{3-[4-(chloromethyl)phenyl]pyrazin-2-yl}-2-(trifluoromethyl)benzenesulfonamide (Intermediate 9), and 4-hydroxyanisole, the title compound was isolated as a yellow solid in 48% yield (91% purity by HPLC).

MS (ESI$^+$): 516.6; MS (ESI$^-$): 514.5.

Example 35

N-(3-{4-[(Benzyl-pyridin-2-yl-amino)-methyl]-phenyl}-pyrazin-2-yl)-2-chloro-benzenesulfonamide

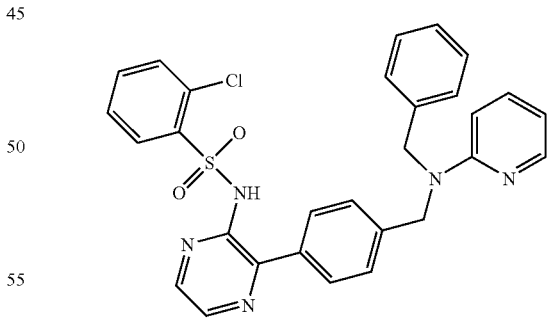

Following the general method as outlined in Example 1 (Method B), starting from N-{3-[4-(chloromethyl)phenyl]pyrazin-2-yl}-2-(chloro) benzenesulfonamide (Intermediate 8), and 2-benzylaminopyridine, the title compound was isolated as a yellow solid in 35% yield (94% purity by HPLC).

MS (ESI$^+$): 543.3; MS (ESI$^-$): 541.3.

Example 36

N-{3-[4-(2,3-Dihydro-indol-1-ylmethyl)-phenyl]-pyrazin-2-yl}-2-trifluoromethyl-benzenesulfonamide

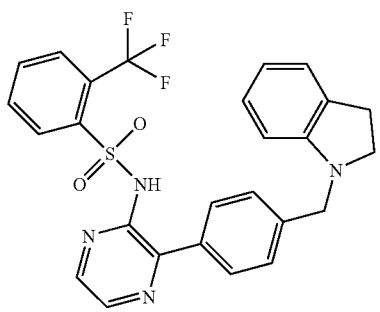

Following the general method as outlined in Example 1 (Method B), starting from N-{3-[4-(chloromethyl)phenyl]pyrazin-2-yl}-2-(trifluoromethyl)benzenesulfonamide (Intermediate 9), and 2,3-dihydro-1H-indole, the title compound was isolated as a yellow solid in 66% yield (94% purity by HPLC).

MS (ESI$^+$): 511.6; MS (ESI$^-$): 509.4.

Example 37

N-[3-(4-{[(2,4-Dichloro-phenyl)-methyl-amino]-methyl}-phenyl)-pyrazin-2-yl]-2-trifluoromethyl-benzenesulfonamide

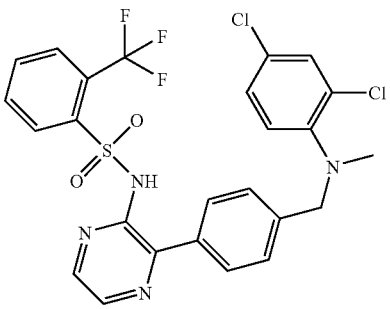

Following the general method as outlined in Example 1 (Method B), starting from N-{3-[4-(chloromethyl)phenyl]pyrazin-2-yl}-2-(trifluoromethyl)benzenesulfonamide (Intermediate 9), and 2,4-dichloro-N-methylaniline, the title compound was isolated as a yellow solid in 69% yield (96% purity by HPLC).

MS (ESI$^+$): 569.6; MS (ESI$^-$): 566.8.

Example 38

N-{3-[4-(3-Chloro-phenoxymethyl)-phenyl]-pyrazin-2-yl}-2-trifluoromethyl-benzenesulfonamide

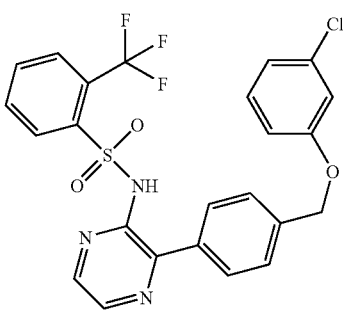

Following the general method as outlined in Example 1 (Method A), starting from N-{3-[4-(chloromethyl)phenyl]pyrazin-2-yl}-2-(trifluoromethyl)benzenesulfonamide (Intermediate 9), and 3-chlorophenol, the title compound was isolated as a yellow solid in 70% yield (98% purity by HPLC).

MS (ESI$^+$): 521.0; MS (ESI$^-$): 519.0.

Example 39

2-Chloro-N-[3-(4-{[(2,4-difluoro-phenyl)-methyl-amino]-methyl}-phenyl)-pyrazin-2-yl]-benzene-sulfonamide

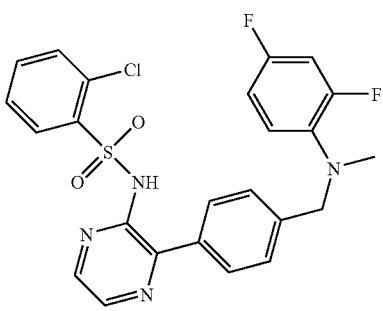

Following the general method as outlined in Example 1 (Method B), starting from N-{3-[4-(chloromethyl)phenyl]pyrazin-2-yl}-2-(chloro)benzenesulfonamide (Intermediate 8), and 2,4-difluoro-N-methylaniline, the title compound was isolated as a yellow solid in 77% yield (92% purity by HPLC).

MS (ESI$^+$): 502.0; MS (ESI$^-$): 500.0.

Example 40

N-{3-[4-(2-Methyl-indol-1-ylmethyl)-phenyl]-pyrazin-2-yl}-2-trifluoromethyl-benzenesulfonamide

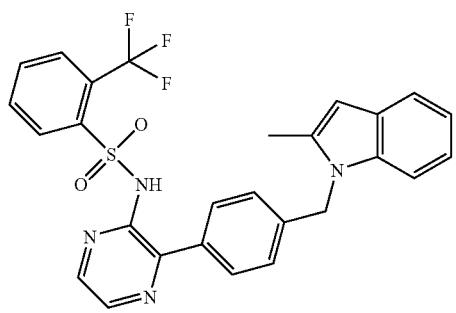

Following the general method as outlined in Example 1 (Method A), starting from N-{3-[4-(chloromethyl)phenyl]pyrazin-2-yl}-2-(trifluoromethyl)benzenesulfonamide (Intermediate 9), and 2-methyl-1-H-indole, the title compound was isolated as a yellow solid in 70% yield (98% purity by HPLC).

MS (ESI$^+$): 523.5; MS (ESI$^-$): 521.5.

Example 41

2-Chloro-N-{3-[4-(5-fluoro-indol-1-ylmethyl)-phenyl]-pyrazin-2-yl}-benzenesulfonamide

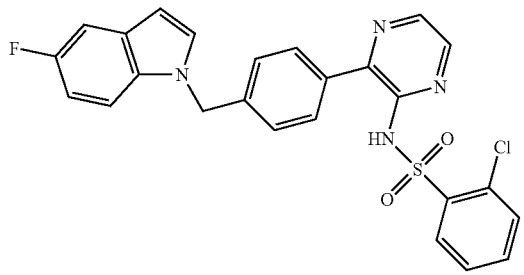 [SMILES: O=S(=O)(Nc1nccnc1-c1ccc(Cn2ccc3cc(F)ccc32)cc1)c1ccccc1Cl]

Following the general method as outlined in Example 1 (Method B), starting from 2-chloro-N-{3-[4-(chloromethyl)phenyl]pyrazin-2-yl}benzenesulfonamide (Intermediate 8), and 5-fluoroindole, the title compound was isolated as a yellow solid in 72% yield (96% purity by HPLC).

MS (ESI$^+$): 493.9; MS (ESI$^-$): 491.9

Example 42

2-Chloro-N-[3-(4-{[(2-fluoro-phenyl)-methyl-amino]-methyl}-phenyl)-pyrazin-2-yl]-benzenesulfonamide

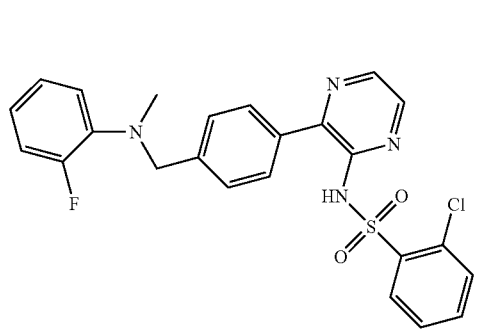 [SMILES: CN(Cc1ccc(-c2nccnc2NS(=O)(=O)c2ccccc2Cl)cc1)c1ccccc1F]

Following the general method as outlined in Example 1 (Method B), starting from 2-chloro-N-{3-[4-(chloromethyl)phenyl]pyrazin-2-yl}benzene sulfonamide (Intermediate 8), and 2-fluoro-N-methyl-aniline, the title compound was isolated as a yellow solid in 79% yield (99% purity by HPLC).

MS (ESI$^+$): 484.1; MS (ESI$^-$): 482.1

Example 43

2-Chloro-N-{3-[4-(2-methyl-indol-1-ylmethyl)-phenyl]-pyrazin-2-yl}-benzenesulfonamide

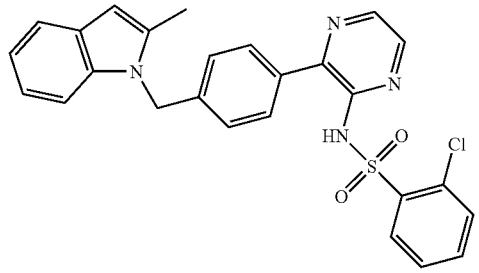 [SMILES: Cc1cc2ccccc2n1Cc1ccc(-c2nccnc2NS(=O)(=O)c2ccccc2Cl)cc1]

Following the general method as outlined in Example 1 (Method B), starting from 2-chloro-N-{3-[4-(chloromethyl)phenyl]pyrazin-2-yl}benzenesulfonamide (Intermediate 8), and 2-methyl-1-H-indole, the title compound was isolated as a yellow solid in 81% yield (96% purity by HPLC).

MS (ESI$^+$): 490.0; MS (ESI$^-$): 488.1

Example 44

N-(3-{4-[(Benzyl-pyridin-2-yl-amino)-methyl]-phenyl}-pyrazin-2-yl)-2-trifluoromethyl-benzenesulfonamide

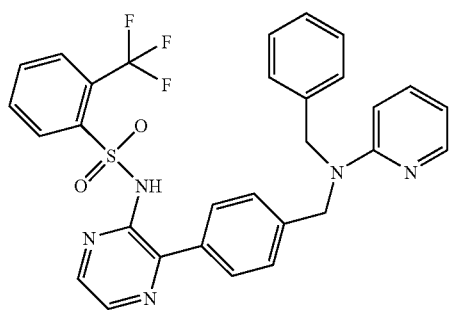

Following the general method as outlined in Example 1 (Method A), starting from N-{3-[4-(chloromethyl)phenyl]pyrazin-2-yl}-2-(trifluoromethyl)benzenesulfonamide (Intermediate 9), and N-(2-pyridine)-benzylamine, the title compound was isolated as a yellow solid in 79% yield (98% purity by HPLC).

MS (ESI$^+$): 576.6; MS (ESI$^-$): 574.6.

Example 45

2-Chloro-N-(3-{4-[(ethyl-pyridin-2-yl-amino)-methyl]-phenyl}-pyrazin-2-yl)-benzenesulfonamide

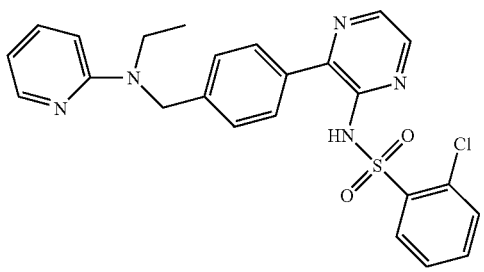 [SMILES: CCN(Cc1ccc(-c2nccnc2NS(=O)(=O)c2ccccc2Cl)cc1)c1ccccn1]

Following the general method as outlined in Example 1 (Method B), starting from 2-chloro-N-{3-[4-(chloromethyl)phenyl]pyrazin-2-yl}benzenesulfonamide (Intermediate 8), and 2-(ethylamino)-pyridine, the title compound was isolated as a yellow solid in 64% yield (96% purity by HPLC).

MS (ESI$^+$): 481.0; MS (ESI$^-$): 478.1

Example 46

N-{3-[4-(5-Chloro-2-methyl-indol-1-ylmethyl)-phenyl]-pyrazin-2-yl}-2-trifluoromethyl-benzenesulfonamide

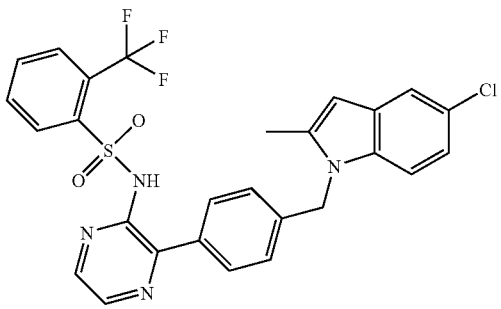

Following the general method as outlined in Example 1 (Method A), starting from N-{3-[4-(chloromethyl)phenyl]pyrazin-2-yl}-2-(trifluoromethyl)benzenesulfonamide (Intermediate 9), and 2-methyl-5-chloroindole, the title compound was isolated as a yellow solid in 71% yield (95% purity by HPLC).

MS (ESI$^+$): 558.3; MS (ESI$^-$): 556.4.

Example 47

Preparation of a Pharmaceutical Formulation

The following formulation examples illustrate representative pharmaceutical compositions according to the present invention being not restricted thereto.

Formulation 1—Tablets

A 2,3-substituted pyrazine sulfonamide derivative of formula I is admixed as a dry powder with a dry gelatin binder in an approximate 1:2 weight ratio. A minor amount of magnesium stearate is added as a lubricant. The mixture is formed into 240-270 mg tablets (80-90 mg of active 2,3-substituted pyrazine sulfonamide compound per tablet) in a tablet press.

Formulation 2—Capsules

A 2,3-substituted pyrazine sulfonamide derivative of formula I is admixed as a dry powder with a starch diluent in an approximate 1:1 weight ratio. The mixture is filled into 250 mg capsules (125 mg of active 2,3-substituted pyrazine sulfonamide compound per capsule).

Formulation 3—Liquid

A 2,3-substituted pyrazine sulfonamide derivative of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 4—Tablets

A 2,3-substituted pyrazine sulfonamide derivative of formula I is admixed as a dry powder with a dry gelatin binder in an approximate 1:2 weight ratio. A minor amount of magnesium stearate is added as a lubricant. The mixture is formed into 450-900 mg tablets (150-300 mg of active 2,3-substituted pyrazine sulfonamide compound) in a tablet press.

Formulation 5—Injection

A 2,3-substituted pyrazine sulfonamide derivative of formula (I) is dissolved in a buffered sterile saline injectable aqueous medium to a concentration of approximately 5 mg/ml.

Biological Assays

Example 48

Construction of pCEP4-hCRTH2 Mammalian Expression Vector

Human CRTH2 cDNA was amplified by PCR using a human urinary bladder cDNA library as a template and specific primers containing HindIII and BamHI restriction sites for cloning into the pCEP4 vector (Invitrogen). The vector construction is described in detail in Sawyer et al., Br. J. Pharmocol 2002, 137, 1163-72. The nucleotide sequence of the cloned cDNA was identical the previously reported hCRTH2 sequence (Nagata et al, 1999, J. Immunol. 162, 1278-1286).

Example 49

Establishment of a pCEP4-hCRTH2-HEK293 (EBNA) Cell Line

HEK293 (EBNA) cells were transfected with the pCEP4-hCRTH2 construct using the calcium phosphate technique. Cells were maintained in culture at 37° C. in an atmosphere of 5% $CO_2$ in Dulbecco's modified Eagle's F12 medium (Invitrogen), containing 10% heat-inactivated foetal calf serum (TerraCell International, Canada), 2 mM Glutamine, 100 units/ml of penicillin and 100 µg/ml streptomycin (Invitrogen). 48 hours after the transfection, cells were grown in presence of 300 µg/ml of Hygromycin B (Invitrogen) for 4 weeks and antibiotic resistant cells were amplified for cell membrane preparation.

Example 50

Preparation of hCRTH2-Expressing Membranes

Adherent HEK293 (EBNA) cells expressing hCRTH2 were cultured in 225 cm² cell culture flasks (Corning, USA) in 30 ml of medium. After two rinses of phosphate buffered saline (PBS), cells were harvested in 10 ml of PBS containing 1 mM EDTA, centrifuged at 500×g for 5 min at 4° C. and frozen at −80° C. The pellet was re-suspended in 50 mM Tris-HCl, pH 7.4, 2 mM EDTA, 250 mM Sucrose, containing protease inhibitor cocktail tablets, (Complete EDTA-free, Roche, Germany) and incubated 30 min at 4° C. Cells were disrupted by nitrogen cavitation (Parr Instruments, USA) at 4° C. (800 p.s.i. for 30 min), and centrifuged at 500×g for 10 min at 4° C. Pellet containing nuclei and cellular debris was discarded and supernatant was centrifuged 60 min at 4° C. at 45000×g. Membrane pellet was re-suspended in storage buffer (10 mM HEPES/KOH pH 7.4, 1 mM EDTA, 250 mM sucrose, protease inhibitor cocktail tablets) using Dounce homogenization and frozen in liquid nitrogen, and stored at −80° C.

Example 51

Radioligand Binding Assay

The compounds of the present invention inhibit the binding of PGD2 to its receptor CRTH2. The inhibitory activity can be investigated by a radioligand binding assay (Sawyer et al., Br. J. Pharmocol 2002, 137, 1163-72). The radioligand binding assay was performed at room temperature in binding buffer (10 mM HEPES/KOH pH 7.4, mM $MnCl_2$, with protease inhibitor cocktail tablets), containing 1.5 nM [$^3$H]$PGD_2$ (Amersham, 156 Cie/mmol), and 10 µg of hCRTH2 HEK293 (EBNA) cell membrane protein in a final volume of 100 µl in 96 well plates (Corning, USA). Non-specific binding was determined in the presence of 1 µM $PGD_2$ (Cayman, USA). Competing pyrazine sulfonamides were diluted in dimethylsulphoxide so that the total volume of dimethylsulfoxide was kept constant at 1% dimethylsulphoxide ($Me_2SO$). 10 µl of the pyrazine sulfonamides were added. Incubation (60 min at room temperature) was terminated by rapid filtration through 96 wells hydrophobic GF/C Unifilter plates (Whatman, USA). Filters were washed twice with 250 µl of Tris-HCl pH 7.4, 10 mM MnCl2, and residual radioligand bound to the filters was mixed to 100 µl of liquid scintillation cocktail (Optiphase Supermix, Perkin Elmer, USA) and binding activity was determined by counting residual radioligand using a 1450 Micro-beta scintillation counter (Wallac, UK). Results of the binding assay are shown in Table 1.

TABLE 1

| Compound No. | Name | Structure | Inhibition hCRTH2 [%] |
|---|---|---|---|
| 1 | N-{3-[4-(1H-indol-1-ylmethyl)phenyl]pyrazin-2-yl}-2-(trifluoromethyl)benzenesulfonamide | 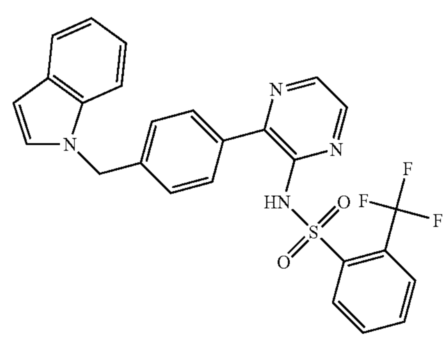 [SMILES: O=S(=O)(Nc1nccnc1-c1ccc(Cn2ccc3ccccc32)cc1)c1ccccc1C(F)(F)F] | 94.5 |

TABLE 1-continued

| Compound No. | Name | Structure | Inhibition hCRTH2 [%] |
|---|---|---|---|
| 2 | 2-chloro-N-{3-[4-({methyl[4-(trifluoromethoxy)phenyl]amino}-methyl)phenyl]pyrazin-2-yl}benzenesulfonamide | 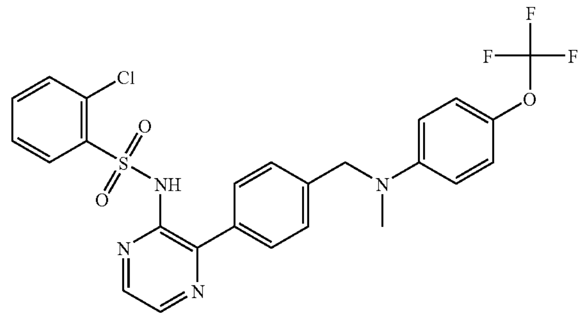 [SMILES: CN(Cc1ccc(-c2nccnc2NS(=O)(=O)c2ccccc2Cl)cc1)c1ccc(OC(F)(F)F)cc1] | 91.5 |
| 3 | N-(3-{4-[(2-ethyl-1H-benzimidazol-1-yl)methyl]phenyl}pyrazin-2-yl)-2-(trifluoromethyl)benzene-sulfonamide | 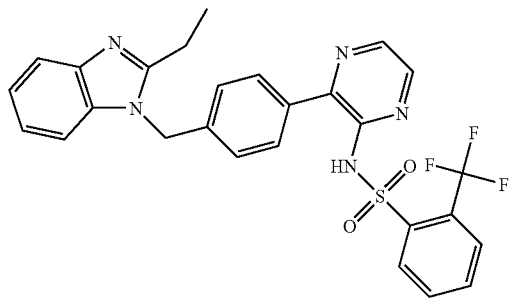 [SMILES: CCc1nc2ccccc2n1Cc1ccc(-c2nccnc2NS(=O)(=O)c2ccccc2C(F)(F)F)cc1] | 86.5 |
| 4 | 2-chloro-N-[3-(4-{[methyl(phenyl)amino]methyl}phenyl)pyrazin-2-yl]benzenesulfonamide | 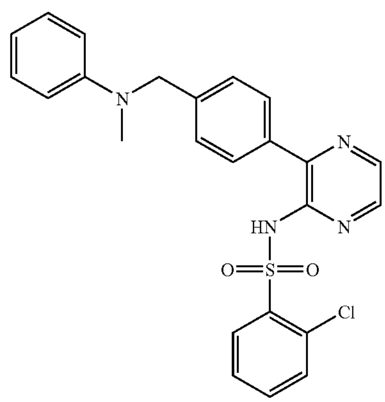 [SMILES: CN(Cc1ccc(-c2nccnc2NS(=O)(=O)c2ccccc2Cl)cc1)c1ccccc1] | 84.5 |
| 5 | 2-chloro-N-(3-{4-[(2-naphthyloxy)methyl]phenyl}pyrazin-2-yl)-benzenesulfonamide | 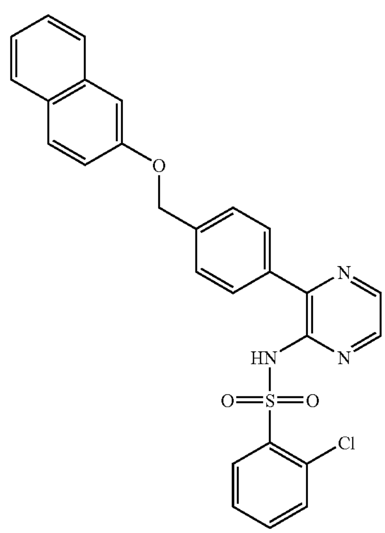 [SMILES: O=S(=O)(Nc1nccnc1-c1ccc(COc2ccc3ccccc3c2)cc1)c1ccccc1Cl] | 82.0 |

TABLE 1-continued

| Compound No. | Name | Structure | Inhibition hCRTH2 [%] |
|---|---|---|---|
| 6 | 2-chloro-N-{3-[4-(1H-indol-1-ylmethyl)phenyl]-pyrazin-2-yl}-benzenesulfonamide | 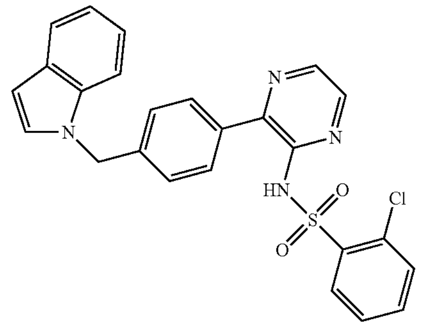 [SMILES: O=S(=O)(Nc1nccnc1-c1ccc(Cn2ccc3ccccc32)cc1)c1ccccc1Cl] | 81.5 |
| 7 | 2-chloro-N-(3-{4-[(5,6,7,8-tetrahydronaphthalen-2-yloxy)methyl]-phenyl}pyrazin-2-yl)benzenesulfonamide | 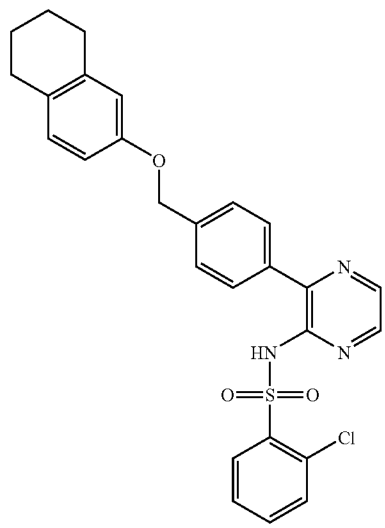 [SMILES: O=S(=O)(Nc1nccnc1-c1ccc(COc2ccc3c(c2)CCCC3)cc1)c1ccccc1Cl] | 80.0 |
| 8 | 2-chloro-N-(3-{4-[(2-ethyl-1H-benzimidazol-1-yl)methyl]phenyl}pyrazin-2-yl)benzenesulfonamide | 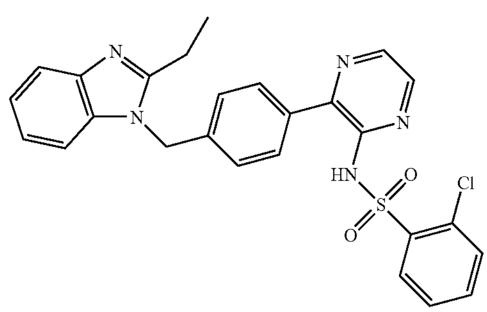 [SMILES: CCc1nc2ccccc2n1Cc1ccc(-c2nccnc2NS(=O)(=O)c2ccccc2Cl)cc1] | 79.0 |

TABLE 1-continued

| Compound No. | Name | Structure | Inhibition hCRTH2 [%] |
|---|---|---|---|
| 9 | N-(3-{4-[(1,3-benzodioxol-5-ylamino)methyl]-phenyl}pyrazin-2-yl)-2-(trifluoromethyl)benzenesulfonamide | 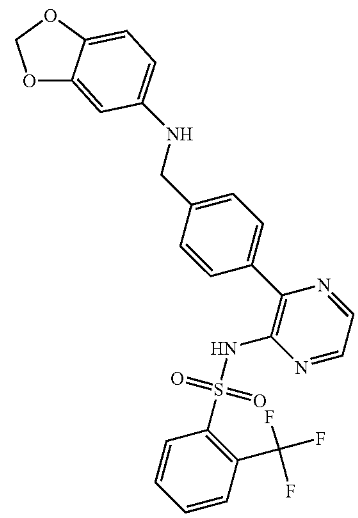 [SMILES: O=S(=O)(Nc1nccnc1-c1ccc(CNc2ccc3c(c2)OCO3)cc1)c1ccccc1C(F)(F)F] | 72.5 |
| 10 | N-[3-(4-{[(3-methoxybenzyl)oxy]methyl}phenyl)pyrazin-2-yl]-2-(trifluoromethyl)benzenesulfonamide | 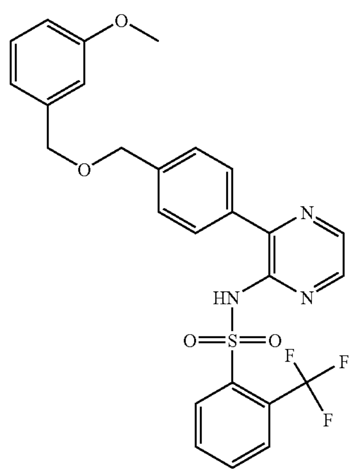 [SMILES: COc1cccc(COCc2ccc(-c3nccnc3NS(=O)(=O)c3ccccc3C(F)(F)F)cc2)c1] | 72.0 |
| 11 | 3-chloro-N-{3-[4-({methyl[4-(trifluoromethoxy)phenyl]-amino}-methyl)phenyl]pyrazin-2-yl}benzenesulfonamide | 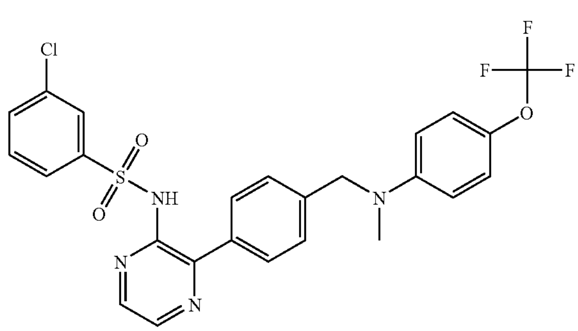 [SMILES: CN(Cc1ccc(-c2nccnc2NS(=O)(=O)c2cccc(Cl)c2)cc1)c1ccc(OC(F)(F)F)cc1] | 65.0 |

TABLE 1-continued

| Compound No. | Name | Structure | Inhibition hCRTH2 [%] |
|---|---|---|---|
| 12 | N-[3-(4-{[(4-chlorophenyl)(methyl)amino]-methyl}phenyl)pyrazin-2-yl]-thiophene-2-sulfonamide | 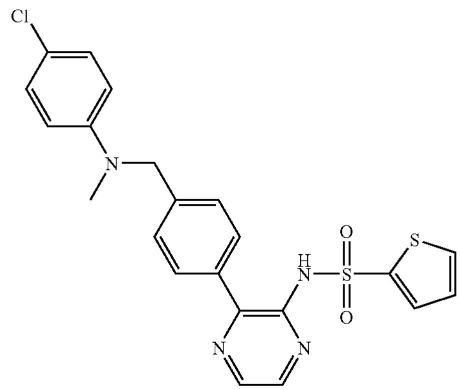 [SMILES: CN(Cc1ccc(-c2nccnc2NS(=O)(=O)c2cccs2)cc1)c1ccc(Cl)cc1] | 65.0 |
| 13 | 4-phenoxy-N-{3-[4-(quinolin-2-ylmethyl)piperazin-1-yl]pyrazin-2-yl}-benzenesulfonamide | 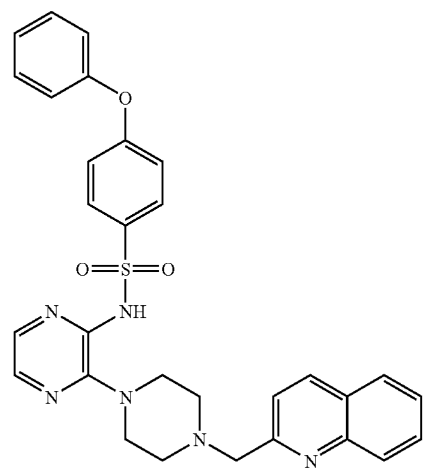 [SMILES: O=S(=O)(Nc1nccnc1N1CCN(Cc2ccc3ccccc3n2)CC1)c1ccc(Oc2ccccc2)cc1] | 64.5 |
| 14 | 4-methyl-N-{3-[4-({methyl[4-(trifluoromethoxy)phenyl]-amino}-methyl)phenyl]pyrazin-2-yl}benzenesulfonamide | 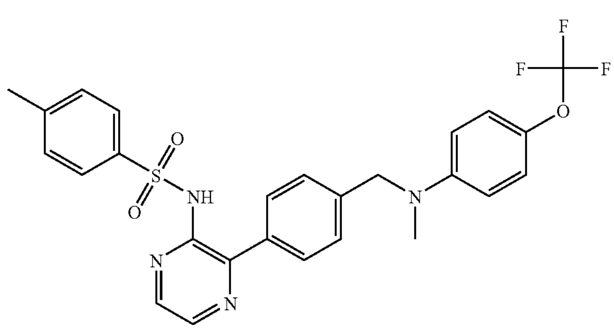 [SMILES: Cc1ccc(S(=O)(=O)Nc2nccnc2-c2ccc(CN(C)c3ccc(OC(F)(F)F)cc3)cc2)cc1] | 53.0 |

TABLE 1-continued

| Compound No. | Name | Structure | Inhibition hCRTH2 [%] |
|---|---|---|---|
| 15 | 4-chloro-N-[3-(4-{[methyl(phenyl)amino]methyl}phenyl)pyrazin-2-yl]-benzenesulfonamide | 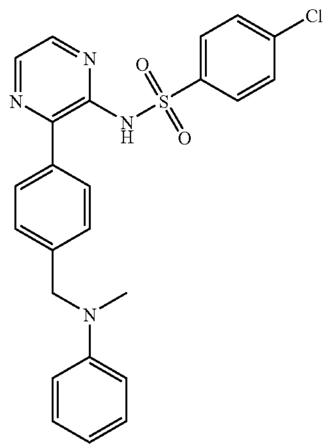 [SMILES: CN(Cc1ccc(-c2nccnc2NS(=O)(=O)c2ccc(Cl)cc2)cc1)c1ccccc1] | 51.0 |
| 16 | 4-cyano-N-{3-[4-({methyl[4-(trifluoromethoxy)phenyl]-amino}methyl)phenyl]pyrazin-2-yl}benzenesulfonamide | 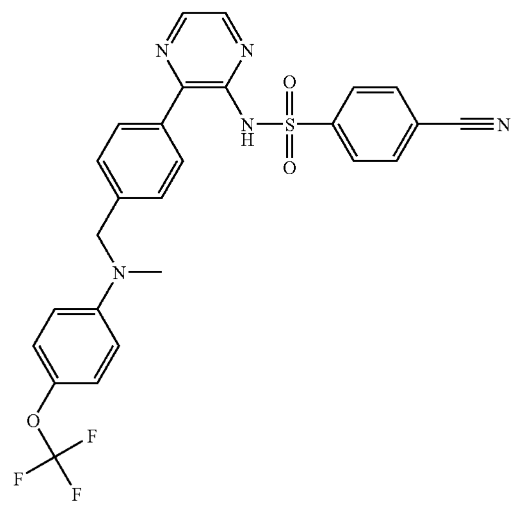 [SMILES: CN(Cc1ccc(-c2nccnc2NS(=O)(=O)c2ccc(C#N)cc2)cc1)c1ccc(OC(F)(F)F)cc1] | 47.0 |

Example 52

Determination of $K_i$

Radioligand Binding Assay $K_i$ values were determined by equilibrium competition binding experiments against [$^3$H]PGD$_2$. $K_i$ values were calculated from the formula below and represent the average of at least three independent dose response experiments. The $K_i$ values give the ligand concentrations necessary to inhibit 50% of the binding of 3[H]PGD$_2$ to CRTH2. $K_i$=IC$_{50}$/(1+ [Concentration of Ligand]/K$_d$)]

All experiments were performed in 96 well plates, in a final volume of 100 μl according to the above described filtration assay. The concentration of membranes and 3[H]PGD$_2$, as well as the positive and negative controls were identical to the conditions described above.

In one embodiment, the pyrazine sulfonamides of the present invention inhibit CRTH2 at a concentration of <100 μM. In another embodiment, the pyrazine sulfonamides of the present invention inhibit CRTH2 at a concentration of <10 μM. In a preferred embodiment, the pyrazine sulfonamides of the present invention inhibit CRTH2 at a concentration of <5 μM. In a further preferred embodiment, the pyrazine sulfonamides of the present invention inhibit CRTH2 at a concentration of <1 μM.

$K_i$ values are shown in Table 2. It can be derived that said compounds according to Formula I showed a significant inhibition of the binding of PGD2 to CRTH2.

TABLE 2

| Compound No. | $K_i$[μM] |
|---|---|
| 1 | 1.01 |
| 2 | 1.26 |
| 3 | 0.45 |
| 4 | 1.57 |
| 5 | 2.32 |
| 6 | 2.12 |
| 7 | 2.59 |
| 8 | 1.42 |
| 9 | 2.98 |
| 10 | 1.40 |
| 11 | 5.16 |
| 12 | 8.43 |
| 13 | 4.03 |
| 14 | 5.85 |
| 15 | 5.38 |

TABLE 2-continued

| Compound No. | $K_i[\mu M]$ |
|---|---|
| 16 | 5.71 |
| 17 | 0.38 |
| 18 | 0.40 |
| 19 | 0.47 |
| 20 | 0.48 |
| 21 | 0.59 |
| 22 | 0.62 |
| 23 | 0.70 |
| 24 | 0.72 |
| 25 | 0.85 |
| 26 | 0.95 |
| 27 | 1.32 |
| 28 | 1.47 |
| 29 | 1.49 |
| 30 | 1.58 |
| 31 | 1.59 |
| 32 | 1.93 |
| 33 | 2.21 |
| 34 | 2.60 |
| 35 | 2.64 |
| 36 | 2.69 |
| 37 | 2.82 |
| 38 | 2.90 |
| 39 | 2.95 |
| 40 | 3.06 |
| 41 | 3.90 |
| 42 | 3.90 |
| 43 | 4.11 |
| 44 | 4.44 |
| 45 | 4.51 |
| 46 | 4.65 |

Example 53

[$^{35}$S]GTPγS Binding Assay

The [$^{35}$S]GTPγS assay measures the increase in guanine nucleotide exchange at G-proteins in cell membranes, resulting from agonist (PGD2) binding to CRTH2. This process can be monitored in vitro by incubating cell membranes containing G-proteins and CRTH2 with GDP and [$^{35}$S]GTPγS, a radiolabeled, hydrolysis-resistant analogue of GTP (see, Harrison et al., Life Sciences 74, 489-508, 2003). The addition of a pyrazine sulfonamide results in binding to CRTH2 and thus in an inhibition of agonist binding, which can be monitored as inhibition of the stimulation of GTP/GDP exchange.

Assay conditions were identical to conditions of radioligand binding assay as described in Example 21. The [$^{35}$S] GTPγS binding assay was performed at 30° C. with gentle agitation in 96-well scintillating white polystyrene plates (Perkin Elmer, USA), in a final volume of 200 μl, containing 2% of dimethylsulphoxide (Me$_2$SO). The 2,3 substituted pyrazine sulfonamides were incubated in 20 mM HEPES/KOH pH 7.4, 1 mM MgCl$_2$, 10 μg/ml Saponin, 3 μM GDP, 150 mM NaCl containing 10 μg of membranes expressing the hCRTH2 receptor (Euroscreen, Belgium) for 10 min. Non-specific binding was determined in the presence of 10 μM of GTPγS. Samples were incubated for 30 min in the presence of increasing concentrations of PGD$_2$ for the determination of agonist activity, or with 80 nM of PGD$_2$ for determination of antagonist activity, respectively. 0.15 nM of [$^{35}$S]GTPγS were subsequently added to each sample and after incubation of 30 min reactions were stopped by centrifugation at 1000× g, at 4° C. for 10 min. Supernatant was removed and [$^{35}$S] GTPγS binding was determined using a 1450 Micro-beta scintillation counter. Data were analysed using "Prism" (GraphPad Software, Inc. San Diego, USA). The determination of the IC50 values (i.e. the amount necessary to achieve 50% inhibition of binding (in μM)) were performed in 96 well plates, in a final volume of 100 μl according to the above described filtration assay. The concentration of membranes and radioactive ligand, as well as the positive and negative controls were identical to the conditions used and described above Examples 21 and 22.

The compound of Example 1 showed an IC50 value of 1.9 μM. The compound of Example 2 showed an IC50 value of 4.6 μM and the compound of Example 3 showed an IC50 value of 1.4 μM.

Example 54

CHS Model

The contact hypersensitivity model can be used to evaluate the therapeutic efficacy of 2,3-substituted pyrazine sulfonamides on skin inflammation mediated by T cells. The model is well established for characterization of compound for dermatological indications like psoriasis and allergic contact dermatitis (Xu et al. J Exp Med. 183, 1001-12, 1996). It involves a sensitization phase and a subsequent challenge with an antigen (DNFB, 2,4-dinitrofluorobenzene). This results in skin inflammation with formation of edema and cellular infiltrates in the skin. The edema can be measured by caliper at the challenged site (ear of the mice). Intravenous administration of the compounds of the invention 30 min before challenge with DNFB results in a decrease of the swelling and therefore reduces inflammation in the skin compared to positive controls treated with vehicle only before challenge with the antigen. Negative control mice are not sensitized, but challenged with DNFB, therefore no T cell dependent inflammation occurs and no edema is formed. Balb/c mice are obtained from CharlesRiver (Calcco, Italy). Animals are housed in a conventional animal facility. Treatment starts at an average age of 8-12 weeks.

DNFB (2,4-dinitrofluorobenzene) is purchased from Sigma-Aldrich (St. Louis, Mo. USA)

Sensitization and Challenge of CHS by DNFB

Mice are sensitized and challenged to elicit CHS to DNFB. The sensitization phase is followed by a challenge phase. DNFB is diluted in acetone/olive oil (4/1) immediately before use. Mice are sensitized to DNFB by applying 25 μl of 0.5% DNFB solution onto the shaved dorsal skin. Five days later, 10 μl of 0.2% DNFB are applied onto both sides of the right ear (challenge). Ear thickness is monitored on day 6 (1 day after challenge) using a caliper (Mitutoyo, Milan, Italy). Ear swelling is calculated as ((Tn−T5) right ear−(Tn−T5) left ear), wherein Tn and T5 represent values of ear thickness at day n of investigation and day 5 prior to challenge, respectively.

REFERENCE LIST

Cosmi et al. (2000) Eur. J. Immunol. 30, 2972-2979
Bush, R. K., Georgitis J. W., Handbook of asthma and rhinitis. 1st ed. (1997), Abingdon: Blackwell Science. 270
Harrison et al. (2003) Life Sciences 74, 489-508
Hirai et al. (2001) J Exp. Med. 193, 255-261
Lewis et al. (1982) J. Immunol. 129, 1627
Matsuoka et al. (2000) Science 287, 2013-2017
Nagata et al. (1999) J. Immunol. 162, 1278-1286
Sawyer et al. (2002) Br. J. Pharmacol. 137, 1163-1172
Woodward et al. (1990) Invest. Ophthalomol Vis. Sci. 31, 138-146
Woodward et al. (1993) Eur. J. Pharmacol. 230, 327-333

Xu et al. (1996) J Exp Med. 183, 1001-12
WO 04/106302
WO 04/096777
WO 04/035543
WO 04/032848
WO 05/007094
WO 04/108692
WO 04/108717
WO 04/058265
WO 05/102338

The invention claimed is:

1. A pharmaceutical composition which inhibits chemoattractant receptor-homologous molecule expressed on T-helper 2 cell activity comprising a pharmaceutically acceptable carrier, diluent or excipient and a compound according to Formula (I),

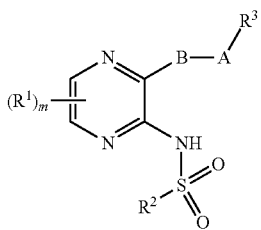
(I)

or stereoisomers, tautomers and pharmaceutically acceptable salts thereof, wherein:

A is selected from the group consisting of:

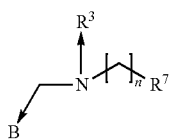
A1

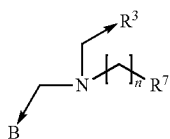
A2

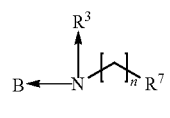
A3

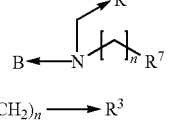
A4

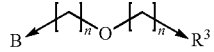
A5 and

A8 where n is 0, 1, 2, 3 or 4;
m is 2;
B is selected from the group consisting of phenyl or piperazinyl;
$R^1$ is hydrogen;
$R^2$ is phenyl, wherein $R^2$ is optionally substituted with one or more substituents selected from the group consisting of halogen, cyano, $C_1$-$C_6$-alkyl;
$R^3$ is selected from the group consisting of $C_1$-$C_6$-alkyl, aryl, heteroaryl, $C_1$-$C_6$-alkylaryl, $C_1$-$C_6$-alkylheteroaryl, $C_3$-$C_8$-cycloalkyl and $C_3$-$C_8$-heterocycloalkyl wherein each of said $C_1$-$C_6$-alkyl, aryl, heteroaryl, $C_1$-$C_6$-alkylaryl, $C_1$-$C_6$-alkylheteroaryl, $C_3$-$C_8$-cycloalkyl and $C_3$-$C_8$-heterocycloalkyl is optionally substituted with one or more substituents selected from the group consisting of halogen, cyano, $C_1$-$C_6$-alkyl, $C_1$-$C_6$-alkoxy, heteroaryl, aryl, thioalkoxy and thioalkyl, or wherein said aryl, heteroaryl, $C_1$-$C_6$-alkylaryl, $C_1$-$C_6$-alkylheteroaryl, $C_3$-$C_8$-cycloalkyl or $C_3$-$C_8$-heterocycloalkyl may be fused to one or more aryl, heteroaryl, $C_3$-$C_8$-cycloalkyl or $C_3$-$C_8$-heterocycloalkyl groups and may be substituted with one or more substituents selected of the group consisting of $C_1$-$C_6$-alkyl, alkoxy, aryl, heteroaryl, carboxyl, cyano, halogen, hydroxy, amino, aminocarbonyl, nitro, sulfoxy, sulfonyl, sulfonamide and trihaloalkyl;
$R^7$ is selected from the group consisting of hydrogen, $C_1$-$C_6$-alkyl, $C_2$-$C_6$-alkenyl, $C_2$-$C_6$-alkynyl, aryl, heteroaryl, $C_3$-$C_8$-cycloalkyl, $C_3$-$C_8$-heterocycloalkyl, carboxy, cyano, amino and hydroxy;
the aryl is selected from phenyl or naphthyl; and
the heteroaryl is selected from pyridyl, indolyl, benzimidazolyl and quinolyl.

2. A compound selected from the group consisting of:
N-{3-[4-(1H-indol-1-ylmethyl)phenyl]pyrazin-2-yl}-2-(trifluoromethyl)-benzenesulfonamide,
2-chloro-N-{3-[4-({methyl[4-(trifluoromethoxy)phenyl]amino}methyl)phenyl]-pyrazin-2-yl}benzenesulfonamide,
N-(3-{4-[(2-ethyl-1H-benzimidazol-1-yl)methyl]phenyl}pyrazin-2-yl)-2-(trifluoromethyl)benzenesulfonamide,
2-chloro-N-[3-(4-{[methyl(phenyl)amino]methyl}phenyl)pyrazin-2-yl]-benzenesulfonamide,
2-chloro-N-(3-{4-[(2-naphthyloxy)methyl]phenyl}pyrazin-2-yl)benzene-sulfonamide,
2-chloro-N-{3-[4-(1H-indol-1-ylmethyl)phenyl]pyrazin-2-yl}benzenesulfonamide,
2-chloro-N-(3-{4-[(5,6,7,8-tetrahydronaphthalen-2-yloxy)methyl]phenyl}-pyrazin2-yl)benzenesulfonamide,
2-chloro-N-(3-{4-[(2-ethyl-1H-benzimidazol-1-yl)methyl]phenyl}pyrazin-2-yl)-benzenesulfonamide,
N-(3-{4-[(1,3-benzodioxol-5-ylamino)methyl]phenyl}pyrazin-2-yl)-2-(trifluoromethyl)benzenesulfonamide,
N-[3-(4-{[(3-methoxybenzyl)oxy]methyl}phenyl)pyrazin-2-yl]-2-(trifluoromethyl)benzenesulfonamide,
3-chloro-N-{3-[4-({methyl [4-(trifluoromethoxy)phenyl]amino}methyl)phenyl]-pyrazin-2-yl}benzenesulfonamide,
4-phenoxy-N-{3-[4-(quinolin-2-ylmethyl)piperazin-1-yl]pyrazin-2-yl}-benzenesulfonamide,
4-methyl-N-{3-[4-({methyl [4-(trifluoromethoxy)phenyl]amino}methyl)phenyl]-pyrazin-2-yl}benzenesulfonamide,
4-chloro-N-[3-(4-{[methyl(phenyl)amino]methyl}phenyl)pyrazin-2-yl]-benzenesulfonamide,
4-cyano-N-{3-[4-({methyl[4-(trifluoromethoxy)phenyl]-amino}-methyl)phenyl]pyrazin-2-yl}benzenesulfonamide, N-[3-(4-{[(4-Fluoro-phenyl)-methyl-amino]-methyl}-phenyl)-pyrazin-2-yl]-2-trifluoromethyl-benzenesulfonamide,
N-(3-{4-[(Methyl-phenyl-amino)-methyl]-phenyl}-pyrazin-2-yl)-2-trifluoromethyl-benzenesulfonamide,
N-[3-(4-{[(4-Cyano-phenyl)-methyl-amino]-methyl}-phenyl)-pyrazin-2-yl]-2-trifluoromethyl-benzenesulfonamide,
N-{3-[4-(4-Fluoro-phenoxymethyl)-phenyl]-pyrazin-2-yl}-2-trifluoromethyl-benzenesulfonamide,
N-(3-{4-[(Ethyl-phenyl-amino)-methyl]-phenyl}-pyrazin-2-yl)-2-trifluoromethyl-benzenesulfonamide,
N-{3-[4-(2,3-Dihydro-benzo[1,4]oxazin-4-ylmethyl)-phenyl]-pyrazin-2-yl}-2-trifluoromethyl-benzenesulfonamide,
N-[3-(4-{[(3-Fluoro-phenyl)-methyl-amino]-methyl}-phenyl)-pyrazin-2-yl]-2-trifluoromethyl-benzenesulfonamide,
N-{3-[4-(6-Chloro-pyridin-3-yloxymethyl)-phenyl]-pyrazin-2-yl}-2-trifluoromethyl-benzenesulfonamide,
N-{3-[4-(2-Pyridin-2-yl-indol-1-ylmethyl)-phenyl]-pyrazin-2-yl}-2-trifluoromethyl-benzenesulfonamide,
N-{3-[4-(5-Fluoro-indol-1-ylmethyl)-phenyl]-pyrazin-2-yl}-2-trifluoromethyl-benzenesulfonamide,
N-[3-(4-Phenoxymethyl-phenyl)-pyrazin-2-yl]-2-trifluoromethyl-benzenesulfonamide,
N-[3-(4-{[(4-Chloro-phenyl)-methyl-amino]-methyl}-phenyl)-pyrazin-2-yl]-2-trifluoromethyl-benzenesulfonamide,
2-Chloro-N-[3-(4-{[(4-cyano-phenyl)-methyl-amino]-methyl}-phenyl)-pyrazin-2-yl]-benzenesulfonamide,
N-[3-(4-{[(3,4-Dichloro-phenyl)-methyl-amino]-methyl}-phenyl)-pyrazin-2-yl]-2-trifluoromethyl-benzenesulfonamide,
N-{3-[4-(4-Cyano-phenoxymethyl)-phenyl]-pyrazin-2-yl}-2-trifluoromethyl-benzenesulfonamide,
N-{3-[4-(6-Fluoro-indol-1-ylmethyl)-phenyl]-pyrazin-2-yl}-2-trifluoromethyl-benzenesulfonamide,
2-Chloro-N-{3-[4-(5-methoxy-2-methyl-indol-1-ylmethyl)-phenyl]-pyrazin-2-yl}-benzenesulfonamide,
N-{3-[4-(4-Methoxy-phenoxymethyl)-phenyl]-pyrazin-2-yl}-2-trifluoromethyl-benzenesulfonamide,
N-(3-{4-[(Benzyl-pyridin-2-yl-amino)-methyl]-phenyl}-pyrazin-2-yl)-2-chloro-benzenesulfonamide,
N-{3-[4-(2,3-Dihydro-indol-1-ylmethyl)-phenyl]-pyrazin-2-yl}-2-trifluoromethyl-benzenesulfonamide,
N-[3-(4-{[(2,4-Dichloro-phenyl)-methyl-amino]-methyl}-phenyl)-pyrazin-2-yl]-2-trifluoromethyl-benzenesulfonamide,
N-{3-[4-(3-Chloro-phenoxymethyl)-phenyl]-pyrazin-2-yl}-2-trifluoromethyl-benzenesulfonamide,
2-Chloro-N-[3-(4-{[(2,4-difluoro-phenyl)-methyl-amino]-methyl}-phenyl)-pyrazin-2-yl]-benzenesulfonamide,
N-{3-[4-(2-Methyl-indol-1-ylmethyl)-phenyl]-pyrazin-2-yl}-2-trifluoromethyl-benzenesulfonamide,
2-Chloro-N-{3-[4-(5-fluoro-indol-1-ylmethyl)-phenyl]-pyrazin-2-yl}-benzenesulfonamide,
2-Chloro-N-[3-(4-{[(2-fluoro-phenyl)-methyl-amino]-methyl}-phenyl)-pyrazin-2-yl]-benzenesulfonamide,
2-Chloro-N-{3-[4-(2-methyl-indol-1-ylmethyl)-phenyl]-pyrazin-2-yl}-benzenesulfonamide,
N-(3-{4-[(Benzyl-pyridin-2-yl-amino)-methyl]-phenyl}-pyrazin-2-yl)-2-trifluoromethyl-benzenesulfonamide,
2-Chloro-N-(3-{4-[(ethyl-pyridin-2-yl-amino)-methyl]-phenyl}-pyrazin-2-yl)-benzenesulfonamide, and
N-{3-[4-(5-Chloro-2-methyl-indol-1-ylmethyl)-phenyl]-pyrazin-2-yl}-2-trifluoromethyl-benzenesulfonamide.

3. A pharmaceutical composition containing at least one compound according to claim 2 and a pharmaceutically acceptable carrier, diluent or excipient thereof.

* * * * *